(12) United States Patent
Chu

(10) Patent No.: US 11,207,166 B2
(45) Date of Patent: Dec. 28, 2021

(54) DEVICES AND METHODS FOR TREATING PELVIC FLOOR DYSFUNCTIONS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 399 days.

(21) Appl. No.: 15/966,823

(22) Filed: Apr. 30, 2018

(65) Prior Publication Data

US 2018/0243069 A1   Aug. 30, 2018

Related U.S. Application Data

(66) Continuation of application No. 13/867,460, filed on Apr. 22, 2013, now Pat. No. 9,974,639, which is a
(Continued)

(51) Int. Cl.
*A61F 2/00* (2006.01)
*A61B 17/04* (2006.01)
(Continued)

(52) U.S. Cl.
CPC ........ *A61F 2/0063* (2013.01); *A61B 17/0401* (2013.01); *A61B 17/0482* (2013.01);
(Continued)

(58) Field of Classification Search
CPC ............ A61B 17/0401; A61B 17/0482; A61B 17/0485; A61B 17/06109;
(Continued)

(56) References Cited

U.S. PATENT DOCUMENTS 669,034 A    2/1901  Manly
3,123,077 A  3/1964  Alcamo
(Continued)

FOREIGN PATENT DOCUMENTS

AU  2015200151 B2  2/2015
EP     412664 A1    2/1991
(Continued)

*Primary Examiner* — Christine H Matthews
*Assistant Examiner* — Joshua Daryl D Lannu
(74) *Attorney, Agent, or Firm* — Brake Hughes Bellermann LLP

(57) ABSTRACT

In one embodiment, an apparatus includes a support portion disposable within a pelvic region and a strap extending from the support portion. The strap has a length and is configured to be disposed at least partially within a pelvic tissue. A sleeve is releasably disposed over at least a portion of the strap. The sleeve has a length that is longer than the length of the strap. In some embodiments, the length of the sleeve is at least twice as long as the length of the strap. In some embodiments, a suture couples the sleeve to the strap. The apparatus can also include a suture disposed at least partially within an interior of the sleeve and forming two strands of suture within the interior of the sleeve. The two strands are separated by a distance defined by a separator portion of the sleeve.

20 Claims, 63 Drawing Sheets

Related U.S. Application Data continuation of application No. 12/341,695, filed on Dec. 22, 2008, now Pat. No. 8,430,807, Substitute for application No. 61/017,212, filed on Dec. 28, 2007.

(51) Int. Cl.
  *A61F 6/08* (2006.01)
  *A61B 17/06* (2006.01)
  *A61B 17/00* (2006.01)

(52) U.S. Cl.
  CPC ...... *A61B 17/06109* (2013.01); *A61F 2/0045* (2013.01); *A61F 6/08* (2013.01); *A61B 17/0485* (2013.01); *A61B 2017/00805* (2013.01); *A61B 2017/06042* (2013.01)

(58) Field of Classification Search
  CPC . A61B 2017/06042; A61B 2017/00805; A61F 6/08; A61F 2/0045; A61F 2/0063
  See application file for complete search history.

(56) References Cited

U.S. PATENT DOCUMENTS

| | | | |
|---|---|---|---|
| 4,324,331 | A | 4/1982 | Ignasiak |
| 4,429,695 | A | 2/1984 | Green |
| 4,775,380 | A | 10/1988 | Seedhom et al. |
| 4,792,336 | A | 12/1988 | Hlavacek et al. |
| 4,919,667 | A | 4/1990 | Richmond |
| 4,935,027 | A | 6/1990 | Yoon |
| 4,998,912 | A | 3/1991 | Scarbrough et al. |
| 5,013,292 | A | 5/1991 | Lemay |
| 5,082,112 | A | 1/1992 | Dunklee |
| 5,108,406 | A | 4/1992 | Lee |
| 5,149,329 | A | 9/1992 | Richardson |
| 5,217,466 | A | 6/1993 | Hasson |
| 5,217,486 | A | 6/1993 | Rice et al. |
| 5,217,494 | A | 6/1993 | Coggins et al. |
| 5,263,969 | A | 11/1993 | Phillips |
| 5,356,432 | A | 10/1994 | Rutkow et al. |
| 5,362,294 | A | 11/1994 | Seitzinger |
| 5,383,905 | A | 1/1995 | Golds et al. |
| 5,405,359 | A | 4/1995 | Pierce |
| 5,413,268 | A | 5/1995 | Green et al. |
| 5,425,747 | A | 6/1995 | Brotz |
| 5,458,636 | A | 10/1995 | Brancato |
| 5,485,917 | A | 1/1996 | Early |
| 5,505,363 | A | 4/1996 | Green et al. |
| 5,534,008 | A | 7/1996 | Acksel |
| 5,562,678 | A | 10/1996 | Booker |
| 5,562,689 | A | 10/1996 | Green et al. |
| 5,584,859 | A | 12/1996 | Brotz |
| 5,643,311 | A | 7/1997 | Smith et al. |
| 5,683,402 | A | 11/1997 | Cosgrove et al. |
| 5,702,397 | A | 12/1997 | Goble et al. |
| 5,741,277 | A | 4/1998 | Gordon et al. |
| 5,752,644 | A | 5/1998 | Bolanos et al. |
| 5,840,011 | A | 11/1998 | Landgrebe et al. |
| 5,865,361 | A | 2/1999 | Milliman et al. |
| 5,899,909 | A | 5/1999 | Claren et al. |
| 5,931,855 | A | 8/1999 | Buncke |
| 5,948,001 | A | 9/1999 | Larsen |
| 5,976,127 | A | 11/1999 | Lax |
| 6,010,447 | A | 1/2000 | Kardjian et al. |
| 6,012,580 | A | 1/2000 | Peters et al. |
| 6,039,686 | A | 3/2000 | Kovac |
| 6,042,534 | A | 3/2000 | Gellman et al. |
| 6,042,536 | A | 3/2000 | Tihon et al. |
| 6,042,592 | A | 3/2000 | Schmitt |
| 6,044,847 | A | 4/2000 | Carter et al. |
| 6,197,036 | B1 | 3/2001 | Tripp et al. |
| 6,200,330 | B1 | 3/2001 | Benderev et al. |
| 6,221,005 | B1 | 4/2001 | Bruckner et al. |
| 6,267,772 | B1 | 7/2001 | Mulhauser et al. |
| 6,273,852 | B1 | 8/2001 | Lehe et al. |
| 6,306,079 | B1 | 10/2001 | Trabucco |
| 6,322,492 | B1 | 11/2001 | Kovac |
| 6,328,686 | B1 | 12/2001 | Kovac |
| 6,375,662 | B1 | 4/2002 | Schmitt |
| 6,382,214 | B1 | 5/2002 | Raz et al. |
| 6,406,423 | B1 | 6/2002 | Scetbon |
| 6,478,727 | B2 | 11/2002 | Scetbon |
| 6,491,703 | B1 | 12/2002 | Ulmsten |
| 6,502,578 | B2 | 1/2003 | Raz et al. |
| 6,506,190 | B1 | 1/2003 | Walshe |
| 6,544,273 | B1 | 4/2003 | Harari et al. |
| 6,547,800 | B2 | 4/2003 | Foerster et al. |
| 6,565,580 | B1 | 5/2003 | Beretta |
| 6,575,998 | B2 | 6/2003 | Beyar |
| 6,582,443 | B2 | 6/2003 | Cabak et al. |
| 6,592,515 | B2 | 7/2003 | Thierfelder et al. |
| 6,592,610 | B2 | 7/2003 | Beyar |
| 6,595,911 | B2 | 7/2003 | Lovuolo |
| 6,596,001 | B2 | 7/2003 | Stormby et al. |
| 6,599,235 | B2 | 7/2003 | Kovac |
| 6,599,310 | B2 | 7/2003 | Leung et al. |
| 6,612,977 | B2 | 9/2003 | Staskin et al. |
| 6,638,209 | B2 | 10/2003 | Landgrebe |
| 6,638,210 | B2 | 10/2003 | Berger |
| 6,638,211 | B2 | 10/2003 | Suslian et al. |
| 6,641,524 | B2 | 11/2003 | Kovac |
| 6,641,525 | B2 | 11/2003 | Rocheleau et al. |
| 6,648,899 | B2 | 11/2003 | Kalinski et al. |
| 6,648,921 | B2 | 11/2003 | Anderson et al. |
| 6,652,450 | B2 | 11/2003 | Neisz et al. |
| 6,666,817 | B2 | 12/2003 | Li |
| 6,669,706 | B2 | 12/2003 | Schmitt et al. |
| 6,669,735 | B1 | 12/2003 | Pelissier |
| 6,673,010 | B2 | 1/2004 | Skiba et al. |
| 6,691,711 | B2 | 2/2004 | Raz et al. |
| 6,695,855 | B1 | 2/2004 | Gaston |
| 6,702,827 | B1 | 3/2004 | Lund et al. |
| 6,730,110 | B1 | 5/2004 | Harari et al. |
| 6,746,455 | B2 | 6/2004 | Beyar et al. |
| 6,752,814 | B2 | 6/2004 | Gellman et al. |
| 6,755,781 | B2 | 6/2004 | Gellman |
| 6,808,487 | B2 | 10/2004 | Migliari |
| 6,830,052 | B2 | 12/2004 | Carter et al. |
| 6,848,152 | B2 | 2/2005 | Genova et al. |
| 6,881,184 | B2 | 4/2005 | Zappala |
| 6,890,338 | B1 | 5/2005 | Davis et al. |
| 6,908,425 | B2 | 6/2005 | Luscombe |
| 6,911,003 | B2 | 6/2005 | Anderson et al. |
| 6,911,034 | B2 | 6/2005 | Nobles et al. |
| 6,932,759 | B2 | 8/2005 | Kammerer et al. |
| 6,936,052 | B2 | 8/2005 | Gellman et al. |
| 6,946,003 | B1 | 9/2005 | Wolowacz et al. |
| 6,953,428 | B2 | 10/2005 | Gellman et al. |
| 6,960,160 | B2 | 11/2005 | Browning |
| 6,971,986 | B2 | 12/2005 | Staskin et al. |
| 6,991,597 | B2 | 1/2006 | Gellman et al. |
| 7,011,688 | B2 | 3/2006 | Gryska et al. |
| 7,025,772 | B2 | 4/2006 | Gellman et al. |
| 7,048,682 | B2 | 5/2006 | Neisz et al. |
| 7,056,333 | B2 | 6/2006 | Walshe |
| 7,070,556 | B2 | 7/2006 | Anderson et al. |
| 7,070,558 | B2 | 7/2006 | Gellman et al. |
| 7,083,568 | B2 | 8/2006 | Neisz et al. |
| 7,083,637 | B1 | 8/2006 | Tannhauser |
| 7,090,686 | B2 | 8/2006 | Nobles et al. |
| 7,094,199 | B2 | 8/2006 | Petros et al. |
| 7,112,171 | B2 | 9/2006 | Rocheleau et al. |
| 7,112,210 | B2 | 9/2006 | Ulmsten et al. |
| 7,122,039 | B2 | 10/2006 | Chu |
| 7,131,943 | B2 | 11/2006 | Kammerer |
| 7,131,944 | B2 | 11/2006 | Jacquetin |
| 7,198,597 | B2 | 4/2007 | Siegel et al. |
| 7,204,801 | B2 | 4/2007 | Grocela |
| 7,204,802 | B2 | 4/2007 | De Leval |
| 7,223,229 | B2 | 5/2007 | Inman et al. |
| 7,226,407 | B2 | 6/2007 | Kammerer et al. |
| 7,226,408 | B2 | 6/2007 | Harai et al. |
| 7,229,453 | B2 | 6/2007 | Anderson et al. |
| 7,235,043 | B2 | 6/2007 | Gellman et al. |

(56) References Cited

U.S. PATENT DOCUMENTS

| | | |
|---|---|---|
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,686,506 B2 | 3/2010 | Babkes et al. |
| 7,722,527 B2 | 5/2010 | Bouchier et al. |
| 7,981,023 B2 | 7/2011 | Nowlin et al. |
| 8,187,247 B2 | 5/2012 | Lornell |
| 8,430,807 B2 | 4/2013 | Chu |
| 8,491,458 B2 | 7/2013 | Chu |
| 8,517,914 B2* | 8/2013 | Anderson ........ A61B 17/06109 600/37 |
| 9,078,728 B2 | 7/2015 | Chu |
| 9,125,716 B2 | 9/2015 | Chu |
| 9,668,845 B2 | 6/2017 | Chu et al. |
| 2002/0010457 A1 | 1/2002 | Duchon et al. |
| 2002/0036221 A1 | 3/2002 | Gabbay et al. |
| 2002/0091373 A1 | 7/2002 | Berger |
| 2002/0128670 A1 | 9/2002 | Ulmsten et al. |
| 2002/0147382 A1* | 10/2002 | Neisz ............... A61B 17/06109 600/29 |
| 2002/0151909 A1 | 10/2002 | Gellman et al. |
| 2002/0156489 A1 | 10/2002 | Gellman et al. |
| 2003/0004395 A1 | 1/2003 | Therin |
| 2003/0036797 A1 | 2/2003 | Malaviya et al. |
| 2003/0125715 A1 | 7/2003 | Kuehn et al. |
| 2003/0130670 A1 | 7/2003 | Anderson et al. |
| 2003/0149334 A1 | 8/2003 | Ulmsten et al. |
| 2003/0220538 A1 | 11/2003 | Jacquetin |
| 2003/0225424 A1 | 12/2003 | Benderev |
| 2004/0006353 A1* | 1/2004 | Bosley ............. A61B 17/06109 606/151 |
| 2004/0039453 A1 | 2/2004 | Anderson et al. |
| 2004/0073234 A1 | 4/2004 | Chu et al. |
| 2004/0087970 A1 | 5/2004 | Chu et al. |
| 2004/0106847 A1 | 6/2004 | Benderev |
| 2004/0181243 A1 | 9/2004 | Chu et al. |
| 2004/0225181 A1 | 11/2004 | Chu et al. |
| 2004/0230206 A1 | 11/2004 | Gellman et al. |
| 2004/0249240 A1 | 12/2004 | Goldmann et al. |
| 2004/0249397 A1 | 12/2004 | Delorme et al. |
| 2004/0267088 A1 | 12/2004 | Kammerer |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107660 A1 | 5/2005 | Valtchev |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0181327 A1 | 8/2005 | Graham et al. |
| 2005/0192600 A1 | 9/2005 | Nicolo et al. |
| 2005/0245787 A1 | 11/2005 | Cox et al. |
| 2005/0250978 A1 | 11/2005 | Kammerer |
| 2005/0256366 A1 | 11/2005 | Chu |
| 2005/0256530 A1 | 11/2005 | Petros |
| 2005/0261547 A1 | 11/2005 | Bouffier |
| 2005/0277807 A1 | 12/2005 | Maclean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1* | 6/2006 | Kovac ................ A61F 2/0045 600/37 |
| 2006/0173237 A1 | 8/2006 | Jacquetin |
| 2006/0183966 A1 | 8/2006 | Neisz et al. |
| 2006/0195007 A1* | 8/2006 | Anderson .......... A61B 17/0401 600/29 |
| 2006/0195010 A1 | 8/2006 | Arnal |
| 2006/0205995 A1 | 9/2006 | Browning |
| 2006/0206096 A1 | 9/2006 | Accisano et al. |
| 2006/0211911 A1 | 9/2006 | Jao et al. |
| 2006/0229596 A1 | 10/2006 | Weiser et al. |
| 2006/0260618 A1 | 11/2006 | Hodroff |
| 2006/0264698 A1 | 11/2006 | Kondonis et al. |
| 2006/0287571 A1 | 12/2006 | Gozzi et al. |
| 2007/0015953 A1 | 1/2007 | Maclean |
| 2007/0038017 A1 | 2/2007 | Chu et al. |
| 2007/0055095 A1* | 3/2007 | Chu .................... A61F 2/0045 600/37 |
| 2007/0123915 A1 | 5/2007 | Kammerer et al. |
| 2007/0169877 A1 | 7/2007 | Leeflang et al. |
| 2007/0202542 A1 | 8/2007 | Babu et al. |
| 2007/0203508 A1 | 8/2007 | White et al. |
| 2007/0276358 A1 | 11/2007 | Barzell et al. |
| 2007/0282259 A1 | 12/2007 | Morris et al. |
| 2008/0033486 A1 | 2/2008 | Whittaker et al. |
| 2008/0082105 A1 | 4/2008 | Chu |
| 2008/0091221 A1 | 4/2008 | Brubaker et al. |
| 2008/0103587 A1 | 5/2008 | Henderson et al. |
| 2008/0132754 A1 | 6/2008 | Thierfelder et al. |
| 2008/0287732 A1 | 11/2008 | Kuntz |
| 2008/0287971 A1 | 11/2008 | Kuntz et al. |
| 2009/0137944 A1 | 5/2009 | Haarala et al. |
| 2009/0171140 A1 | 7/2009 | Chu |
| 2009/0171142 A1 | 7/2009 | Chu |
| 2009/0216075 A1 | 8/2009 | Bell et al. |
| 2009/0221867 A1 | 9/2009 | Ogdahl et al. |
| 2010/0145140 A1 | 6/2010 | Chu |
| 2010/0268018 A1 | 10/2010 | Chu |
| 2011/0112357 A1 | 5/2011 | Chapman et al. |
| 2013/0231525 A1 | 9/2013 | Chu |
| 2015/0366646 A1 | 12/2015 | Chu |

FOREIGN PATENT DOCUMENTS

| | | |
|---|---|---|
| EP | 1201189 A2 | 5/2002 |
| EP | 1508305 A2 | 2/2005 |
| EP | 1520554 A2 | 4/2005 |
| EP | 1563794 A1 | 8/2005 |
| GB | 670349 A | 4/1952 |
| JP | 2004-510489 A | 4/2004 |
| JP | 2005-518869 A | 6/2005 |
| JP | 2007-536004 A | 12/2007 |
| JP | 2008-508046 A | 3/2008 |
| JP | 2008-523926 A | 7/2008 |
| JP | 2009-523484 A | 6/2009 |
| JP | 2009-527272 A | 7/2009 |
| JP | 2009-539558 A | 11/2009 |
| WO | 1998/035632 A1 | 8/1998 |
| WO | 2002/078571 A2 | 10/2002 |
| WO | 2003/059174 A2 | 7/2003 |
| WO | 2003/092546 A2 | 11/2003 |
| WO | 2003/096929 A1 | 11/2003 |
| WO | 2004/091442 A2 | 10/2004 |
| WO | 2005110274 A2 | 11/2005 |
| WO | 2005/122721 A2 | 12/2005 |
| WO | 2006/046950 A1 | 5/2006 |
| WO | 2006/069078 A2 | 6/2006 |
| WO | 2006/108045 A2 | 10/2006 |
| WO | 2007/016698 A2 | 2/2007 |
| WO | 2007/019274 A2 | 2/2007 |
| WO | 2007/019374 A2 | 2/2007 |
| WO | 2007/059199 A2 | 5/2007 |
| WO | 2007/059306 A1 | 5/2007 |
| WO | 2007/059368 A1 | 5/2007 |

(56) References Cited

FOREIGN PATENT DOCUMENTS

| | | |
|---|---|---|
| WO | 2007/087132 A1 | 8/2007 |
| WO | 2007/097994 A2 | 8/2007 |
| WO | 2007/149348 A2 | 12/2007 |
| WO | 2009/086355 A2 | 7/2009 |
| WO | 2009/086369 A2 | 7/2009 |
| WO | 2010/065592 A1 | 6/2010 |
| WO | 2010/121053 A1 | 10/2010 |

\* cited by examiner

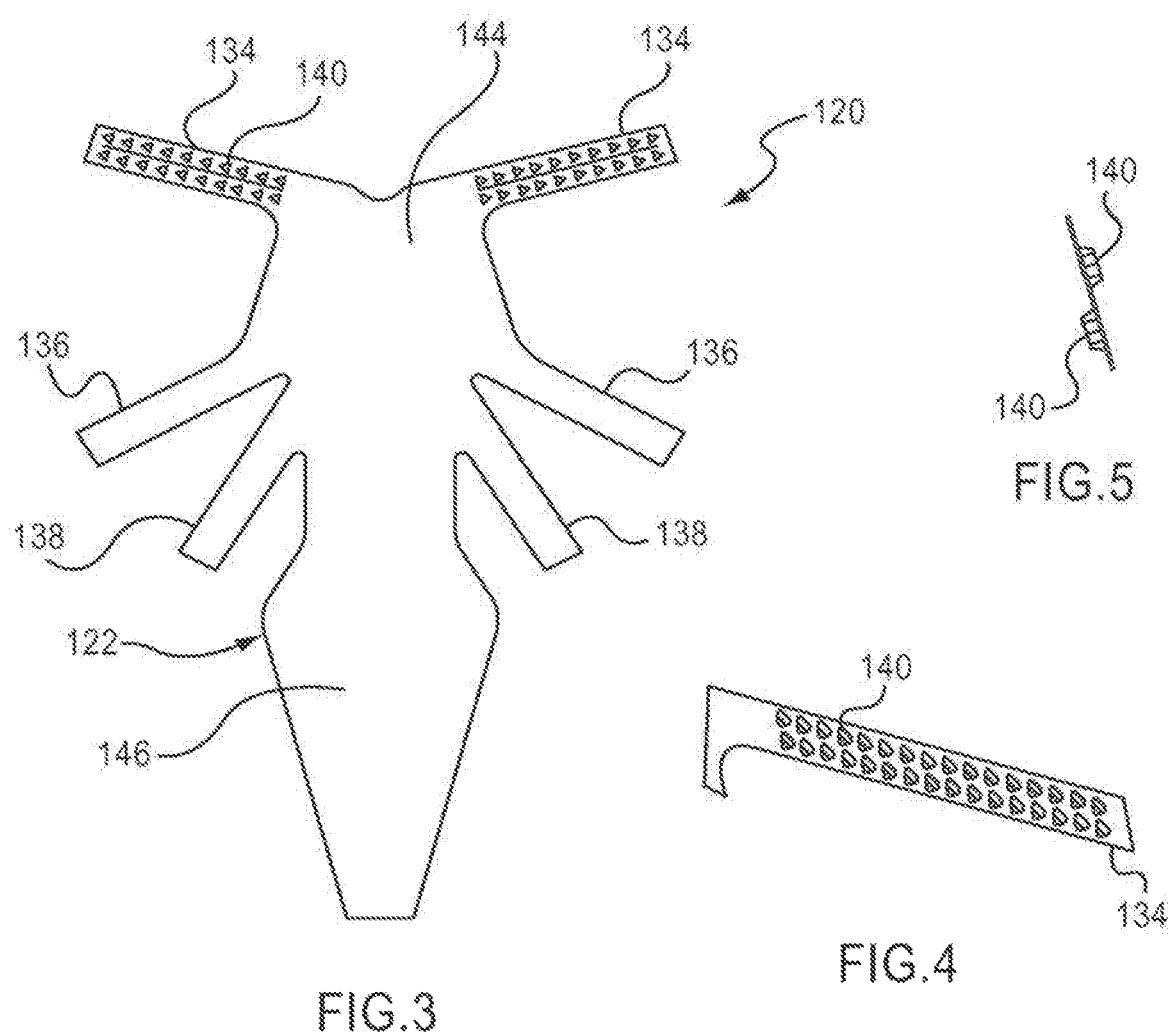

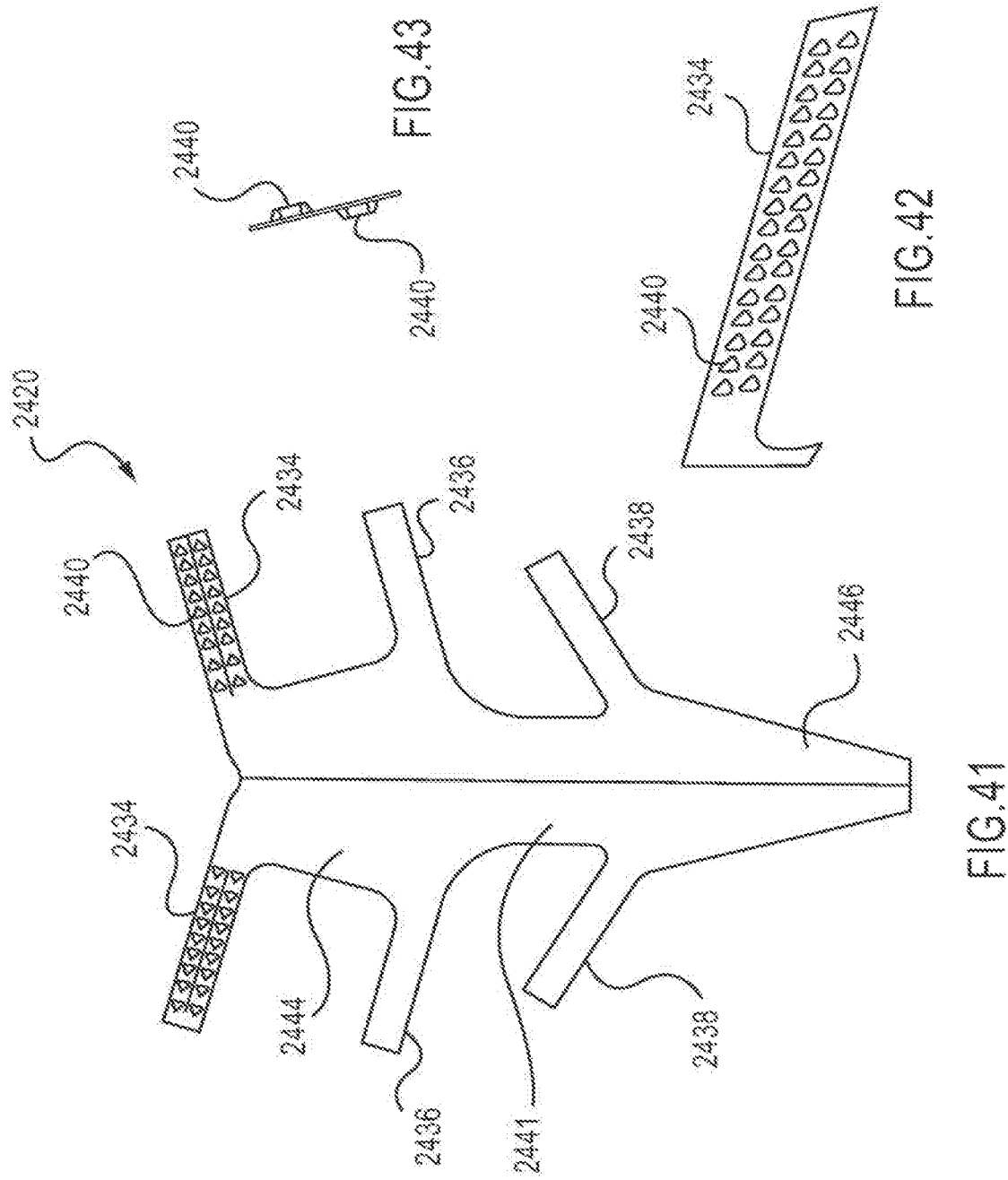

DEVICES AND METHODS FOR TREATING PELVIC FLOOR DYSFUNCTIONS

CROSS-REFERENCE TO RELATED APPLICATIONS

This application is a Continuation of, and claims priority to, U.S. patent application Ser. No. 13/867,460, filed on Apr. 22, 2013, which is a Continuation of U.S. patent application Ser. No. 12/341,695, filed on Dec. 22, 2008, entitled "DEVICES AND METHODS FOR TREATING PELVIC FLOOR DYSFUNCTIONS", which, in turn, claims priority to U.S. Provisional Patent Application No. 61/017,212, filed on Dec. 28, 2007, entitled "DEVICES AND METHODS FOR TREATING PELVIC FLOOR DYSFUNCTIONS", the disclosures of which are hereby incorporated by reference in their entireties.

BACKGROUND

The disclosed invention relates generally to medical devices and more particularly to implants and methods for delivering implants within a pelvic region of a patient to treat various pelvic dysfunctions.

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina. It is relatively common for a hysterocele and cystocele or hysterocele and rectocele, or other combinations thereof to occur at the same time. It is also common for different types of prolapse to occur in relatively quick succession.

Treatment has included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. For example, various sizes of implants are needed to accommodate different sized anatomy and pelvic regions of a patient. For example, if an implant is too large for the particular patient, damage to surrounding tissue can occur. In some cases, an implant that is too small can increase the chance of prolapse recurrence.

Depending on the particular condition to be treated and the implant used, pelvic floor repair can require various fixation locations within a pelvic region. For example, an implant can be secured using a number of fixation points. Sutures are often used to bridge, anchor and suspend the implant in place. Sutures may not provide enough surface area for tissue in-growth, and may require knotting in order to be secured. Implants formed with mesh material can provide for tissue in-growth and the width of the mesh can help prevent tissue cutting. An implant can also have roughened or tanged edges to grip surrounding tissue and hold the mesh implant in place until tissue in-growth occurs. Delivery of some implants includes the use of a sleeve to cover some or all of an implant to protect the implant from damage during delivery and to prevent premature engagement of the implant to surrounding tissue.

Various complications can occur during a procedure to deliver and secure a pelvic implant due to, for example, space constraints for performing the implantation procedure. Often, implants can become damaged during delivery due to the type of delivery device and/or the type of implant, or due to excessive handling of the implant during the implant procedure. Thus, it would be desirable to provide improved pelvic implants and delivery processes associated with such implants to help prevent damage to the implant during implantation.

SUMMARY OF THE INVENTION

In one embodiment, an apparatus includes a support portion disposable within a pelvic region and a strap extending from the support portion. The strap has a length and is configured to be disposed at least partially within a pelvic tissue. A sleeve is releasably disposed over at least a portion of the strap. The sleeve has a length that is longer than the length of the strap. In some embodiments, the length of the sleeve is at least twice as long as the length of the strap. In some embodiments, a suture couples the sleeve to the strap. The apparatus can also include a suture disposed at least partially within an interior of the sleeve and forming two strands of suture within the interior of the sleeve. The two strands are separated by a distance defined by a separator portion of the sleeve.

BRIEF DESCRIPTION OF THE DRAWINGS

FIG. 3 is a top view of a portion of the implant of FIG. 2.

FIG. 4 is a top view of a strap of the implant of FIG. 2.

FIG. 5 is a side view of a portion of the strap of FIG. 4.

FIG. 41 is a top view of another embodiment of an implant.

FIG. 42 is a side view of a portion of the implant of FIG. 41.

FIG. 43 is a side view of a portion of the implant shown in FIG. 42.

DETAILED DESCRIPTION

Figure 1:
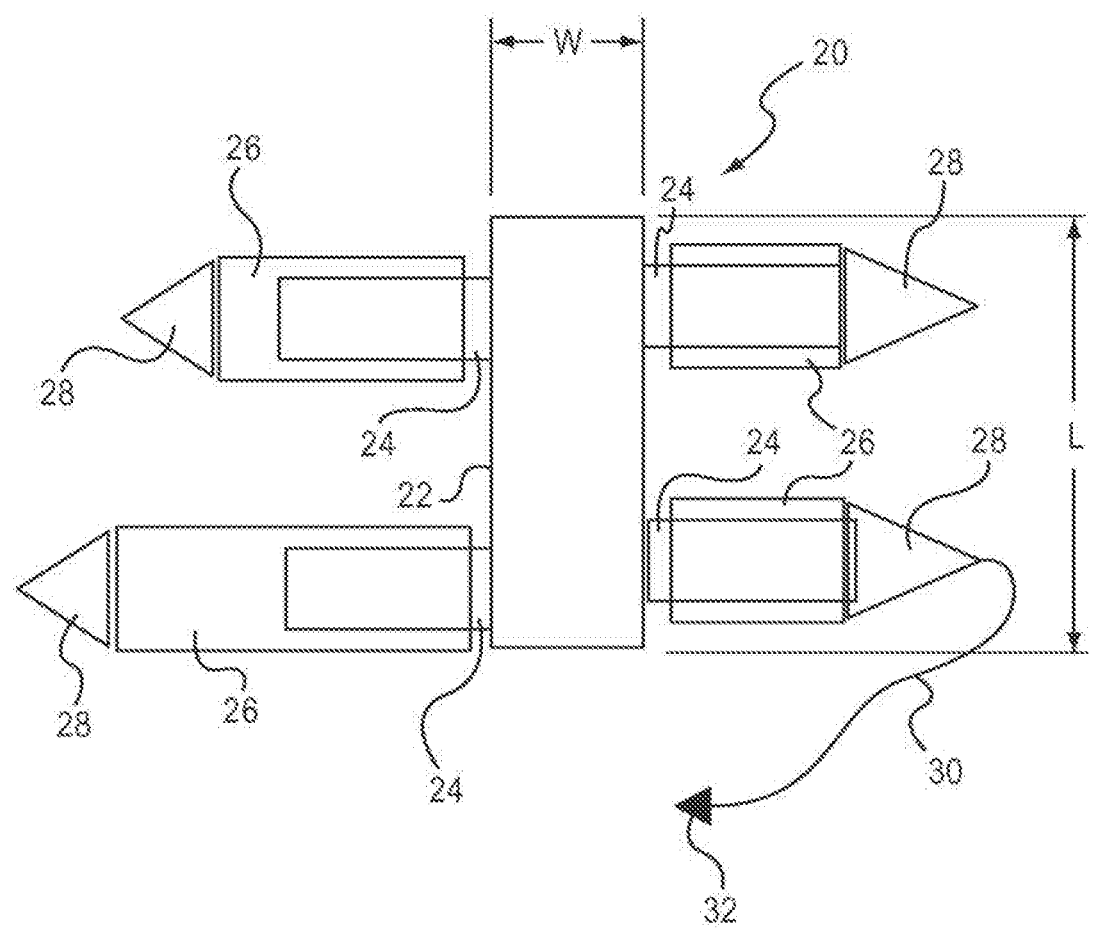
FIG. 1 is a schematic illustration of an embodiment of an implant.

The devices and methods described herein are generally directed to implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at several different locations within the pelvic space to treat many different female pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods arc also described for delivering and securing an implant assembly within the patient.

An implant according to an embodiment of the invention can include one or more tanged portion and/or one or more detanged portion. The terms "tanged" or "tangs" as used herein mean roughened or jagged edges or areas, such as can result from cutting a woven or knit mesh material. The tanged portion can be used, for example, to anchor or secure the implant to tissue. An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include a single vaginal incision, such as an anterior vaginal incision and/or an anterior vaginal incision and a posterior vaginal incision. In some embodiments, a procedure may include an exterior incision.

Various embodiments of implants are described herein. An implant can be delivered to a pelvic region of a patient using a variety of different delivery devices, only some examples of which are described herein. Various delivery aids are also described, some of which can be included as part of an implant (e.g., provided to a physician assembled) some of which can be assembled to an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

In some embodiments, an implant can be associated to delivery aid, such as a sleeve assembly or dilator device, after such delivery aid has been placed within a pelvic region. For example, in an embodiment of an implant having multiple straps, prior placement of a delivery aid can help with coordinating and organizing the placement of the various straps. Placing a delivery aid within a pelvic region first also helps reduce handling of the implant which can reduce damage to the implant during an implantation procedure.

In one embodiment, an apparatus includes a support portion disposable within a pelvic region and a strap extending from the support portion. The strap has a length and is configured to be disposed at least partially within a pelvic tissue. A sleeve is releasably disposed over at least a portion of the strap. The sleeve has a length that is longer than the length of the strap. In some embodiments, the length of the sleeve is at least twice as long as the length of the strap. In some embodiments, a suture couples the sleeve to the strap. The suture can be at least partially disposed within an interior of the sleeve and form two strands of suture within the interior of the sleeve. The two strands can be separated by a distance defined by a separator portion of the sleeve.

In another embodiment, an apparatus includes a support member implantable within a pelvic region and a strap that extends from the support member. The strap is configured to be secured within a pelvic tissue to support the support member within the pelvic region. A sleeve is releasably disposed over at least a portion of the strap, and has a first wall and a second wall defining an interior space. A suture is coupled to the strap and coupled to the sleeve. The suture is disposed at least partially within the interior space of the sleeve and forms two strands of suture within the interior space of the sleeve. The two strands being separated by a distance defined by a separator portion of the sleeve.

In another embodiment, an apparatus includes a support member implantable within a pelvic region. A first strap extends from the support member and is configured to be secured to an arcus tendineus when the support member is implanted within the pelvic region. A second strap extends from the support member distal of the first strap and is configured to be secured to a sacrospinous ligament when the support member is implanted within a pelvic region. The first strap has a length such that the first strap can be secured to the arcus tendineus but cannot extend to a vagina after being secured to the arcus tendineus. The second strap has a length such that the second strap can be secured to the sacrospinous ligament, but cannot extend to the vagina after being secured to the sacrospinous ligament. The first strap and the second strap configured to help support the support member at least partially beneath the bladder neck when the first strap is secured to the arcus tendineus and the second strap is secured to the sacrospinous ligament.

In another embodiment, a method includes inserting a pelvic implant through an anterior vaginal incision and into a pelvic region. The pelvic implant includes a support portion, a strap extending from the support portion, and a sleeve disposed over the strap. The sleeve has a length greater than a length of the strap. The sleeve and strap are pulled at least partially through a pelvic tissue such that a first portion of the sleeve is disposed within the pelvic tissue and a second portion of the sleeve extends through the vaginal incision and the strap is disposed at least partially within the pelvic tissue but does not extend through the vaginal incision. The sleeve is removed from the strap, leaving the strap at least partially disposed within the pelvic tissue.

In another embodiment, a method includes inserting an implant through a vaginal incision and into a pelvic region. The implant includes a first strap and a second strap extending from a support portion. The first strap is placed through a sacrospinous ligament of a first side of the pelvic region. The second strap is placed through an arcus tendineus of the first side of the pelvic region. An anterior portion of the support portion is secured to at least one of an obturator or the arcus tendineus of the first side of the pelvic region.

In another embodiment, a method includes providing a pelvic implant having a strap extending from a support portion of the implant. The strap has a first length. A portion of the support portion of the implant is cut such that the strap has a second length greater than the first length of the strap. After cutting the support portion, at least a portion of the strap is placed through a pelvic tissue to at least partially secure the implant within a pelvic region of a patient.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

FIG. 1 is a schematic illustration of an implant according to an embodiment of the invention. The implant 20 can be used, for example, to treat various conditions, including, but not limited to anterior repairs, posterior repairs, total repair, each with or without apical repair, or a combination thereof. An implant 20 can include a support portion 22, and one or more straps 24. The support portion 22 can be a variety of different shapes, sizes and configurations depending on the intended use for the particular implant. For example, in some embodiments, the support portion 22 can be substantially rectangular, square, oval, or elliptical. The support portion 22 can be shaped and sized to support a bladder (e.g., to treat a cystocele) and/or a bladder neck and/or support a uterus (e.g., to treat a hysterocele) and/or to support a rectum (e.g. to treat a rectocele). The support portion 22 can include, for example, a posterior support portion and/or an anterior support portion. The support portion has a length L and a width W. In some embodiments, the length L can be, for example, between 12.6 cm (4.96 inches) to 27.69 cm (10.90 inches), and the width W can be, for example, between 4.27 cm (1.68 inches) to 8.31 cm (3.27 inches).

The support portion 22 and/or the straps 24 can each be formed with a mesh material to allow tissue in-growth to the implant 20 after implantation. For example, some or all of the implant 20 can be formed with a mesh material as described in U.S. Patent Pub. 2005/0038452 A1 to Chu, the disclosure of which is hereby incorporated by reference in its entirety. In some embodiments, some or all of an implant 20 can be formed with the Advantage® Mesh or the Polyform™ Synthetic Mesh material each provided by Boston Scientific Corporation ("BSC"). The implant 20 can be monolithically formed or alternatively, the implant 20 can be formed with multiple different materials and/or can include multiple different components or portions coupled together. In some embodiments, an implant 20 can be formed with a combination of materials including synthetic and biological materials. For example, the support portion 22 can be formed with a first biocompatible material and the straps 24 can be formed with a second biocompatible material different than the first material. In another example, the support portion 22 can be formed with a biological material, and the straps can be formed with a synthetic material. The straps 24 and support portion 22 can also have a different weave, pitch, texture, color, and pattern from each other.

The straps 24 can be formed monolithically with the support portion 22 or be a separate component coupled to the support portion 22. A strap 24 and support portion 22 can be coupled in an abutting relationship, an overlapping relationship, or can be bridged. The straps 24 can be coupled to the support portion 22 by, for example, heat bonding, gluing, using fasteners, and/or sewing. In some embodiments, a strap 24 can include a heat seal along its length or a portion of its length to prevent or reduce stretch.

In some embodiments the support portion 22 and/or straps 24 include one or more tanged portions (as described above). The tangs allow the implant 20 to be anchored within pelvic tissue without the use of additional anchoring mechanisms or sutures. In some embodiments, an implant 20 includes tangs on an edge along an entire length of the implant 20. In other embodiments, the implant 20 includes tangs covering substantially all of an exterior surface of the implant. In some embodiments, tangs are only on the straps 24 of the implant 20. For example, in some embodiments the straps 24 include a tanged portion to engage and help secure the implant to pelvic tissue. Pelvic tissue can include, for example, ligaments, muscle (such as an obturator internus muscle or an obturator externus muscle), fascia, or any other structure or tissue within a pelvic region of a patient.

As with the support portion 22, the straps 24 can have a variety of different configurations and/or different sizes (e.g. lengths, widths), depending on the intended use for the particular implant and the intended implantation site for the straps within the pelvic region. For example, straps 24 can have a length to accommodate securing the strap 24 to specific anatomical location within the pelvic region, such as a sacrospinous ligament, an arcus tendineus, a levator muscle, etc. In some embodiments, an implant for use in supporting a bladder neck includes straps that are secured to the arcus tendineus. Such straps are typically relatively short in length, as the distance from the placement of the implant to the arcus tendineus does not require a long strap.

The length of a particular strap 24 can depend on the particular tissue (e.g., ligament, muscle) that the strap 24 is intended to be secured to, such that trimming of the strap 24 during or after placement can be reduced or eliminated. For example, in some embodiments, a strap 24 that is configured to be secured to an anterior area of a pelvis, can have a length of about 15 cm (5.9 inches). Such a length is sufficiently long to secure the strap 24, to, for example, an arcus tendineus, but is too short to extend through an exterior incision in the patient (e.g., when the support portion is properly placed in the pelvic region of the patient). In other embodiments, an anterior strap can have a length such that the strap can be passed through tissue leading towards an obturator foramen, but not long enough to pass through the obturator foramen. A length of an anterior strap, together with a width of the anterior portion of the support portion 22 can be, for example, between about 5 cm (2 inches) and 30 cm (12 inches). In some embodiments, a length measured from a center line of the support portion 22 to an end of the strap can be about 7.5 cm (3.0 inches). A posterior strap 24 can have a length, for example, such that the strap 24 can be placed through, or secured to, tissue, such as a sacrospinous ligament, but is not long enough to return back through a vaginal insertion point. In some embodiments, a strap 24 can have a length such that it can extend from a pelvic region through an exterior incision of the patient. In such embodiments, a sleeve 26 can provide an extracorporeal means to release a strap from the sleeve 26 and obviate intracorporeal strap trimming.

The implant 20 can also include one or more sleeve members 26 (also referred to as a "sleeves") each coupled to one or more of the straps 24. For example, a sleeve member 26 can be coupled to the strap 24 via a suture (not shown in FIG. 1), with a heat seal (not shown in FIG. 1), or other attachment methods, such as with fasteners or adhesive. The sleeve member 26 can be used during the insertion of the implant into a pelvic region to prevent the straps 24 from prematurely engaging tissue during the delivery procedure. For example, if a strap 24 includes a tanged portion, a sleeve member 26 can prevent the tangs from engaging tissue as the implant is being delivered into the pelvic region. Conversely, when no sleeve 26 is disposed on a strap 24 having tanged edges, the tangs can engage the surrounding tissue making it difficult to smoothly slide the strap 24 for adjustment. A sleeve 26 can also help in a process to adjust the tension of a strap 24, for example, to relieve strap tension.

The sleeves 26 can also protect the straps 24 from damage during delivery. The sleeves 26 can have a reduced profile at a distal end portion, enabling it to more easily travel through the tissue during delivery. For example, a sleeve 26 can be tapered. The same type or configuration of sleeve 26 can be disposed over each strap 24 of an implant 20, or a different type of sleeve 26 can be disposed over each strap 24 of an implant 20. In some embodiments, there is no sleeve 26, or a sleeve 26 is disposed over only one or some of the straps 24. The sleeve 26 can be transparent, semi-transparent, colored, non-colored, or a combination thereof. The sleeve 26 can be, for example, tapered, flat, and/or tubular. A sleeve 20 can be formed for example, with a clear, thin, flexible biocompatible polymer, and be configured to allow the user to examine or view the implant 20 (e.g., straps) disposed within the sleeve 26. After the straps 24 are positioned at a desired location within the pelvic region, the sleeves 26 can be removed from the implant 20, as described in more detail below. Although the sleeves 26 are described herein as being part of a sleeve assembly or dilator assembly, it should be understood that a sleeve 26 can alternatively be individually coupled to a strap.

As stated previously, an implant 20 can have any number of straps 24 depending on the particular intended use for the implant 20. For example, an implant 20 can have between one and twenty straps 24. In some embodiments, one or more straps 24 can extend from the support portion 22 (e.g., a posterior support portion or an anterior support portion) at an angle. Such an angle of a strap 24 can vary in different embodiments, for example between 20 to 160 degrees from a centerline of the support portion 22.

In some embodiments, the straps 24 are configured to be secured to tissue by an interference fit or frictional fit with the surrounding tissue. For example, the strap 24 can be pulled through a pelvic tissue using, for example, a sleeve or dilator (as described herein) that is configured to dilate or expand the tissue and provide a lead-in (e.g., passageway) for the strap to be pulled through the tissue. The pelvic tissue is dilated such that the strap can be pulled through the tissue, but then prolapses or retracts to a smaller size to provide a frictional interaction between the tissue and the strap. The strap can also be flexible such that even if a width of the strap 24 is greater than a width of a corresponding passage in the tissue formed by the lead-in device (e.g., dilator or sleeve), the strap can flex to be pulled through the tissue, and the tissue can dilate or expand to receive the strap 24. In some embodiments one or more straps 24 are tapered toward their distal end, and are larger in width near the support portion 22, which further provides a lead-in through the tissue.

In some embodiments, one or more of the straps 24 are substantially the same length as their corresponding sleeves 26. In other embodiments, one or more straps 24 are shorter than their corresponding sleeves 26. In such an embodiment, the sleeve can be used to provide an extension to the strap to help in the insertion process. By forming the strap 24 with a length just sufficient to be secured to a target tissue site, the implant 20 can be formed with less material. For example, in many cases, as mentioned above, a strap may need to be trimmed after placement in a pelvis region, and the trimmed material is then discarded. The use of a strap 24 having a length configured for the particular use can thus eliminate the need for trimming and also reduce the costs to manufacture the implant 20. Such embodiments of a strap 24 can also help prevent strap stretch that can occur during insertion of the implant due to pulling on a longer length strap. A strap 24 having a length shorter than a corresponding sleeve 26 can also help maintain the cleanliness of a strap 24 during insertion as a substantial portion of the strap 24 that will be secured within the pelvis will be protected within the sleeve 26. A strap 24 having a shorter length than its corresponding sleeve 26 can also reduce friction between the strap 24 and an interior surface of the sleeve 26 (due to reduced surface area contact), allowing easier, removal of the sleeve 26.

As stated above, the support portion 22 and straps 24 can be separate components. In some embodiments, a sleeve and strap assembly is provided that is configured to be coupled to a support portion of an implant. For example, a support portion and one or more sleeve and strap assembly can be provided to a user (e.g., a physician) unassembled. The user can then secure one or more of the sleeve and strap assemblies to the support portion to form the implant. Such embodiments are described in more detail below.

As shown in FIG. 1, a dilator 28 can also be coupled to the sleeve 26 and used to assist in the delivery of the implant 20 to the pelvic region. A proximal end portion (or trailing end) of a dilator 28 can be coupled to a sleeve 26, for example, by crimping, knotting, heat bonding, heat sealing, stitching, stretching, or tipping or a combination thereof. In some embodiments, the sleeve 26 is formed monolithically with the dilator 28. The dilator 28 can produce a larger passage through tissue to facilitate strap placement. Using a dilator 28 to introduce a strap 24 into a pelvic region can reduce handling or pulling of the implant 20 itself, thereby reducing or eliminating potential damage to the implant 20.

The dilator 28 can be a variety of different configurations. For example, the dilator 28 can be a variety of different lengths, shapes, diameters, etc. The dilator 28 can expand a passage formed by a trocar needle 32 (as described below) during insertion through a tissue, to ease the transition of the opening of the tissue to a cross-section of the sleeve 26. The sleeve 26 can also be tapered, which helps provide a lead-in through or dilation of the tissue. The dilator 28 can be flexible, semi rigid, or rigid. The dilator 28 can be curved or substantially linear. In some embodiments, the dilator 28 is tubular shaped. For example, the dilator device 28 can define a lumen therethrough. The dilator 28 can also be tapered from a larger diameter at a proximal or trailing end to a smaller diameter at a distal or leading end of the dilator 28. The dilator 28 can also be color-coded. For example, when an implant 20 having multiple straps 24 is to be delivered to a pelvic region, dilators 28 each having a unique color to indicate where that strap 24 is to be placed within a pelvis can be coupled to each strap. Such color-coding can help with the organization of the delivery process. For example, in one embodiment, a pair of anterior straps can be coupled to dilators that are blue and a pair of posterior straps can be coupled to dilators that are white. In some embodiments, additional coding of the dilators can be included to further help organize the straps. For example, a pair of dilators coupled to anterior straps can be blue colored and one of the dilators can further be striped (e.g., blue and white) to help differentiate between the right and left side of the pelvic region to which the strap is to be secured. In some embodiments, the sleeves 26 associated with the straps 24 can be color-coded in a similar manner as described for the dilators 28. In some embodiments, both the sleeves 26 and the dilators 28 are color-coded.

In some embodiments, a leader 30 is coupled to a distal end of the dilator 28 and/or sleeve 26, and a trocar needle 32 is coupled to a distal end of the leader 30. The leader 30 can be a suture, formed, for example, with a polymer. In other embodiments, the leader 30 can be made from metal or other fiber and can be attached at one or more locations of a sleeve 26 and/or dilator 28. For example, the leader 30 can be coupled to the dilator 30 and/or sleeve 26 by, for example, gluing, thermo-bonding, knotting or other methods of attachment. In some embodiments, the leader 30 can be a portion of (or formed monolithically with) a suture used to couple the sleeve 26 to a strap 24. Although only one leader 30 and trocar needle 32 are illustrated in FIG. 1, it should be understood that a leader 30 and trocar needle 32 can be coupled to each of the dilators 28 and/or sleeves 26 of an implant 20.

The trocar needle 32 can be formed with various biocompatible materials, such as, for example, stainless steel, or other surgical steel. The trocar needle 32 can be used to associate the a strap of the implant to a delivery device, such as, for example, a Capio® Suture Capture Device manufactured by Boston Scientific Corporation (also referred to herein as "BSC"). An example of such a suturing device is also described in U.S. Pat. No. 5,741,277, the disclosure of which is hereby incorporated by reference in its entirety. Other types of delivery devices can alternatively be used, such as, for example, the suturing device described in U.S. Patent Pub. 2004/0181243 A1 to Chu et al., entitled Reshapeable Medical Device, the disclosure of which is hereby incorporated by reference in its entirety. A similar delivery device is also described below with reference to FIG. 7.

A length of the leader 30 (measured from a distal end of the dilator 28) can vary. For example, in some embodiments, a length of a leader 30 is sufficiently long to be placed through a selected tissue anchoring site (after entering the pelvic region via a vaginal incision), and passed out through the vaginal incision, without requiring the dilator 28 to enter the vagina (e.g., after passing through a tissue within the pelvis). In some embodiments, a length of the leader 30 can allow the physician to remove the trocar needle 32 from a delivery device external to the body before an attached dilator 28 is pulled into the tissue or ligament. More details on the insertion and delivery of an implant using a delivery device is described below with reference to specific embodiments.

In other embodiments, rather than a leader 30 and trocar 32, the dilator 28 or sleeve 26 can include a connector portion that can be used to associate the straps 24 to a delivery device. For example, the dilator 28 or sleeve 26 can include a connector portion (not shown), or a separate connector (not shown) can be coupled to the dilator 28 or sleeve 26 that can be used to associate the strap 24 to a delivery device. In some embodiments, a loop connector is coupled to the sleeve 26 or dilator 28. Such a connector or connector portion can be used to associate the dilator 28 or sleeve 26 to a delivery device, such as, for example, an Obtryx® Halo, Curve, Advantage® or Lynx® device each manufactured by Boston Scientific Corporation. An example of such a device is also described in U.S. Patent Pub. No. 2005/0075660 and U.S. Patent Pub. No. 2005/0177022, the entire disclosures of which are hereby incorporated by reference in their entirety. Such a delivery device can create a path or passageway through, for example, an obturator muscle or membrane (e.g., using a transobturator approach) or through, for example, an arcus tendineus (e.g., using a transglutual approach). For example, the needle of the delivery device can be passed through an exterior incision and into the vagina, where it can be coupled to a strap of an implant assembly 20 (as described in more detail herein). The delivery device can be used to draw a strap or portion of the implant 20 through a passageway formed by the delivery device and through the exterior entry site in an inside-out approach. An example of such a delivery device is also described herein with reference to FIG. 11. A dilator can also be configured to be associated to other types of delivery devices, such as, for example, a delivery device as described in U.S. Provisional Application No. 60/981,159 filed Oct. 19, 2007, entitled "Apparatus For Placing Medical Implants," the disclosure of which is hereby incorporated by reference in its entirety.

The implant 20 can also be configured to be associated to other delivery devices not specifically shown herein. In some embodiments, a strap 24 of the implant 20 itself is configured to be associated to a delivery device. For example, a connector can be coupled directly to a strap 24 for association to a delivery device, or the strap can include, for example, an opening or hole configured to associate the strap 24 to a delivery device. In some embodiments, a leader 30 and trocar 32 can be coupled directly to a strap 24.

Delivery devices as described above can be used to deliver selected straps of the implant 20 to or through a pelvic tissue, such as, for example, a levator muscle (e.g., levator ani muscle), a sacrospinous ligament, a tendineus arch of levator muscle (also referred to herein as "arcus tendineus" or "white line"), obturator muscles, or to an iliococcygeus muscle, or to other anatomical securement sites within the pelvic region of a patient. The delivery device can also be used to pass a suture end through a wall of a vagina or to pass a suture through the epithelium of a vaginal wall without passing the suture through the vaginal wall. For example, straps 24 of the implant 20 can be deposited at selected tissue sites within the pelvic region and a portion of an implant 20 can also be coupled to a vagina of the patient, such as to the vaginal apex, to a wall of the vagina, secured inside the vagina (e.g., within a vaginal lumen) or within the pelvic region.

In some embodiments, only one implant 20 is implanted within a pelvic region. In other embodiments, more than one implant 20 are implanted. For example, a first implant can be placed posteriorly and be secured to a sacrospinous ligament, and a second implant can be placed anteriorly and secured to an arcus tendineus to support, for example, a bladder neck of a patient. In another example, a first implant can be secured on one side of a pelvic region of a patient, and a second implant can be secured on a contra lateral side of the pelvic region. In some embodiments, the implant 20 is sized to extend from a posterior region to an anterior region of a pelvic region of a patient. In yet other embodiments, the implant 20 is sized to extend from one side of the pelvic region to the other side of the pelvic region, or to span a substantial portion of the pelvic floor, such as in total pelvic floor repair implants.

The implant 20 can be used in its entirety, or alternatively, the implant 20 can be split into two or more portions. For example, an implant 20 can be cut into two portions, such as a posterior portion and an anterior portion. Each portion can then be used to treat a specific prolapse condition. In some embodiments, an implant 20 can be trimmed in width W and/or length L, before or during placement, to accommodate for different-sized pelvic regions. Thus, an implant 20 can be modified or customized by the user, for example by cutting. In other embodiments, an implant 20 can have more than two support portions. For example, an implant 20 can include multiple support portions 22 that are spaced at a distance from each other.

An implant 20 can be delivered or implanted into a pelvic region using a variety of different approaches, including for example, a transvaginal approach, a retropubic approach (e.g., the implant is placed through a vaginal incision and the anterior straps of the implant (see e.g., anterior straps 134 in FIG. 2) can then be placed by a supra pubic approach, or a transobturator approach). In one example, an implant 20 can be delivered using a transvaginal approach using for example, a Capio® device as described above. In such a procedure, the implant 20 is inserted through, for example, a single vaginal incision. The anterior straps of implant 20 can alternatively be implanted using a transobturator approach, using, for example, a delivery needle, such as an Obtryx® Curve or Obtryx® Halo as described above. In such a procedure, the implant 20 is inserted through a mid-line incision, through an obturator foramen and to a exterior incision. Such procedures are described in more detail below with reference to specific embodiments. An implant 20 (e.g., an incontinence implant having two straps) can alternatively be implanted using only a transobturator approach, using, for example, a delivery needle, such as an Obtryx® Curve or Halo as described above. In such a procedure, the implant 20 is inserted through a mid-line incision, through an obturator foramen and to an exterior incision. Such procedures are described in more detail below with reference to specific embodiments. In other procedures, the implant 20 is inserted through a mid-line incision, through an obturator foramen, but does not exit the skin.

Although the above-described embodiments describe securing a strap 24 to tissue without the use of a separate anchoring device (for example, securing with tangs of a strap), it should be understood that the implants described herein can also include anchors or other mechanical fasteners to secure one or more straps 24 to the pelvic tissue. For example, a suture can be used to secure a strap or other portion of an implant 20 to tissue, such as to a vaginal cuff. For example, the support portion 22 can be secured with a suture to a vaginal cuff for apical suspension. In another embodiment, an incontinence sling, or other types of pelvic floor implant can be used in conjunction with an implant 20.

Having described above various general principles, several exemplary embodiments of these concepts are now described. These embodiments are only examples, and many other configurations of an implant, sleeve assembly, or dilator assembly, etc., are contemplated.

FIGS. 2-6 illustrate an example of an embodiment of an implant. An implant 120 includes six straps, including two anterior straps 134, two mid straps 136, and two posterior straps 138. The implant 120 also includes a support portion 122 having an anterior support portion 144 between the anterior straps 134 and the mid straps 136, and a posterior support portion 146 extending between an end 125 of the implant 120 and the posterior straps 138. A center marking 139 is included along a centerline of the support portion 122 that can be used to help position the implant 120 in a desired location within a pelvic region of a patient.

In this embodiment, a length of each of the straps 134, 136, 138 is sufficient to secure the strap to its intended tissue securement site, but not long enough that the straps extend out of the vagina during delivery of the implant into the pelvic region using, for example, a transvaginal approach. Such a length of the straps eliminates or reduces the need for trimming large portions of the straps after placement and can also reduce clutter in the vagina and/or pelvic region during placement of the implant 120.

As best shown in FIGS. 3-5, the anterior straps 134 can also include textured surfaces. Specifically, in the illustrated embodiment the straps 134 include dimples 140 on a top and bottom surface of the anterior straps 134. As shown in FIG. 5, the dimples 140 are disposed in alternating, opposed directions on the top and bottom surfaces of the strap 134. The dimples 140 provide added gripping strength to engage surrounding tissue. The number of dimples 140 can vary and can also be included on other straps of the implant 120 and/or some or all of the support portion 122. The straps 134, 136, 138 can also include tangs as described above and/or can include barbs or other protrusions configured to engage tissue.

The dimples 140 can be tapered from their base to an end of the dimple 140. For example, the dimples 140 can be dome-shaped having a larger diameter at their base than a diameter at their tip or end. The dimples 140 can have a width (e.g., a diameter), for example, between about 0.02 cm (0.008 inches) and 0.04 cm (0.02 inches) at their tip and/or at their base. For example, a width of a dimple 140 can be about 0.36 cm (0.14 inches) at its base and narrow or taper to about 0.22 cm (0.087 inches) at an end or tip. Dimples 140 can have a length or height, for example, between about 0.15 cm (0.059 inches) and 0.23 cm (0.091 inches) and can be spaced apart from each other (e.g., from a centerline of one dimple to a center line of an other dimple) about 0.6 cm (0.2 inches). In some embodiments, dimples 140 can also be positioned such that they contact one another, overlap or are spaced at different distances from each other. In other embodiments, the dimples 140 may not be tapered.

The straps can include, for example, between 1 and 1000 dimples. Dimples 140 can be provided on any of the straps (134, 136, 138) and/or the support portions (144, 146) of an implant. Dimples 140 can be formed through heat stamping of the strap material. In other embodiments, dimples 140 or other surface textures can be created through other methods such as, for example, stamping, extruding, molding, or weaving.

Figure 2:
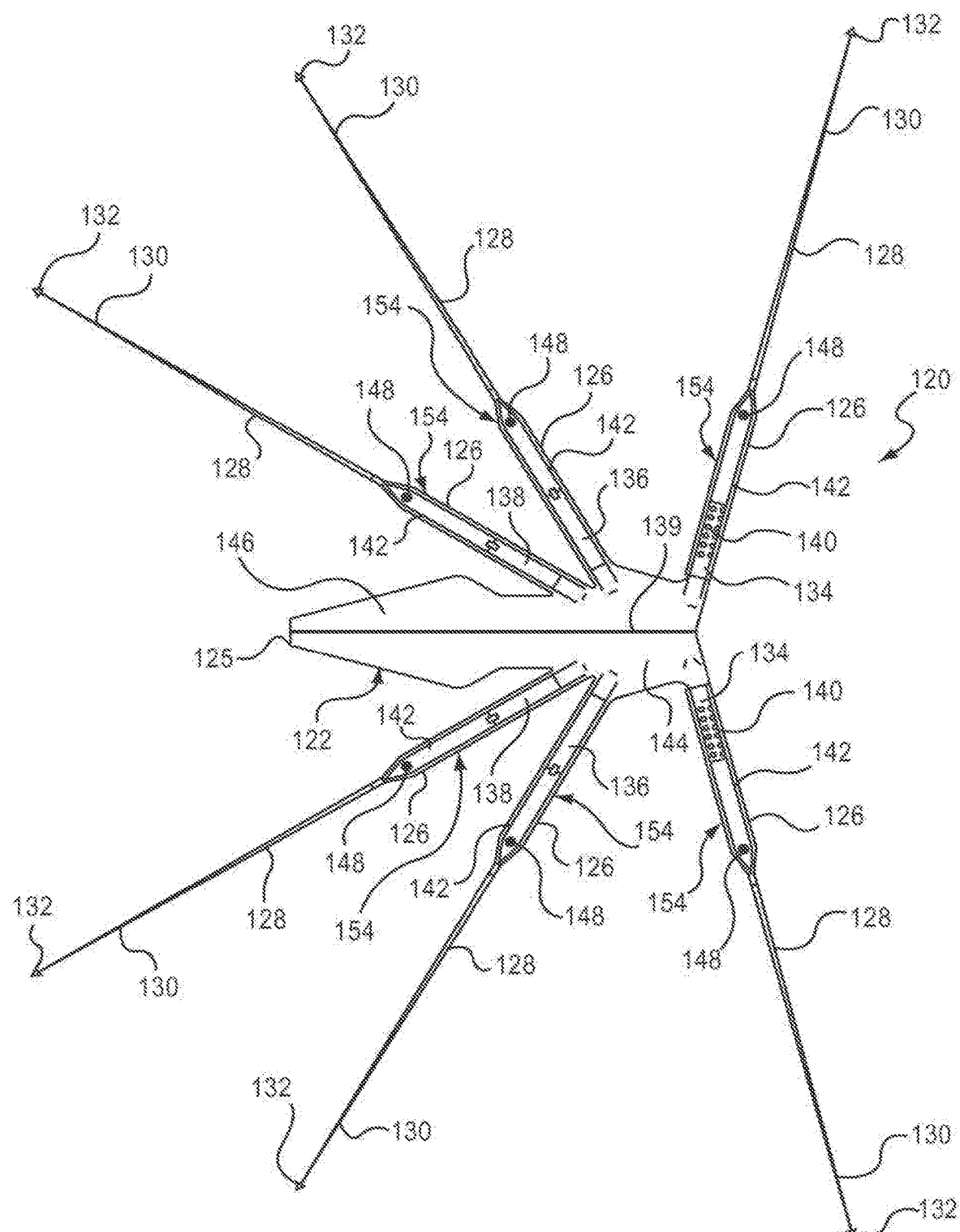
FIG. 2 is a top view of an embodiment of an implant.

A sleeve assembly 154 including a sleeve 126 and a tapered dilator 128 is disposed over each of the straps 134, 136, and 138 (shown in FIG. 2 only). The dilators 128 can be coupled to the sleeve 126 by, for example, crimping, heat sealing, stitching, stretching, tip tipping, etc. Alternatively, the sleeve 126 can be formed to include a portion that forms a tapered dilator. The dilator 128 can be used to expand or enlarge a passage during insertion through a tissue, to ease the transition to a cross-section or size of the sleeve 126. The sleeve 126 is also tapered, which also helps provide a lead-in through the tissue.

Figure 6:
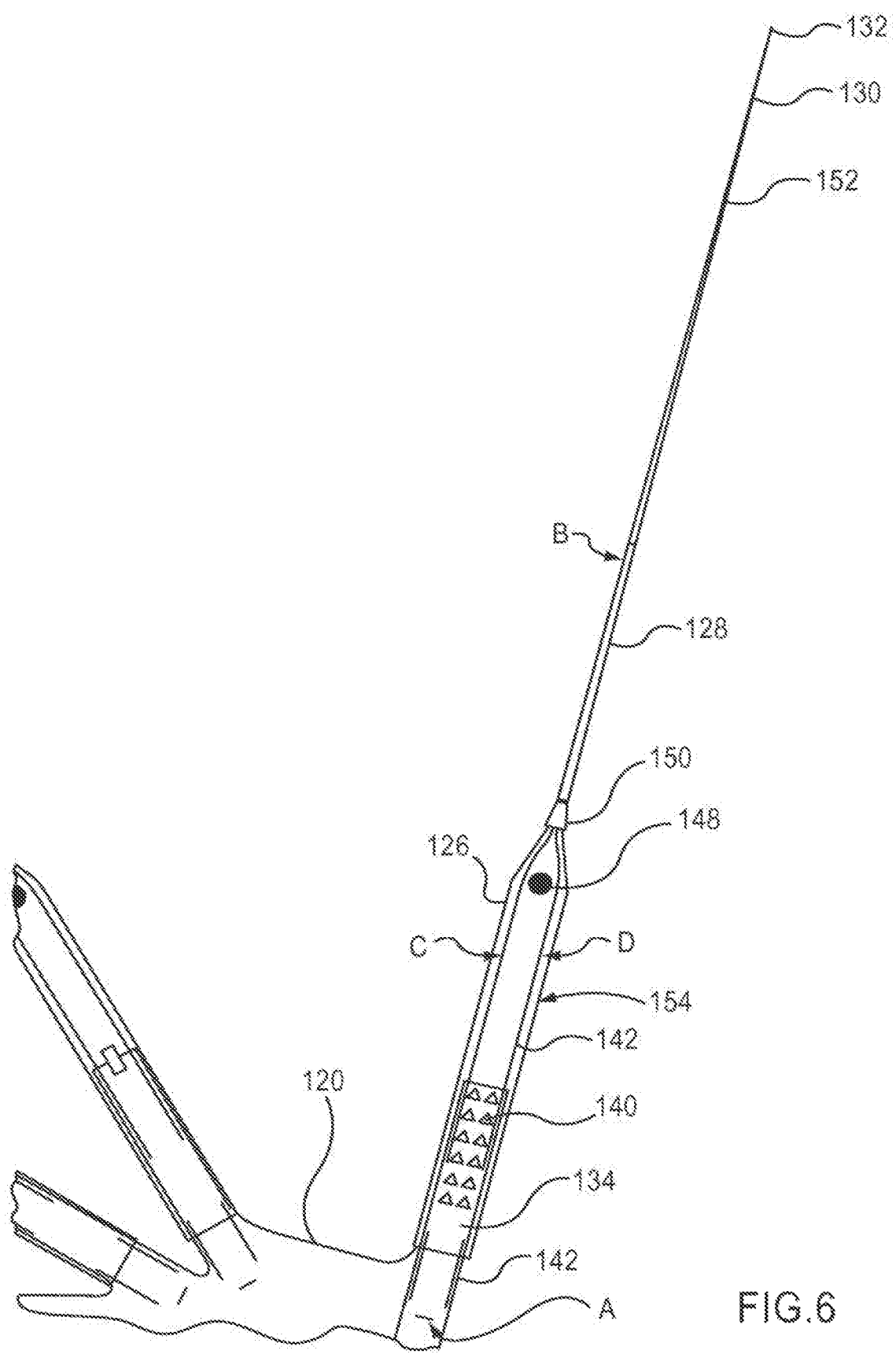
FIG. 6 is an enlarged top view of a portion of the implant of FIG. 2.

The sleeves 126 are secured to the straps with sutures 142. A suture 142 is looped through each of the straps 134, 136 and 138. In this embodiment, the sutures 142 are weaved or threaded through the straps 134, 136 and 138. For example, as shown in FIG. 6, the suture 142 is weaved through the strap 134 implant 120 at location A. Such a coupling of the suture 142 threaded through the straps 134, 136 and 138 can also help prevent strap stretch. The sutures 142 can alternatively be coupled to the straps 134, 136 and 138 using, for example, any of the methods described above for the dilator to sleeve coupling, for example, by crimping, heat sealing, stitching, stretching, tip tipping, etc. In some embodiments, a suture can be threaded to or secured to a strap, for example by knotting. The strands of the sutures 142 forming the loop through the sleeves 126 extend through an interior lumen (not shown) of the dilators 128 and are crimped closed and heat bonded to an interior wall of the dilators 128 at, for example, a location B shown in FIG. 6, to maintain the straps 134, 136 and 138 within the sleeves 126.

A leader suture 130 is coupled to and extends distally from each of the dilators 128. Alternatively, a leader portion of the sutures 142 can extend distally from the dilators 128. A trocar needle 132 is coupled to a distal end of each of the leader sutures 130. As described previously, the trocar needles 132 can be used to associate the implant 120 to a delivery device, such as a BSC Capio® device described above or a delivery device 164 described below.

The sleeves 126 each include a separator 148 disposed between two strands of the looped suture 142 and near a distal end of the sleeve 126, as best viewed in FIG. 6. The separator 148 maintains separation of the strands of the looped suture 142 within the sleeve 126. The separation of the strands of the suture 142 enable or help facilitate a cut to be made through only a single strand of the looped suture 142 at, for example, location C or D, during removal of the sleeve 126, as described in more detail below. In this embodiment, the separator 148 is a circular seal configuration, which can be formed, for example, by heat stamping two sides of the sleeve 126 together (or the use of tacks described below with reference to FIG. 65). Other types of separators can alternatively be used, such as for example, a separate component coupled within the sleeve 126, or an adhesive can be used to couple the two sides of the sleeve 126 together at a location between the strands.

The dilators 128 taper from a first diameter at a trailing end 150 to a second, smaller diameter at a leading end 152

(see FIG. 6). The first diameter can be, for example, between about 0.2 and 0.5 cm (0.08 to 0.2 inches) and the second diameter can be, for example, between about 0.03 to 0.2 cm (0.01 to 0.08 inches). For example, in some embodiments, the first diameter can be about 0.37 cm (0.15 inches) and the corresponding second diameter can be, 0.03 cm (0.01 inches). The dilators 128 can be formed, for example, by molding, extruding, casting, sintering, forging, machining, or other known methods of manufacturing such medical devices.

The implant 120 can be delivered into a pelvic region through a vaginal incision (e.g., a transvaginal approach). An incision can be made, for example, along an anterior vaginal mucosa. The incision can be, for example, 4 cm to 6 cm (1.57 to 2.36 inches) in length and can extend approximately 2 cm to 3 cm (0.79 inches to 1.18 inches) to the meatus. The vaginal epithelium is dissected from the underlying periurethral fascia toward the sacrospinous ligament. Specifically, the anterior vaginal wall is opened and the endopelvic connective tissue is separated from the pubic ramus at the level of the bladder neck to the ischial spine, exposing the paravesical and pararectal space. The sacrospinous ligament is identified and isolated through this defect. The anterior incision to place the implant 120 is about 4 cm long extending about 1 cm from the cervix to the level of the proximal urethra. The incision is also known to be an anterior corporaphy incision. Details of such a procedure are illustrated in FIGS. 66A-66D (described in more detail below). A posterior incision can also be made to gain access to place the posterior portion of the implant 120 (e.g., if the uterus has been removed). A posterior incision is made at the vagina apex and at a distal portion of the vagina. A subepithellial tunnel between the incisions is dissected of the posterior vaginal wall from the anterior rectal wall. Another type of posterior incision can also be made where excess tissue is excised as illustrated in FIGS. 67A-67F (described in more detail below). In some cases, where the uterus is removed, the incision can include a single continuous incision (combining an anterior and posterior incision). When the uterus is to be left intact, separate anterior and posterior implant and incisions can be used. Other types of incisions can be used to gain access to a pelvic region. Variations in the incisions can depend, for example, on the implant size, the needed repair or disease state to be treated, and/or the location of the intended placement of the implant.

Figure 7:
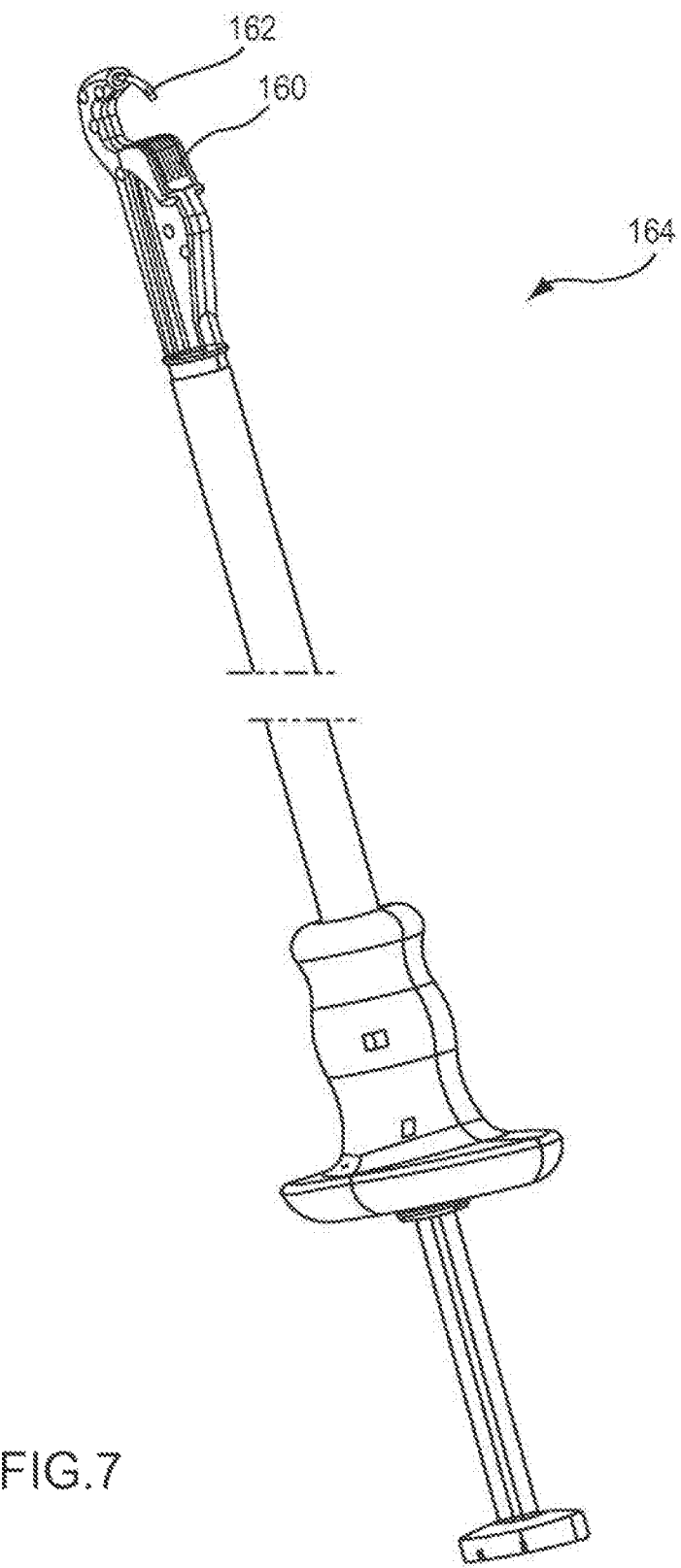
FIG. 7 is a side perspective view of a portion of a delivery device.

The various straps (e.g., 134, 136, 138) of the implant 120 can each be delivered through pelvic tissue using, for example, the suturing delivery device 164, as shown in FIG. 7. The trocar needle 132 on one of the straps (134, 136, 138) is loaded into the carrier 162 (shown partially extended in FIG. 7) of the delivery device 164. The delivery device 164 can then be used to pass the trocar needle 132 and the strap (with the sleeve assembly attached thereto) through a pelvic tissue. Specifically, the carrier 162 of the delivery device 164 is positioned adjacent a selected tissue site and the carrier 162 is actuated such that the trocar needle 132 pierces through the tissue. The trocar needle 132 and a distal end of the leader suture 130 are caught or retrieved by a catch 160 of the delivery device 164 after passing through the tissue. The delivery device 164 is then removed through the vagina, and the trocar needle 132 is removed from the catch 160. The sleeve assembly 154 is pulled through the tissue. For example, the user can pull the leader 130 or the dilator 128 through the tissue such that the strap is disposed within the tissue. This procedure is then repeated for other sleeve assemblies coupled to the other straps of the implant 120. Each strap of the implant is pulled through a selected tissue site and the straps are adjusted to position and tension the anterior support portion 144. Each strap can be delivered sequentially using the same delivery device, or separate delivery devices can be used for some or all of the straps. The straps 134, 136 and 138 (with sleeve assemblies 154 still attached) can be tensioned using visual guidance as the user observes the positioning of the support portion 122 for the correct tension through the vaginal incision.

After each strap (with sleeve assembly attached thereto) has been placed through a selected tissue site and adjusted as described above, the sleeve 126 and dilator 128 can be removed from the implant 120. For example, as shown in FIG. 6, to remove the sleeve 126 and dilator 128 from strap 134, a portion of the sleeve 126 and one strand of the loop of the suture 142 within the sleeve 126 can be cut, for example, at location C or D. Since the strap 134 is coupled to the sleeve 126 via the suture 142, cutting through a portion of the sleeve 126, and one strand of the loop of the suture 142, the sleeve 126 will be freely movable relative to the strap 134. The sleeve 126 (and dilator 128 coupled to the sleeve 126) can then be pulled off of the strap 134 by pulling on the sleeve 126 and the uncut strand of the suture 142. The cut suture 142 will also be free to pull through the strap 134. Thus, the suture 142 remains secured to the sleeve 126 and will simply unravel or unthread itself from the strap 134. With the sleeves 126 removed from the straps 134, 136, 138 tangs on the straps 134, 136, 138 can engage the surrounding tissue into which the strap 134, 136, 138 has been placed. The dimples 140 on the straps 134 can also engage surrounding tissue.

The posterior support portion 146 can be positioned around a vaginal cuff before or after removing the sleeves 126 from the straps 134, 136, 138. In some embodiments, a posterior vaginal incision is made to provide access for positioning the posterior support portion 146. For example, a physician can access the posterior support portion 146 via a posterior incision and using a hand can tuck or wrap the posterior support portion 146 around a vaginal cuff in a posterior region of the pelvis between the vagina and a rectum of a patient. The posterior support portion 146 can also optionally be secured to tissue or ligament within the pelvic region. For example, the posterior support portion can be sutured or stitched to a rectovaginal septum or a perineal body.

As stated above, the straps (134, 136, 138) can be secured within a pelvic region at various different tissue sites. For example, the anterior straps 134 of the implant 120 can be placed through, endopelvic fascia, or through tissue or ligaments near or in the pubococcygeus muscle, puborectalis muscle, distal tendineus arch of levator ani muscle or obturator internus or externus muscle, or obturator membrane or other tissue locations within a pelvic region. The mid-straps 136 can each be placed, for example, within a ischio-coccygeus muscle, an arcus tendineus or obturator muscle or membrane. The posterior straps can be placed, for example, in a sacrospinous ligament or coccygeus muscle.

The order in which the straps (134, 136, 138) are placed can vary. In one example order of delivering the straps, first the posterior straps 138 are delivered on each side of the pelvic region, and placed within, for example, sacrospinous ligaments. Then the mid straps 136 are delivered and placed within an arcus tendineus, and lastly the anterior straps 134 are delivered and placed within either the arcus tendineus or an obturator (e.g., obturator muscle or membrane). The location of a dilator 128 during the delivery process can be used to distinctively identify which dilator 128 has been passed through which tissue (e.g., arcus tendineus, obturator). For example, a location of a dilator exiting a vaginal anterior incision relative to the vagina (e.g., along a side, near the top, or near the bottom) can help indicate which tissue securement site corresponds to which dilator. For example, a dilator extending from a side of the vagina can indicate that the dilator was placed through the patient's arcus tendineus.

The order of tensioning of the straps can also vary. In some embodiments, the anterior straps 134 can be tensioned first, then the mid straps 136, and lastly the posterior straps 138. The anterior straps 134 can be used to position the anterior support portion 144 longitudinally and laterally. The mid straps 136 can be used, for example, to adjust and position the posterior support portion 148. The posterior straps 138 can provide a "deeper" anchor point and a proper angle for vaginal support.

In some medical procedures, the implant 120 can be cut into two separate portions such as an anterior and a posterior portion. One or both of the portions can then be implanted depending on the particular condition being treated. The implant 120 can also optionally be cut to form a different shape or size. For example, in a patient having a uterus, an implant having a posterior support portion and an anterior support portion can be cut into two portions. The length and/or width of each of the straps can also be modified. For example, in some embodiments, it may be desirable to cut off or otherwise remove one or more of the straps. For example, a physician may elect to cut off the anterior straps and secure an anterior portion of the implant to pelvic fascia using sutures.

Figure 8:
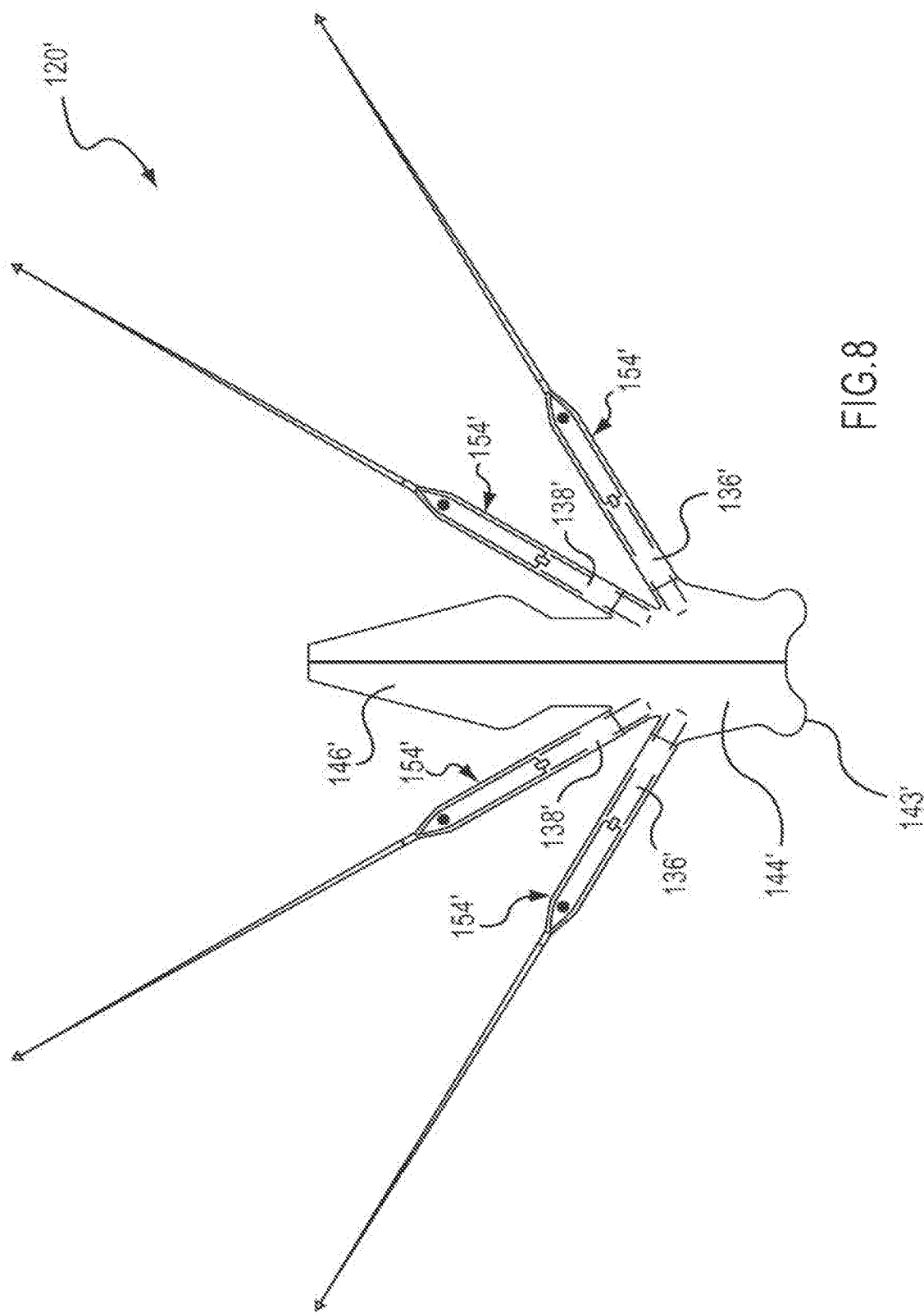
FIG. 8 is a top view of another embodiment of an anterior implant.

FIG. 8 illustrates an implant 120' that is similar to the implant 120. The implant 120' includes only four straps, including two mid straps 136' and two posterior straps 138'. A sleeve assembly 154' is coupled to each of the straps 136' and 138'. The sleeve assemblies 154' are constructed the same as the sleeve assemblies 154 described above. The implant 120' also includes an anterior support portion 144' and a posterior support portion 146'. In this embodiment, the anterior support portion 144' includes a pair of shoulders 143' that can be anchored to a tissue, such as for example, a levator muscle, an obturator, or an arcus tendineus. The shoulders 143' can be secured to such tissue, for example, with sutures. As with the implant 120, the straps 136', 138' can also include tangs as described above and/or can include barbs or other protrusions configured to engage tissue. The implant 120' can be placed through an anterior incision, the support portion 146' can be cut off and not used when a uterus is present. When there is no uterus present, the posterior support portion 146' (and also support portion 146 of implant 120) can be tucked though a posterior blunt dissection through the anterior dissection or through an additional posterior incision. The straps 136' and 138' can be delivered and anchored to tissue in the same manner as described above for implant 120. For example, the posterior straps 138' can each be secured to a sacrospinous ligament (on opposite sides of a pelvis) and the mid straps 136' can each be secured to an arcus tendineus (on opposite sides of a pelvis). The posterior support portion 146' can be wrapped around a vaginal cuff. For example, a physician can access the posterior area via an anterior or posterior vaginal incision to then pulled or tuck the posterior support portion 146' into a desired position.

Various components of the implants 120 and 120' can vary as described herein. For example, other configurations of the sleeve, dilator, suture, leader, etc. can alternatively be coupled to the straps of the implants 120 or 120' to aid in the delivery procedure. For example, a sleeve or dilator assembly that can associate the implant 120 or implant 120' to a type of delivery device not described herein can alternatively be used.

Figure 9:
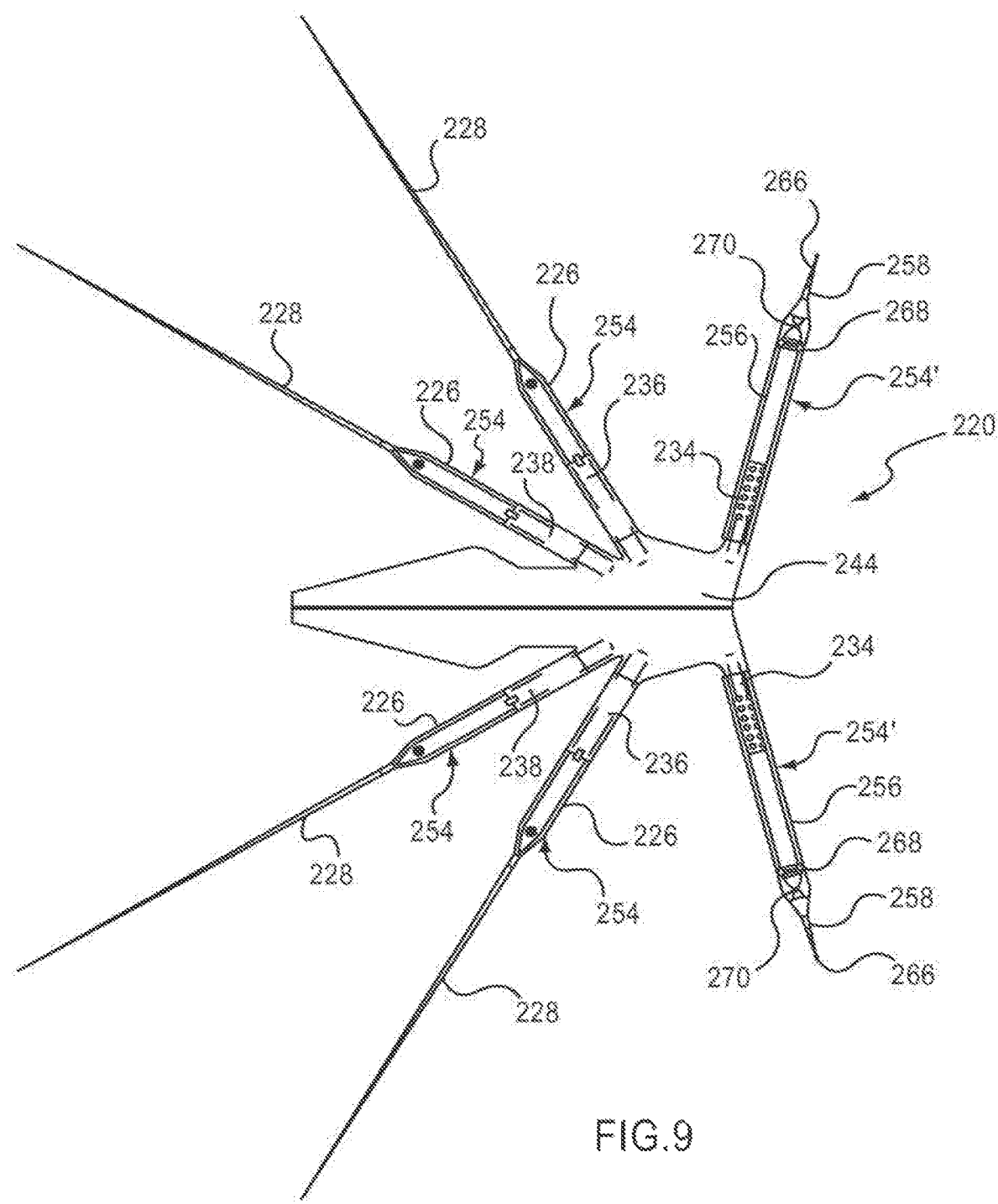
FIG. 9 is a top view of another embodiment of an implant.
Figure 10:
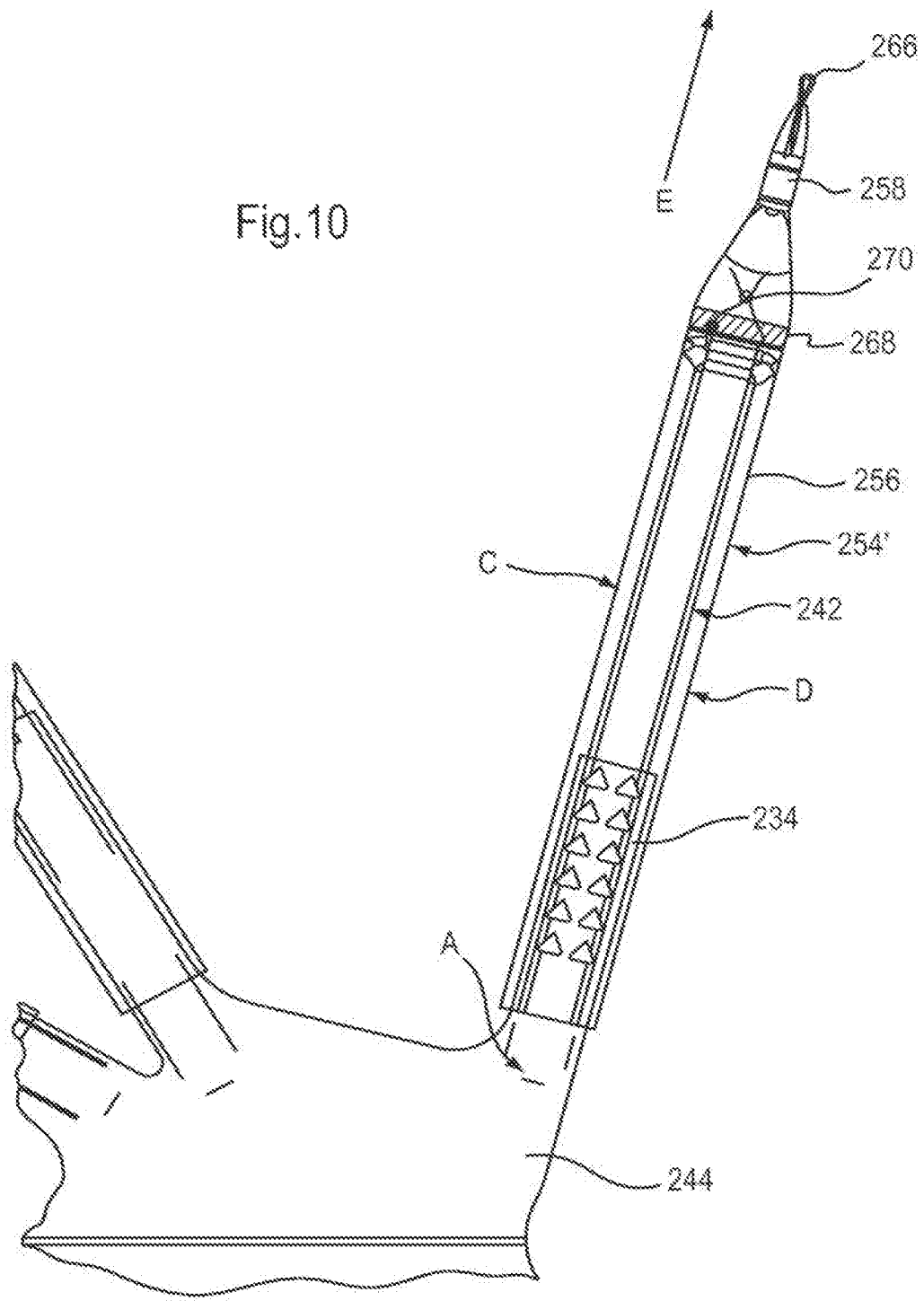
FIG. 10 is a top view of a portion of the implant of FIG. 9.

FIGS. 9 and 10 illustrate another embodiment of an implant that is similar to the implant 120. In this embodiment, an implant 220 includes anterior straps 234, mid straps 236, and posterior straps 238. The implant 220 includes removable sleeve assemblies 254 having sleeves 226 and dilators 228, disposed over the mid-straps 236 and the posterior straps 238. The sleeve assemblies 254 have the same configuration as the sleeve assemblies 154 and 154' such that the straps 236 and 238 can be delivered using a suturing device (e.g., a delivery device 164) in the same manner as described above.

This embodiment differs from the previous embodiment in that the implant 220 includes a sleeve assembly 254' disposed over each of the anterior straps 234. The sleeve assemblies 254' include a sleeve 256, dilators 258 coupled to the sleeves 256, and loop connectors 266 coupled to the dilators 258. The anterior straps 234 are secured to the sleeves 256 with a suture 242 in a similar manner as described above for the previous embodiment. As best shown in FIG. 10, the sutures 242 are looped through the straps 234 and through a portion of an anterior support portion 244 at location A. The sutures 242 are secured to the sleeves 256 with a heat seal 268 applied across each of the sleeves 256. The heat seals 268 can maintain the position of the suture 242 and help prevent the strands of the suture 242 from coming together within the sleeves 256 (e.g., keeps the strands separated from each other). Thus, an additional separator portion or member (e.g., separator 148 in the previous embodiment) is not necessary to separate the strands of the suture 242. The sutures 242 can be further secured to the sleeves 256 by forming a knot 270 with the suture 242 on a distal side of the heat seals 268. The knots 270 are sufficiently large to prevent migration of the suture 242 past the heat seals 268. In other embodiments a knot 270 is not used, rather, the suture 242 is heat bonded directly to the sleeve 256 to prevent movement of the suture 242.

The anterior straps 234 can have a length, such that the straps 234 will not exit the skin at either side of the patient when pulled through a needle passageway as described below. When the sleeve assembly 254 and strap 234 are pulled through a tissue, a tension force can be transferred from the sleeve 256 to the suture 242 via the heat seals 268, then to the anterior support portion 244. This prevents the strap 234 from stretching within the sleeve 256 and maintains a uniform strap width to maximize its holding strength during delivery. The heat seals 268 can also help prevent the strap from inadvertently separating from the sleeve 256 during delivery of the strap 234 through a tissue.

The loop connector 266 can be, for example, a portion of a leader (e.g., suture) that extends from a distal end of the dilator 266. In other embodiments, different types and configurations of the loop connector 266 can alternatively be used. The loop connector 266 can be used to associate a strap 234 to a delivery device, such as, a delivery device 264 shown in FIG. 11. The delivery device 264 can be, for example, an Obtryx® Curve device, an Obtryx® Halo device, a Curve, or a Lynx® device all manufactured by Boston Scientific Corporation as described above.

Figure 11:
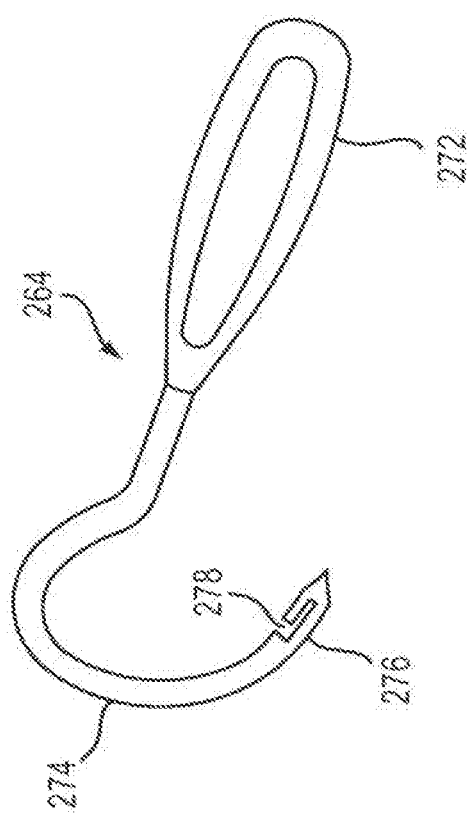
FIG. 11 is a side view of another embodiment of a delivery device.

The delivery device 264 includes a handle 272, a curved shaft or needle 274, and a connector end 276. The connector end 276 defines a notch 278 that is configured to receive the loop connector 264. Although the delivery device 264 is shown having a curved needle 274, in other embodiments, the needle is substantially straight, angled or curved at a different radius of curvature than as shown in FIG. 11. The delivery device 264 can be used, for example, to deliver the anterior straps 234 of the implant 220 as described in more detail below. It should be understood that the delivery device 264 is merely an example of the type of delivery device that can be used to deliver the strap 234 to a desired location within a pelvic region of a patient. For example, in some embodiments, a tube shaped connector is coupled to the distal end of the elongate body of the dilator to associate the dilator to a delivery device such as those used in the Advantage® or Prefyx™ systems manufactured by Boston Scientific Corporation. Such a device can be used, for example, to deliver a portion of an implant in a retro pubic or pre-pubic approach.

Using a delivery device, such as delivery device 264, the anterior straps 234 (with attached sleeve assemblies 254) can be passed through a desired tissue location within a pelvis. Such a procedure can include inserting the delivery device needle 274 through an exterior incision and then through, for example, an obturator foramen and to a mid-line incision in a vagina using an outside-in approach. The loop connector 266 of the sleeve assembly 254 is associated to the notch 278 of the delivery device 264. The sleeve assembly 254 is then pulled back through the path formed by the insertion of the curved needle 274 until the needle 274 exits the patient's body. This procedure can then be repeated on the contra lateral side of the pelvic region. The straps 234 can be tensioned using visual guidance as the user observes the positioning of the support portion 244 of the implant 220 through the vaginal incision.

After pulling the sleeve assembly 254 (and strap 234) through a tissue (e.g. using the delivery device 264), the sleeve assembly 254 can be removed from the strap 234 in a similar manner as described for the previous embodiment. For example, a portion of the sleeve 256 and a strand of the suture 242 are cut, for example, at a location C or D, as indicated in FIG. 10. The heat seal 268 maintains the strands of the suture 242 apart from each other to facilitate cutting only one strand of the suture 242. The cut sleeve assembly 254 is then pulled in a direction of arrow E, which releases the sleeve 256 from the strap 234 and allows the suture 242 to unravel or unthread from the strap 234. The sleeve assembly 254 can alternatively be released from the strap 234 by cutting all the way through the sleeve 256 and suture 242 at, for example location C or D. In such a case, pieces of the sleeve assembly 254 and remaining portions of suture 242 can be manually removed.

After all straps (234, 236, 238) are tensioned, and the sleeve assemblies 237, 254 are removed, additional trimming of the straps may be unnecessary due to the length of the straps as previously described. Although the procedure above described secured the anterior straps 234 using an inside-out approach, the delivery device 264 (and like devices, such as, e.g. a BSC Obtryx® delivery device) can be used in an "outside-in" approach similar to the delivery device 164. For example, the delivery device can be inserted through a vaginal incision and used to pass the strap 234 via the loop connector 266 through, a pelvic tissue, such as an obturator muscle or membrane.

Figure 12:
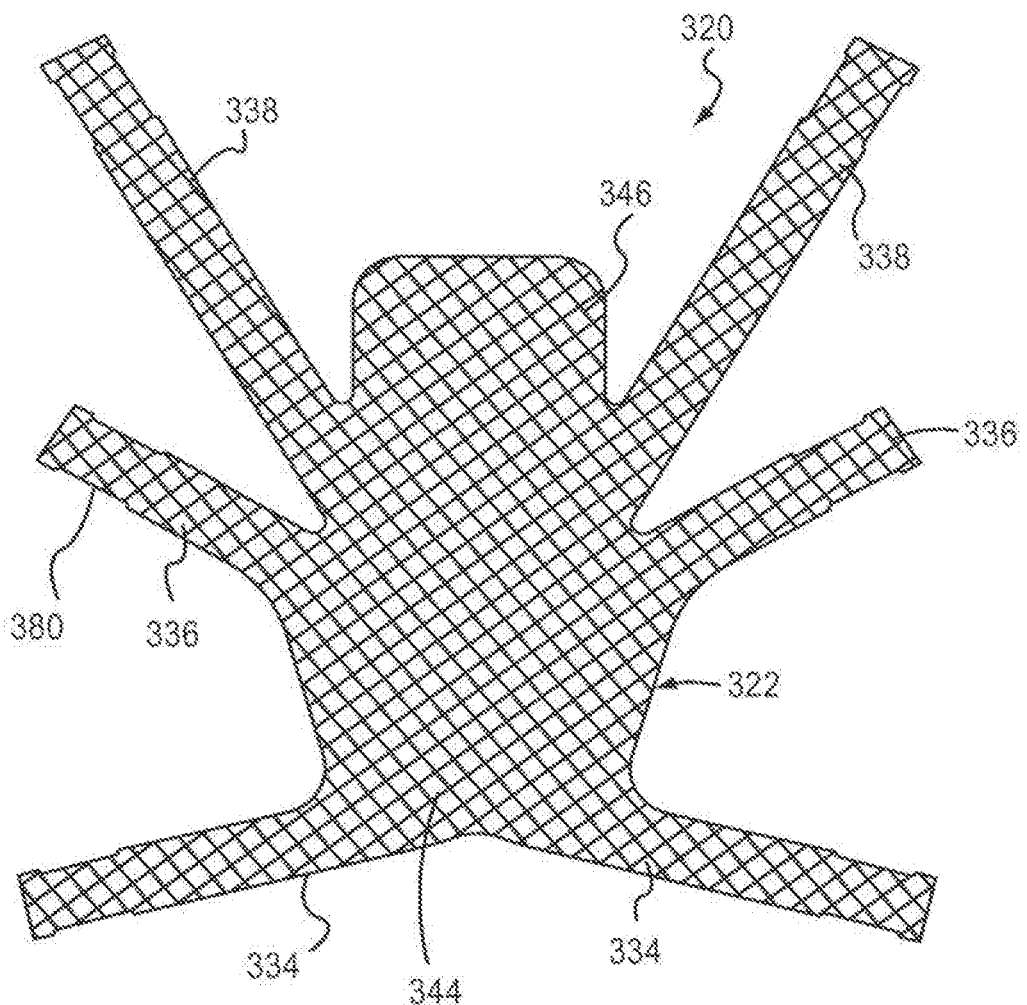
FIG. 12 is a top view of another embodiment of an implant.
Figure 13:
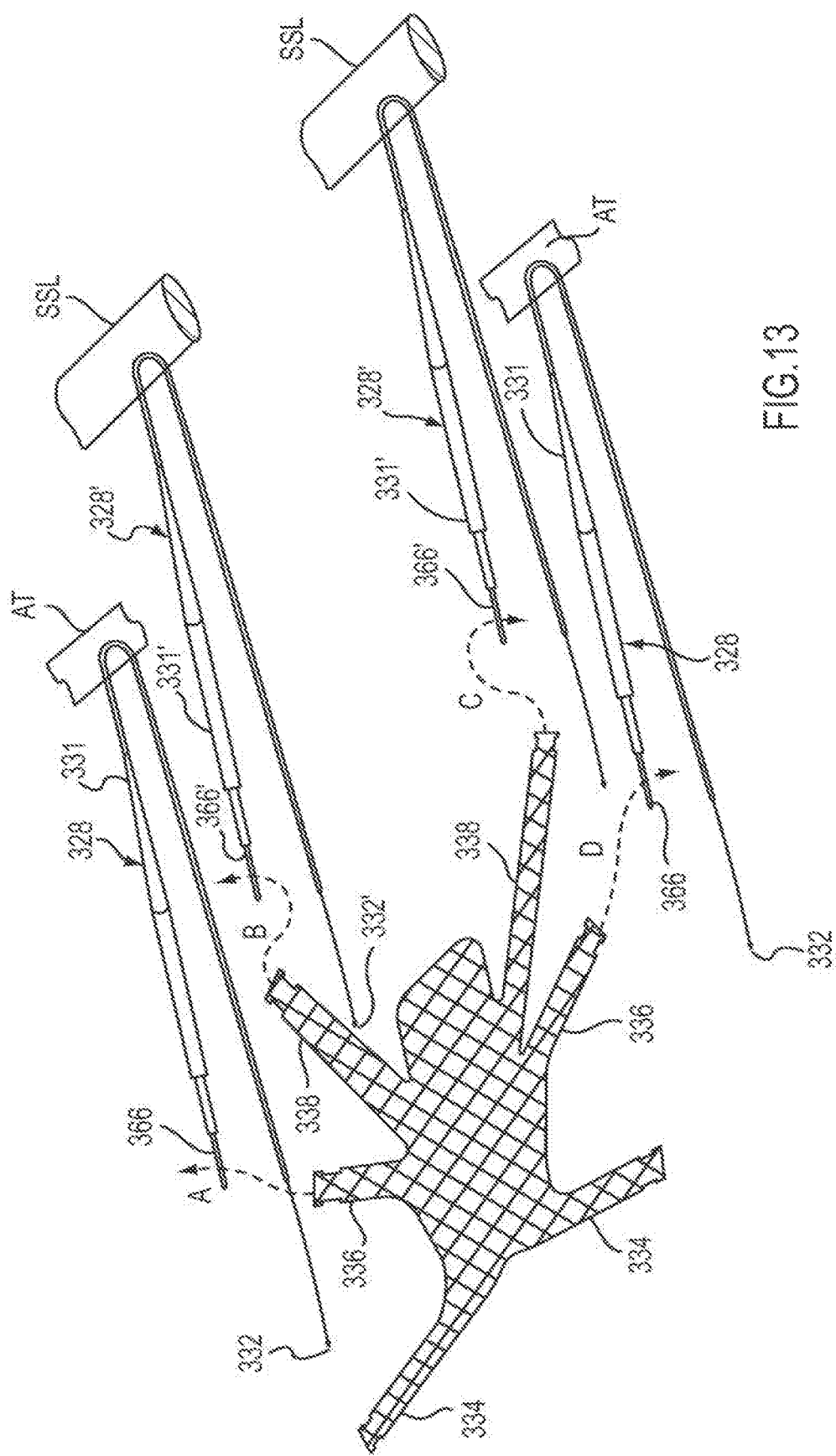
FIG. 13 is a side perspective view of four dilator devices and the implant of FIG. 12 shown disposed within a schematic illustration of portions of a pelvic region.

FIG. 12 illustrates another example of an implant. An implant 320 includes anterior straps 334, mid-line straps 336, posterior straps 338, a support portion 322 that includes an anterior support portion 344 and a posterior support portion 346. The implant 320 can be used, for example, for a cystocele repair and can be placed on an anterior side of a vagina. Each of the straps 334, 336, 338 can be associated to various configurations of sleeves, sleeve assemblies, and/or dilator devices for delivery of the straps to a pelvic region. In this embodiment, each of the straps 334, 336, 338 include a grooved or recessed portion 380 that has a smaller width than a remaining portion of the strap. The grooved portions 380 can indicate a location to associate the strap to a connector of a dilator and/or sleeve/dilator assembly. FIG. 13 illustrates four example dilator devices (also referred to as "dilator") labeled 328 and 328' that can be used to deliver the straps of the implant 320. Dilators 328 are each shown passed through a schematic representation of an arcus tendineus (AT). Dilator devices 328' are each shown passed through a schematic representation of a sacrospinous ligament (SSL). The dilators 328, 328' can be passed through the various tissue locations, for example, using a delivery device, such as delivery device 164 described herein by associating a trocar needle 332, 332' of the dilators 328, 328' to the delivery device.

The straps of implant 320 are configured to be associated to dilators 328, 328' after the dilators have been placed in the patient. For example, the dilator devices 328, 328' can be passed through tissue as previously described using a delivery device, such as delivery device 164. The various straps of the implant 320 can be associated to a selected dilator 328, 328' and then passed through the tissue using the dilator. For example, as shown in FIG. 13, the straps 336 can be placed through loop connectors 366 as indicated by the arrows A and D, and secured to the dilators 328 by moving or sliding a slidable tube member 331 of the dilators 328 towards and over the loop connectors 366 and the portion of the straps 336 within the loop connectors 366. The tube members 331 can frictionally hold the straps 336 to the loop connectors 366. The straps 338 of the implant 320 can be similarly secured to the dilators 328' by passing the straps 338 through loop connectors 366' as indicated by the arrows B and C and sliding slidable tube members 331'. The dilators 328, 328' can then be used to pull the respective straps through the sacrospinous ligaments and the arcus tendineus as indicated in FIG. 13. Although not shown in FIG. 13, the anterior straps 334 can be delivered into a pelvic region and through a tissue in a similar manner. For example, the straps 334 can be coupled to a dilator device and pulled through an obturator muscle or membrane using a delivery device, such as delivery device 164. In some embodiments, a connector can be coupled to the straps 334 such that the straps 334 can be delivered using a delivery device, such as delivery device 264 shown in FIG. 11.

Figure 14:
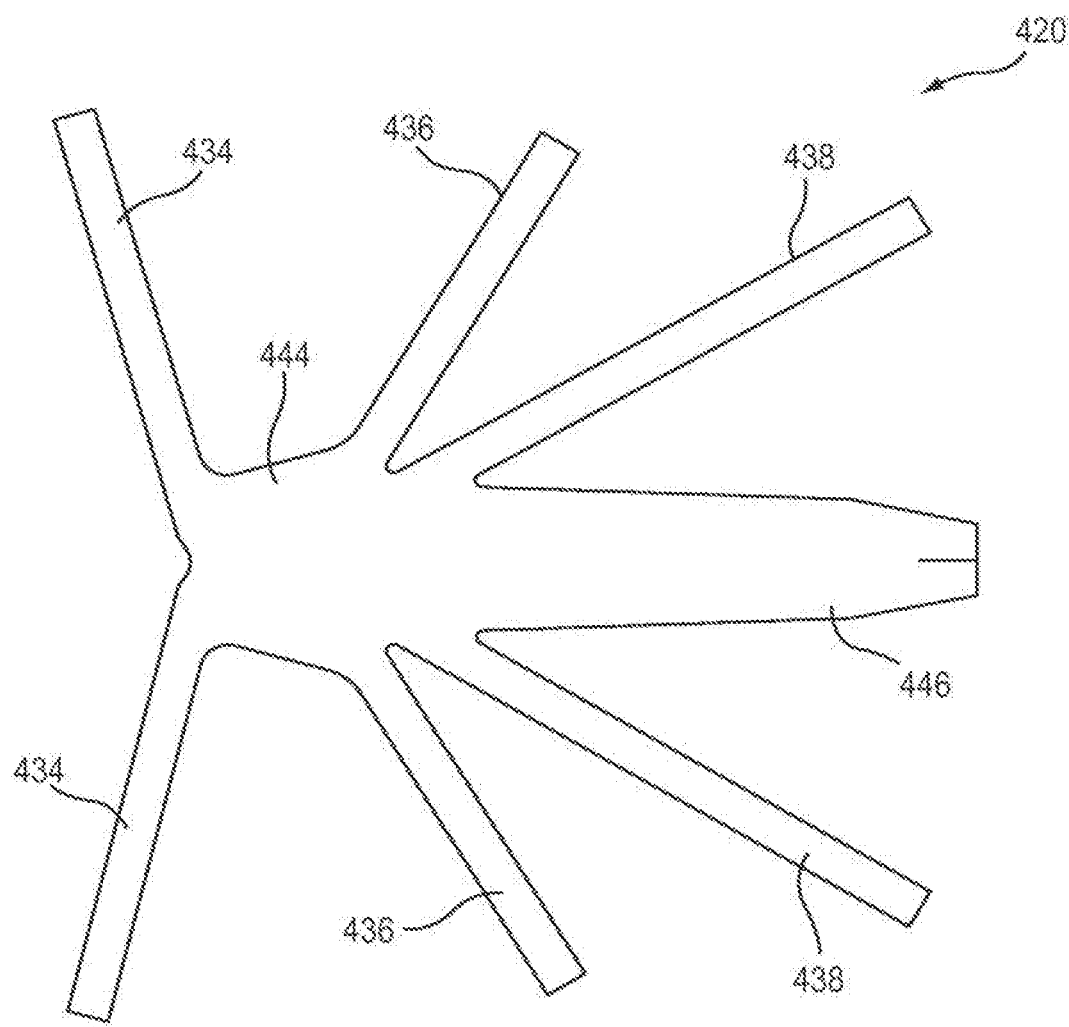
FIG. 14 is a top view of another embodiment of an implant.

FIG. 14 illustrates an embodiment of an implant that is similar to the implant 320 but the posterior support portion is extended to provide a posterior tail support. An implant 420 can be used, for example, for cystocele and rectocele repairs. The implant 420 includes anterior straps 434, mid-line straps 436, posterior straps 438, an anterior support portion 444 and a posterior support portion 446. Although not shown in FIG. 14, the implant 420 can be formed with a mesh material, and can include sleeve assemblies, sleeves and/or dilators as described herein to assist in the delivery of the straps to the pelvic region. For example, the implant 420 can be configured such that the straps 434, 436, 438 of the implant 420 can be delivered using a delivery device such as, for example, delivery device 164 and/or delivery device 264.

The posterior support portion 446 can be trimmed to a desired length for a customized fit. In some embodiments, the implant 420 can include a marking line (not shown in FIG. 14) along the implant to indicate where to trim the implant. The posterior support portion 446 can be trimmed, for example, to modify the implant 420 to have a posterior support portion substantially similar to implant 320 previously described. Such modification may be desired when only a cystocele repair is needed. When implanted into a patient's pelvic region, the posterior tail support 446 can be tucked into the posterior side of a vagina as described above with reference to implants 120 and 120'.

Figure 15:
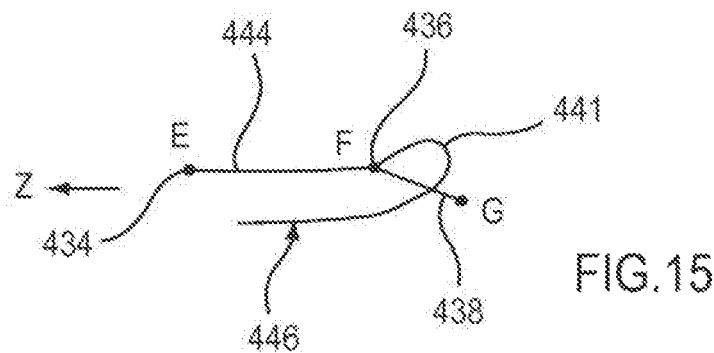
FIG. 15 is a side schematic illustration of the implant of FIG. 14 shown positioned in a pelvic region.

FIG. 15 is a schematic side view of the implant 420 after placement within a pelvic region. The point E represents the anterior strap 434 secured to an obturator membrane or muscle, the point F represents the mid-line straps 436 secured to an arcus tendineus, and point G represents the posterior straps 438 secured to a sacrospinous ligaments. The posterior support portion 446 is shown pulled in a direction of arrow Z, to customize a vaginal wrap 441 about a vaginal cuff.

Figure 16:
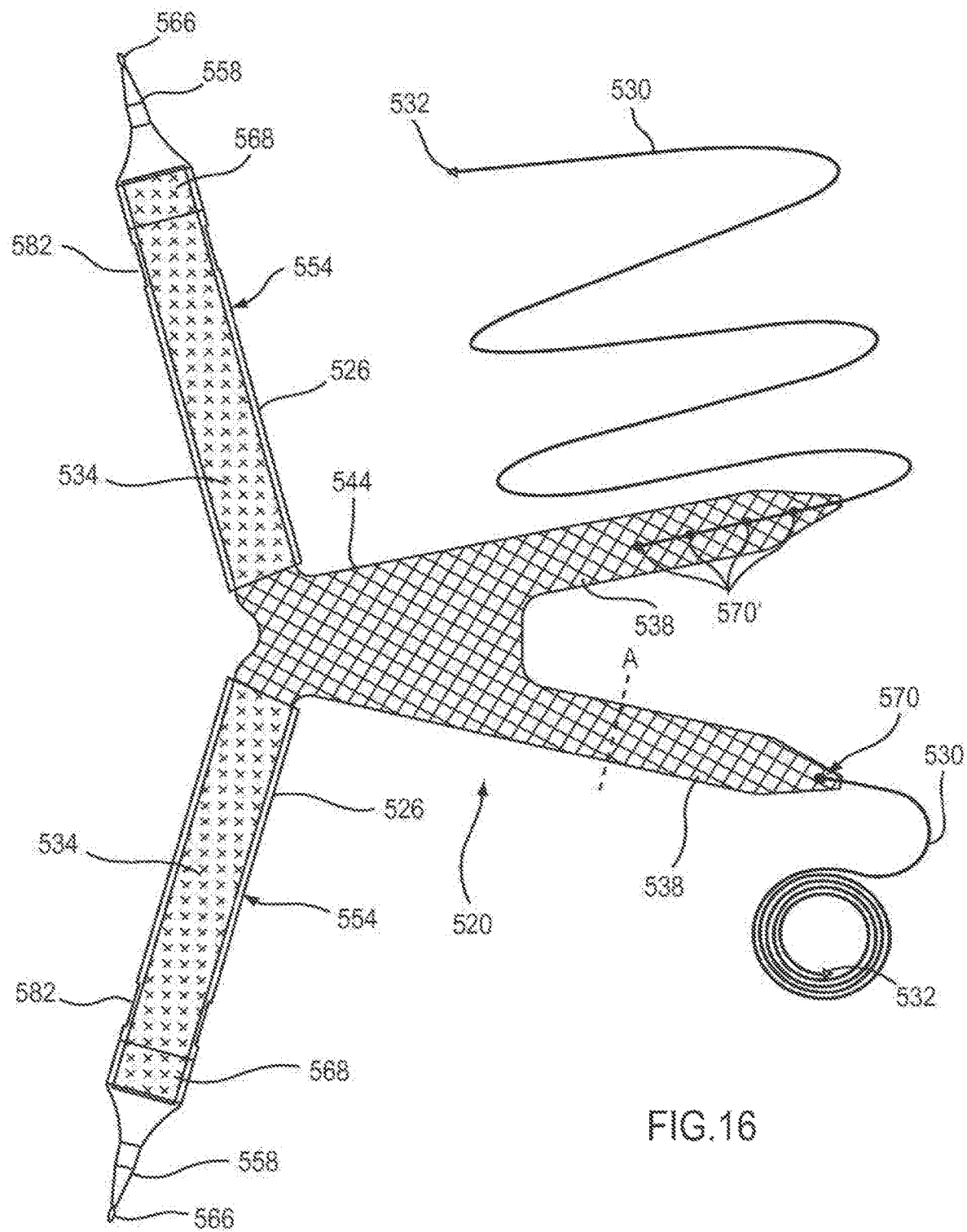
FIGS. 16-21 are each a top view of a different embodiment of an implant.

FIGS. 16-21 are each a different embodiment of an implant having four straps for fixation within a pelvic region. As shown in FIG. 16, an implant 520 includes anterior straps 534, posterior straps 538 and a support portion 544. Sleeve assemblies 554 are similar to sleeve assemblies 254' in FIG. 8 and are disposed over the straps 534. The sleeve assemblies 554 include sleeves 526, dilators 558 and connectors 566. The sleeves 526 can be made of a clear biocompatible polymer and include windows or openings 582. The anterior straps 534 can be coupled to the sleeves 526 by a heat seal 568. The windows 582 provide an access port for a cutting tool, such as scissors, to access and cut the strap 534, and optionally to cut at least one wall of the sleeve 526. As previously described, this allows the strap 534 to detach from the heat-sealed portion of the sleeve 526 for removal of the sleeve 526 after implantation of the implant 520.

As illustrated in FIG. 16, a leader suture 530 is coupled to each of the posterior straps 538 by knotting the leader suture 530 directly to the posterior strap 538. A single knot 570 or multiple knots 570' can be used. The posterior straps 538 are tapered to provide easier insertion through tissue. A trocar needle 532 is coupled to a distal end of each of the leader sutures 530. As described above, the trocar needles 532 can be used to associate the implant 520 to a delivery device, such as delivery device 164 (FIG. 7). The leader suture 530 and a portion of the strap 538 (if needed) can be trimmed and discarded after the implant 520 is placed in a desired location. In some embodiments, a substantial portion of the strap 538 can be cut off. For example, the strap 538 can be cut at location A. The posterior straps 538 can be secured, for example, to a sacrospinous ligament or a coccygeus muscle.

The anterior straps 534 can be placed within, for example, an arcus tendineus (white line), or an obturator membrane or muscle using any of the various approaches described herein. For example, the anterior straps 534 can be placed using a transobturator approach, a transvaginal retropubic approach, a suprapubic approach, or in front of a pubic bone. A delivery device, such as delivery device 264 (FIG. 11) can be used to deliver the straps 234 via connectors 566 as described above. Tangs (not illustrated) on edges of the straps 534, 538 can engage the surrounding tissue after being implanted, as described above.

Figure 17:
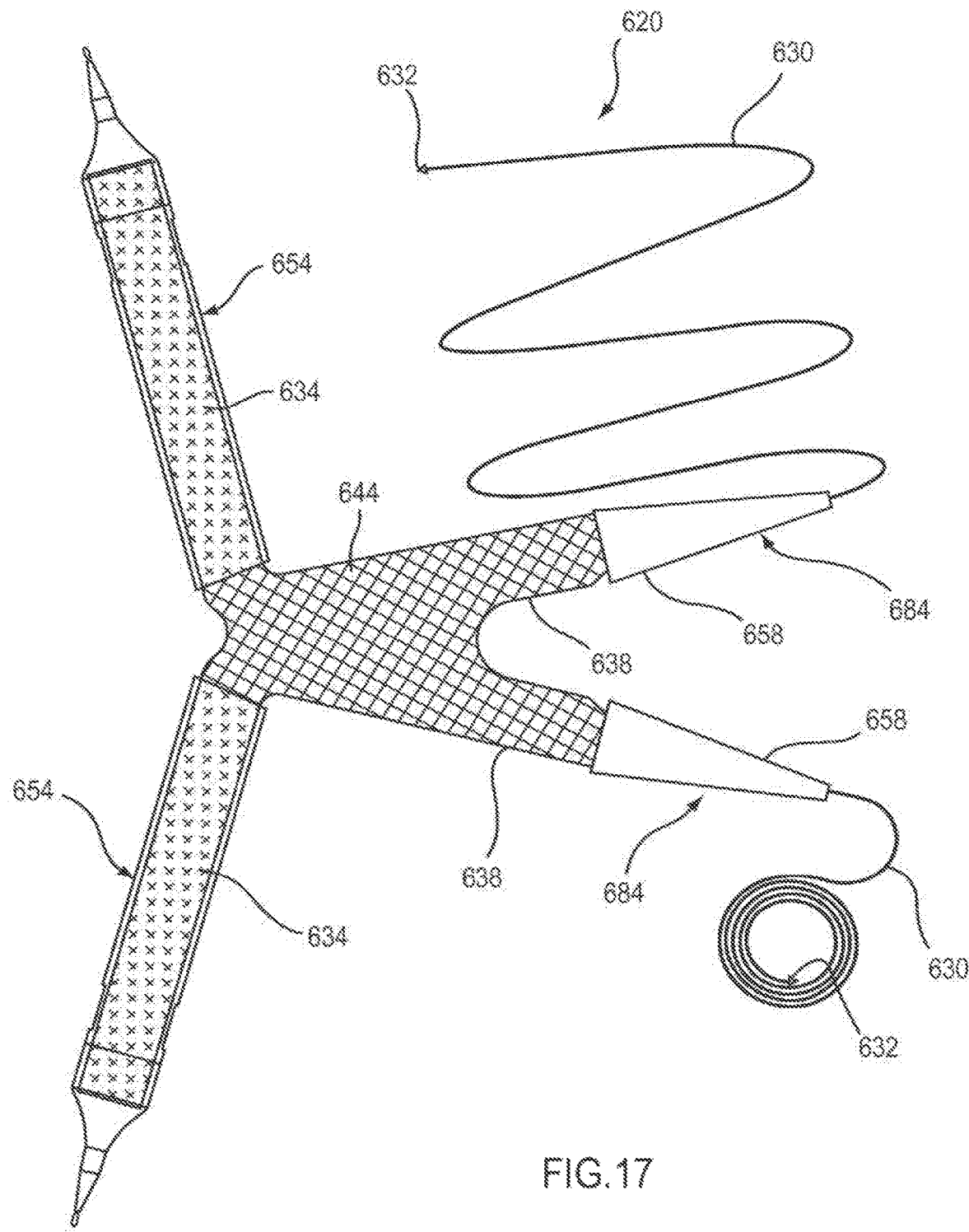

FIG. 17 illustrates an embodiment of an implant similar to the previous embodiment (implant 520), but in this embodiment the implant includes insertion aids. An implant 620 includes a support portion 644, anterior straps 634 and posterior straps 638. The anterior straps 634 and sleeve assemblies 654 are constructed the same as with the implant 520. The implant 620 includes an insertion aid 684 coupled to each of the posterior straps 638 to protect the straps 638 from damage and elongation during placement. In this embodiment, the insertion aids 684 include a dilator 658. The insertion aids 684 can be coupled to the straps 638 with a friction fit, with sutures, gluing, bonding, etc. The insertion aid 684 can help prevent the implant material (e.g., mesh) from cutting through muscle or ligaments when being pulled through such tissue during placement. The insertion aids 684 can also reduce the overall size (e.g., footprint) of the implant. For example, as described above (e.g., for implants 120, 120'), a length of the straps 638 can be shorter than a length of the insertion aids 684. The insertion aids 684 thus, can provide a longer effective length of the straps 638 to aid in pulling the straps 638 through tissue. A length of the insertion aids 684 can also vary.

A bullet trocar needle 632 is attached to a leading end of a leader suture 630 extending distally from each of the insertion aids 684 and can be used to associate each of the straps 638 to a delivery device (e.g., delivery device 164) as previously described. As with the previous embodiment (e.g., implant 520), the leader/dilator portions (630, 632, 684) and a portion of the strap 638 can be trimmed and discarded after the implant 620 is placed.

Figure 18:
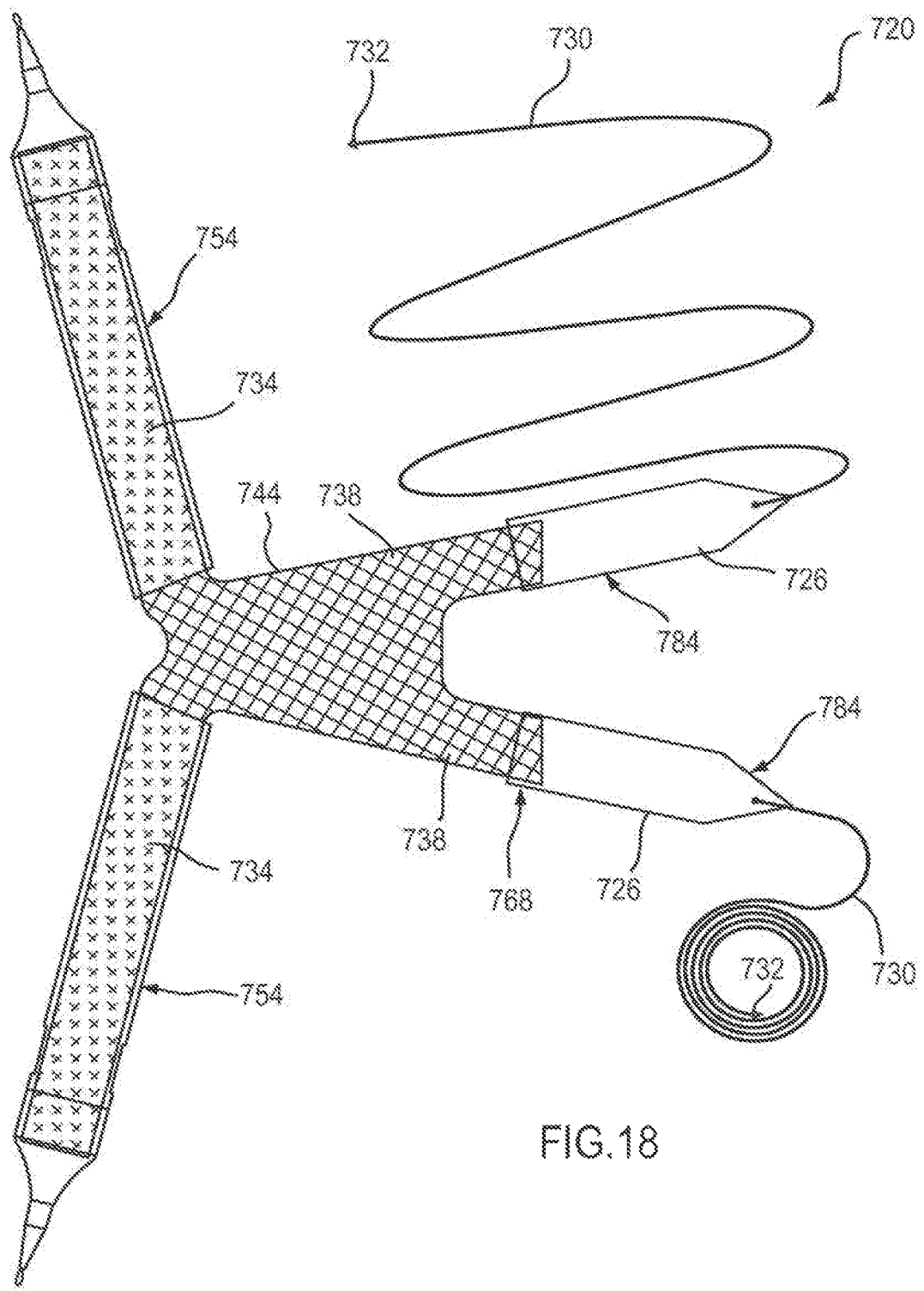

FIG. 18 illustrates another implant formed similar to the implant 620, but with insertion aids that include a sleeve. An implant 720 includes a support portion 744, anterior straps 734, posterior straps 738, and sleeve assemblies 754. The anterior straps 734 and sleeve assemblies 754 are constructed the same as the straps 634 and sleeve assemblies 654 described above. An insertion aid 784 includes a tapered sleeve 726 that is disposed over a portion of each of the posterior straps 738. The insertion aids 784 can be coupled to the posterior straps 738 with, for example, by applying a heat seal 768 to the sleeves 726. As with the previous embodiments, a leader suture 730 and trocar needle 732 are coupled to the sleeves 726 and used to associate the implant 720 to a delivery device.

Figure 19:
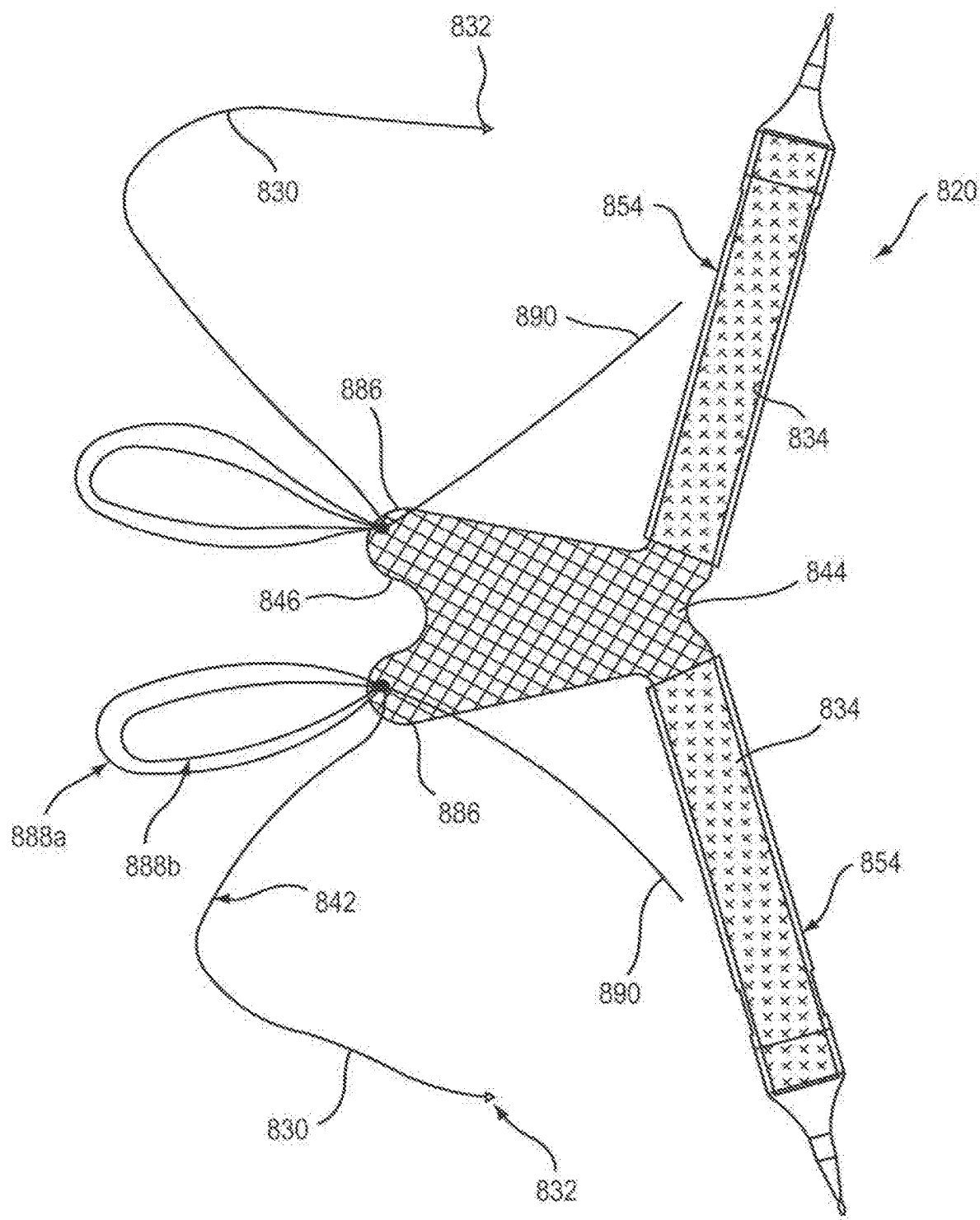

FIG. 19 illustrates an embodiment of an implant that is configured to abut to anchoring tissue at two points without the use of straps. An implant 820 includes a support portion 844, anterior straps 834, posterior straps 838 and sleeve assemblies 854. The anterior straps 834 and sleeve assemblies 854 are constructed the same as in the implants 520, 620 and 720. In this embodiment, the implant 820 includes a posterior support portion 846 that defines a pair of curved tabs or shoulders 886. A suture 842 is coupled to each of the curved tabs 886 with two nooses or loops 888*a* and 888*b*. The nooses 888*a* and 888*b* can be formed, for example, by threading or passing the suture 842 through the curved tabs 886 of the posterior support portion 846 two times without tightening the suture 842. A trocar needle 832 is coupled to an end of a leader portion 830 of the suture 842, and an end portion 890 of the suture 842 is left free.

To secure a curved tab 886 to a tissue, the trocar needle 832 is passed through the nooses 888*a* and 888*b*, and loaded onto a carrier of a delivery device (e.g., a delivery device 164). The delivery device is approximated to an anchoring tissue, and the carrier of the delivery device is activated to pass the trocar needle 832 through the tissue as described above for previous embodiments. The catch on the delivery device receives the trocar needle 832, and the delivery device is removed from the body, passing the leader portion 830 attached to the delivery device through the noose 888*a* and the noose 888*b*. The trocar needle 832 is then removed from the catch. The procedure is then repeated on the contra-lateral side. The noose 888*a* can be drawn closed when the leader portion 830 is pulled, and the noose 888*b* can be drawn closed when the end portion 890 is pulled. The leader portion 830 on each side can be pulled intermittently to abut the implant 820 to the tissue. The leader portion 830 and the end portion 890 can be crossed and pushed in, for example, with a finger, to form a knot to secure the curved tab 886 to the tissue.

Figure 20:
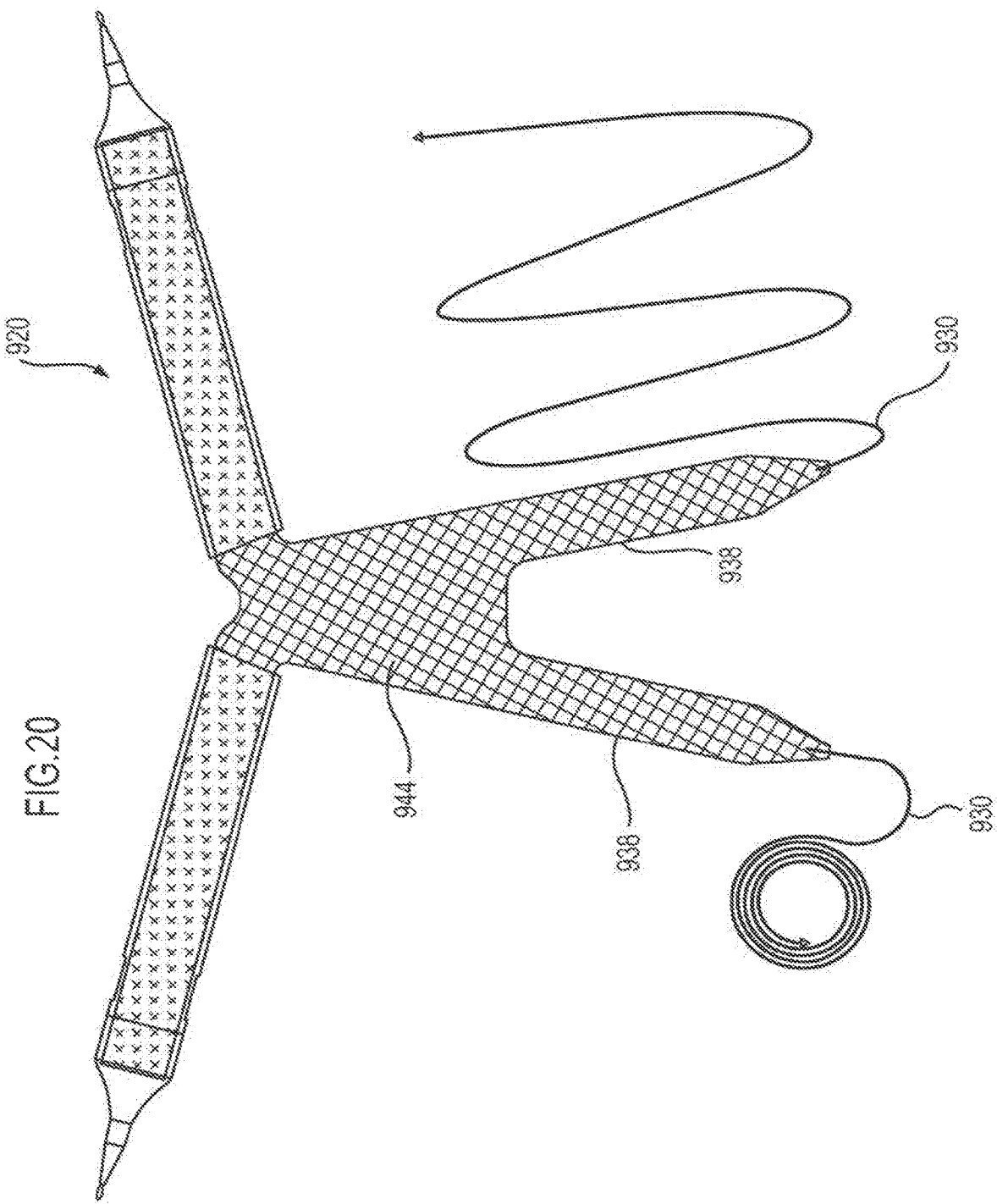

FIG. 20 illustrates another embodiment of an implant constructed similar to the implant 520. In this embodiment, the mesh strands are oriented perpendicularly rather than in an angular pattern. An implant 920 includes a support portion 944 and posterior straps 938 having a leader portion 930 coupled thereto using, for example, an adhesive or heat bonding. As shown in FIG. 20 the mesh strands of implant 920 (e.g., the support portion 922 and posterior straps 938) are oriented in a perpendicular pattern. Such a configuration of the mesh strands can help reduce strap stretch.

Figure 21:
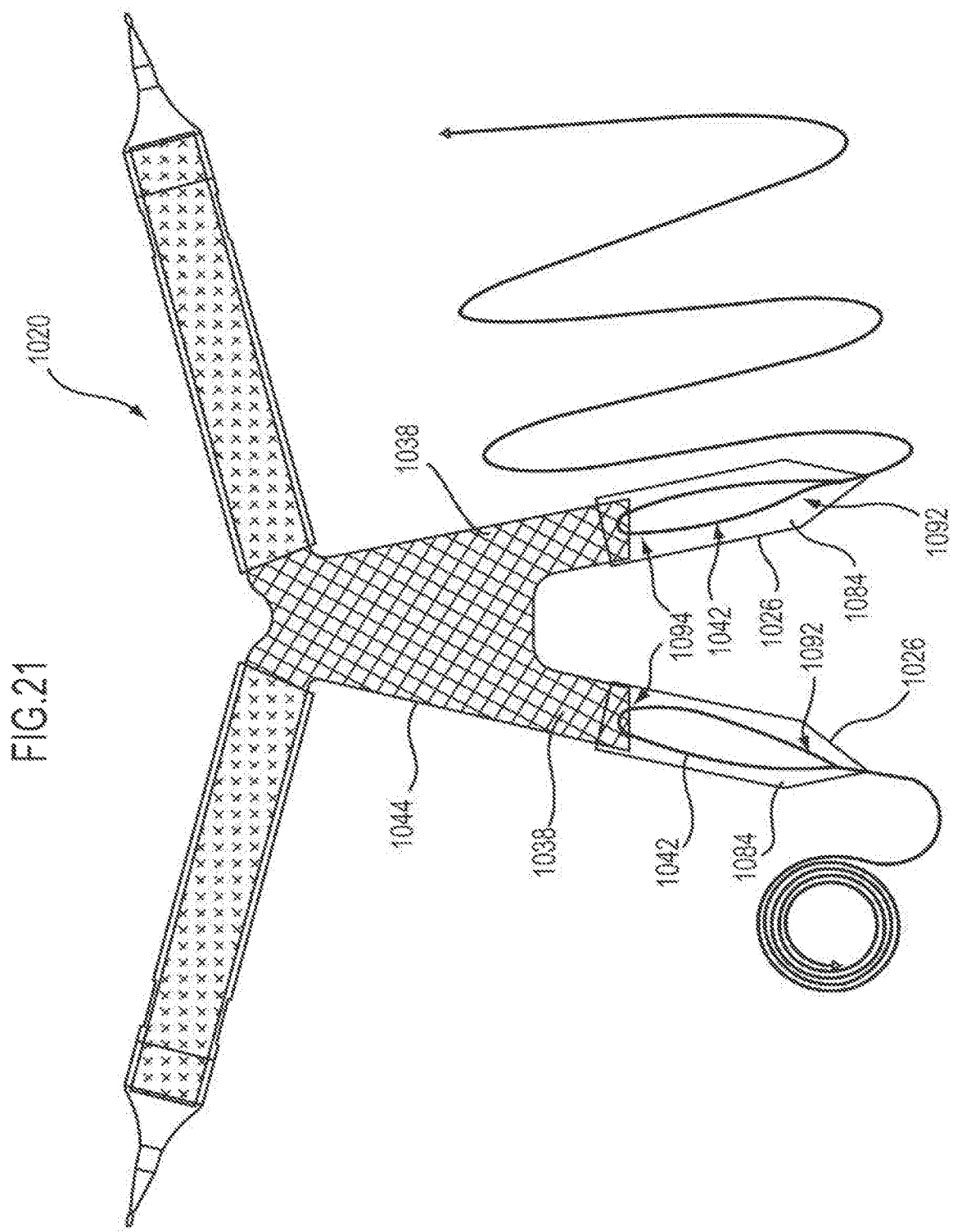

FIG. 21 illustrates an implant 1020 that is constructed similar to the implant 820 in FIG. 18. As with the implant 820, the implant 1020 includes a support portion 1044, posterior straps 1038 and insertion aids 1084 that include sleeves 1026. In this embodiment, the sleeve 1026 of the insertion aids 1084 is not heat sealed to the strap 1038, rather, a suture 1042 coupled to the sleeve 1026 is looped through the mesh of the strap 1038 at a location 1094 to secure the strap 1038 within the sleeve 1026. After pulling the straps 1038 through a tissue, the sleeve 1026 and looped suture 1042 can be cut external to the body at, for example, a location 1092. The strap 1038 will be released from the sleeve 1026, and the suture 1042 can be pulled out of the mesh of the straps 1038.

FIGS. 22-27 illustrate example embodiments of implants that arc adjustable in length and/or width. Such adjustments to the implant can be made prior to or during placement of the implant. An adjustment can include, for example, cutting the implant, or maneuvering the implant within a pelvic region such that the portion of the implant used as a support portion is adjusted to fit the particularly patient. The embodiments of an implant described in FIGS. 22-24 can be implanted in a pelvic region using any of the various approaches and delivery devices described herein. Although not necessarily shown for each embodiment, any of the implants can include sleeves and/or dilators and/or insertion aids to protect the implant during insertion. The implants can also include various connectors for associating the implant to a delivery device (e.g., a delivery device 164 or a delivery device 264) and various anchoring mechanisms (e.g., tangs, dimples).

Figure 22:
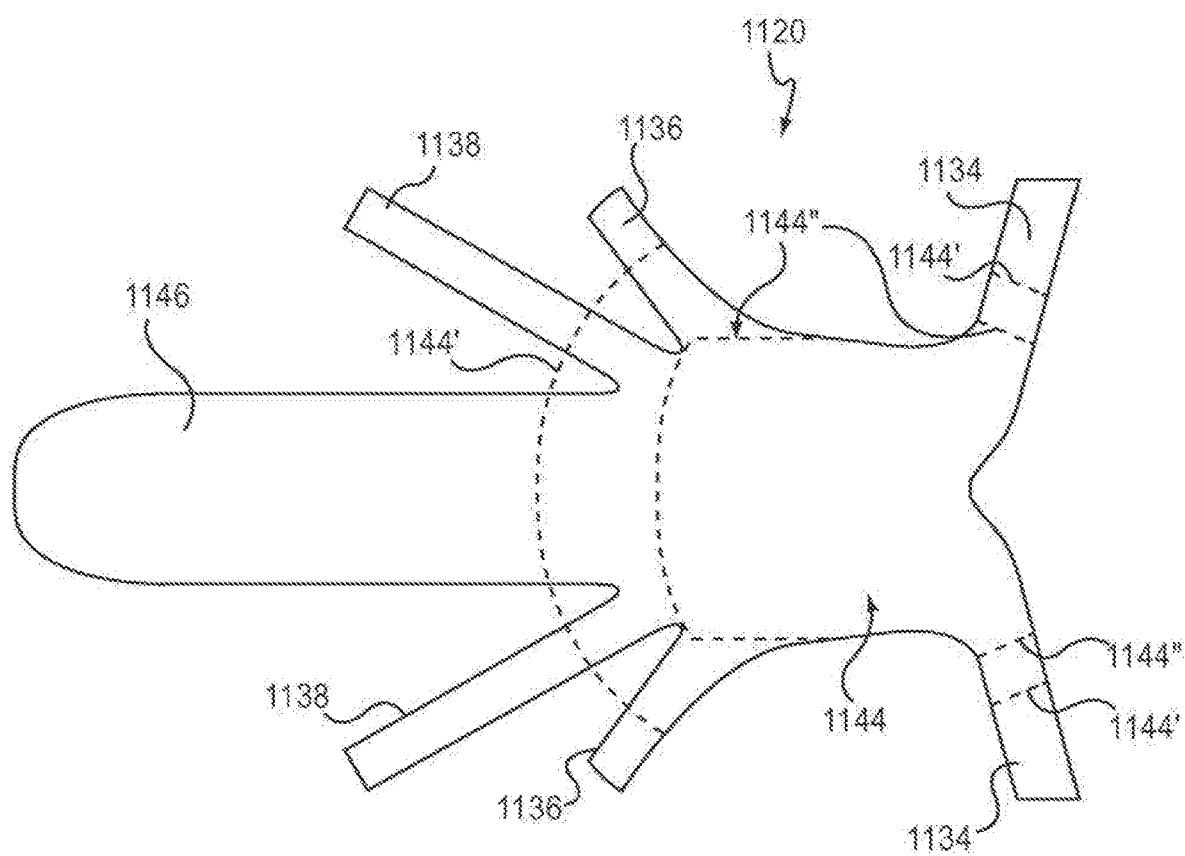
FIG. 22 is a top view of another embodiment of an implant.

As shown in FIG. 22, an implant 1120 includes anterior straps 1134, mid-line straps 1136, posterior straps 1138, an anterior support portion 1144 and an extended posterior support portion 1146. FIG. 22 illustrates two overlaid portions shown with dashed lines indicating examples of possible size adjustments to the anterior support portion 1144. The outline 1144' illustrates an example of how the implant 1120 can be adjusted to provide a larger anterior support portion to fit a large pelvic region. For example, to provide a support portion 1144' that is larger than the support portion 1144, the straps can be placed (e.g., pulled) through pelvic tissue only up to the location of the dashed line of 1144'. Such placement of the straps provides a support portion 1144' that includes a portion of the straps and is larger than the support portion 1144.

The outline 1144" illustrates an example of how the implant 1120 can be adjusted to accommodate a smaller support portion to fit a small pelvic region. In this example, the straps can be pulled further into the pelvic tissue up to the location of the dashed-line of 1144". Such placement of the straps provides a support portion 1144" that is smaller than the support portion 1144', because a larger portion of the straps, and in some cases, portions of the support portion 1144 are pulled into the pelvic tissue.

The area illustrated between the large outline 1144' and the small outline 1144" illustrates an example of the amount that the implant 1120 can be adjusted as the straps (1134, 1136, 1138) of the implant 1120 are pulled into pelvic tissue. In this embodiment, the straps 1136 are larger in width near the support portion 1144, which can provide more surface area for anchoring to the surrounding tissue. Thus, in some embodiments, a portion of the straps 1136 shown within the large outline 1144' can act as a support portion for larger patients, for example, by not being pulled into the tissue. In some embodiments, a portion of the straps 1136 within the large outline 1144' can be displaced or pulled into a tissue or ligament, resulting in a smaller support portion 1144", to accommodate a smaller sized patient.

Figure 23:
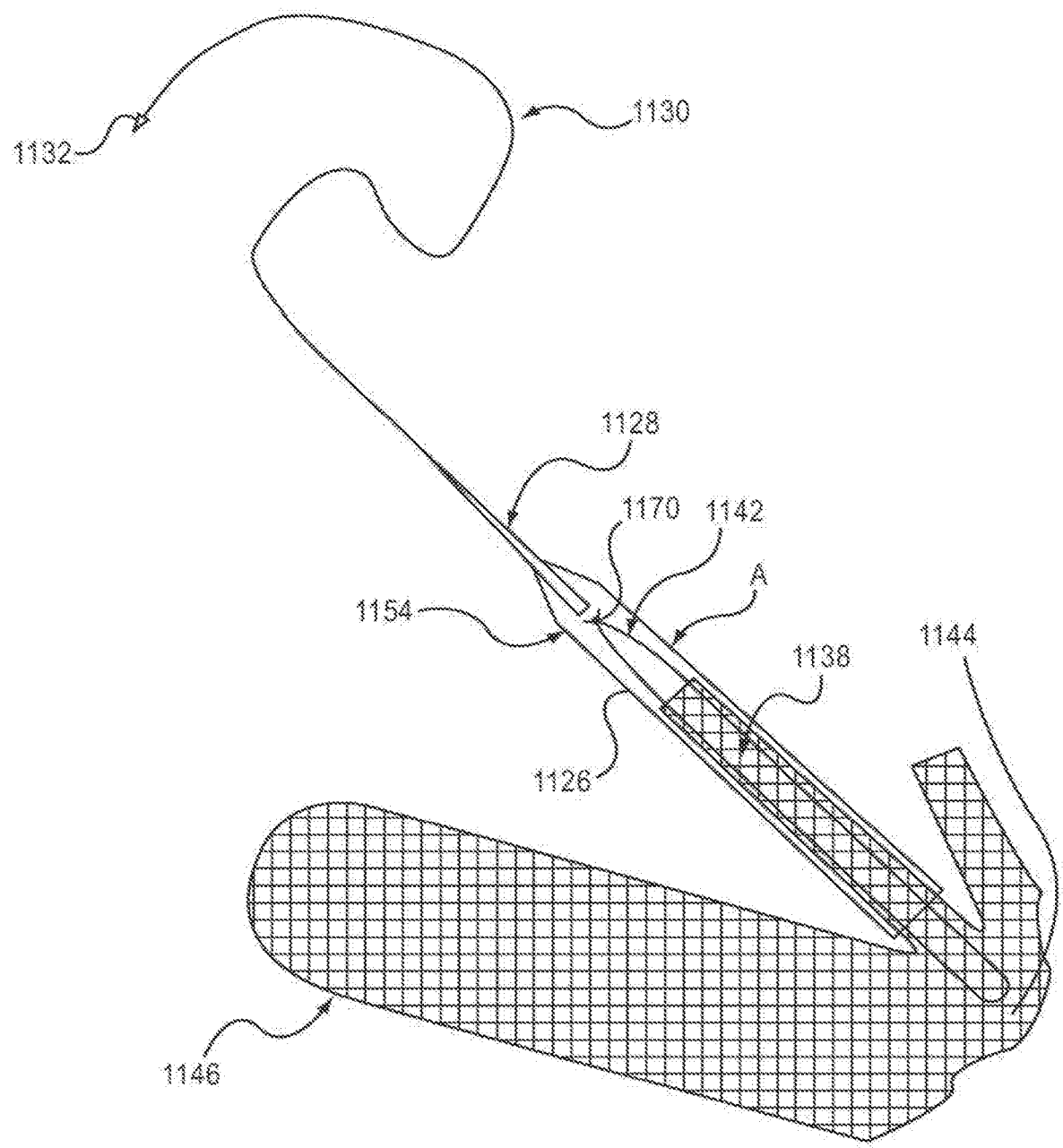
FIG. 23 is a top view of a portion of the implant of FIG. 22 shown with an embodiment of a sleeve assembly coupled to a strap of the implant.

The straps 1134, 1136, 1138 of the implant 1120 can have a length such that they can extend to the respective tissue securement sites, but are not long enough to extend further (e.g., within a vagina or through an exterior incision through the skin of the patient). The straps can be delivered into a pelvic region using a delivery device as described herein. FIG. 23 illustrates an example of a sleeve assembly 1154 that can be disposed over the straps to assist in the delivery process as previously described. FIG. 23 shows a sleeve assembly 1154 disposed over a strap 1138 for illustration purposes. The same or different sleeve assembly, dilator or other connector can also be coupled to the other straps of implant 1120.

The sleeve assembly 1154 includes a tapered sleeve 1126, a dilator 1128 molded to the sleeve 1126 and onto a leader 1130. A trocar needle 1132 is coupled to an end of the leader 1130. A suture 1142 is looped within the sleeve 1126 and is threaded through the strap 1138 and into the anterior support portion 1144. The suture 1142 secures the sleeve 1126 to the strap 1138 and helps prevent elongation of the strap 1138 during placement. To form the loop, the suture 1142 is threaded into the end of the strap 1138, from a distal end of the strap 1138 toward the anterior support portion 1144. The suture 1142 is looped around 90 degrees within the support portion 1144, and threaded back through the strap 1138. The ends of the suture 1142 are then secured to each other with a knot 1170 to form a closed loop. The knot 1170, or a portion of the suture 1142 near the knot 1170, can be coupled to the sleeve with, for example, a heat seal or an adhesive (not illustrated in FIG. 23). In alternative embodiments, a suture loop is threaded through only a portion of a strap. In some embodiments, the leader extends through a lumen of the dilator and a loop is formed (e.g., knotted or crimped) at a proximal or trailing end of the dilator.

The sleeve assembly 1154 can be pulled through a tissue (e.g., ligament, muscle, or soft tissue), for example, into a sacrospinous ligament or an arcus tendineus, using a delivery device, such as the delivery device 164 described herein. After pulling the sleeve assembly 1154 through the tissue, the sleeve assembly 1154 can be cut extracorporeal as described above for previous embodiments. For example, after pulling the sleeve assembly 1154 through a tissue, the sleeve 1126 and suture 1142 can be pulled through a vaginal incision and cut, for example, at a location A shown in FIG. 23. The sleeve 1126 can then be pulled off the strap 1138 and the suture 1142 can be pulled to unravel or otherwise release the suture 1142 from the strap 1138 and support portion 1144.

Figure 24:
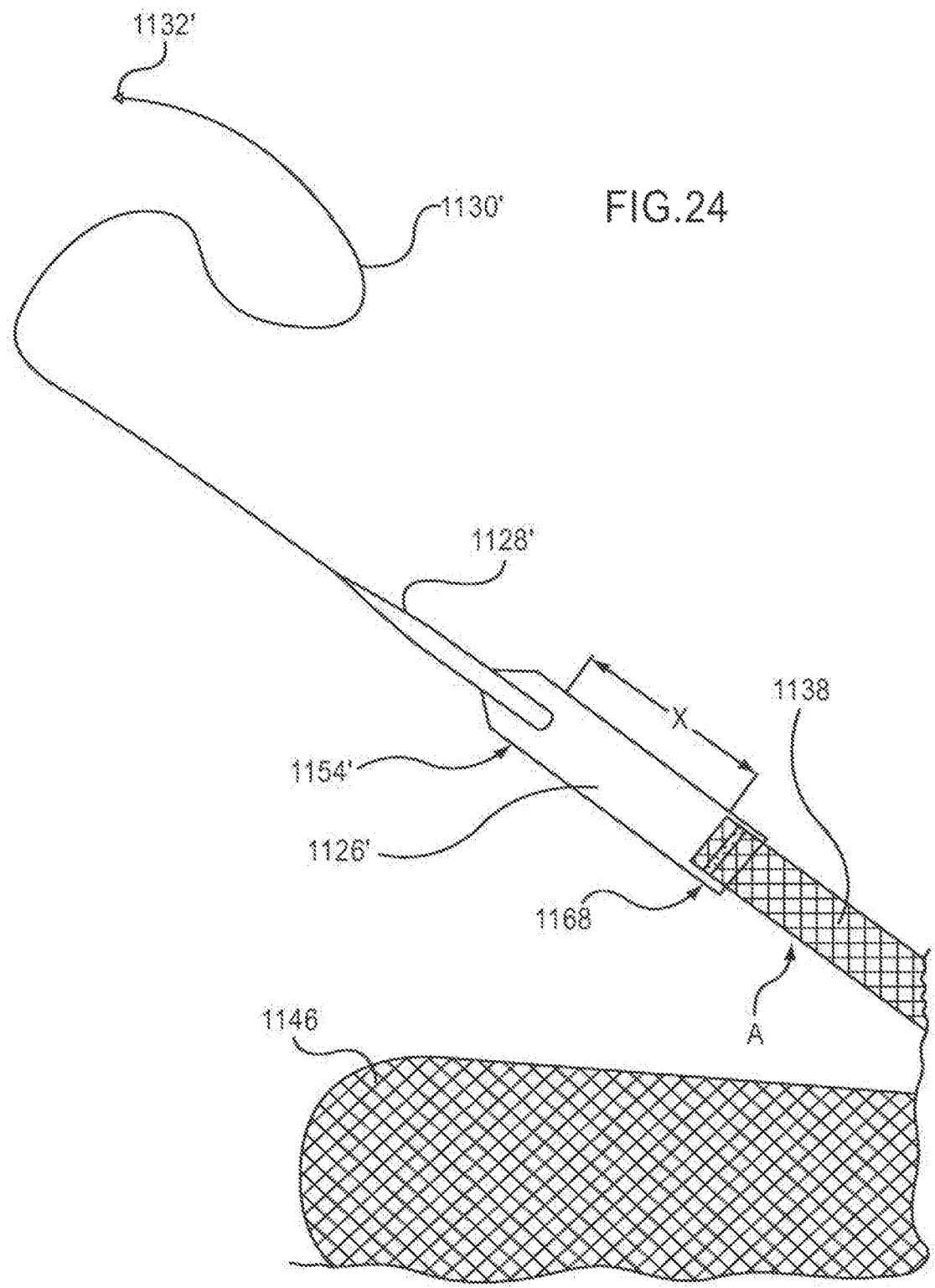
FIG. 24 is a top view of a portion of the implant of FIG. 22 shown with another embodiment of a sleeve assembly coupled to a strap of the implant.

FIG. 24 illustrates another embodiment of a sleeve assembly disposed over a strap 1138 of the implant 1120. In this embodiment, a sleeve assembly 1154' includes a tapered sleeve 1126', a dilator 1128', leader 1130' and trocar 1132'. Only a small portion of the strap 1138 is disposed within the sleeve 1126'. The strap 1138 is coupled to the sleeve 1126' with a heat seal 1168. The sleeve 1126' extends over only a portion of the strap 1138, and therefore, only protects or covers that portion of the strap 1138 during the delivery procedure. In this situation, however, only a small portion of the strap 1138 will be in contact with tissue during delivery (due to the short length of the strap). As with the previous embodiment, the sleeve 1126' and a portion of the strap 1138 can be cut after inserting the strap 1138 through tissue. For example, the sleeve 1126' and strap 1138 can be cut at a location A as shown in FIG. 24.

Figure 25:
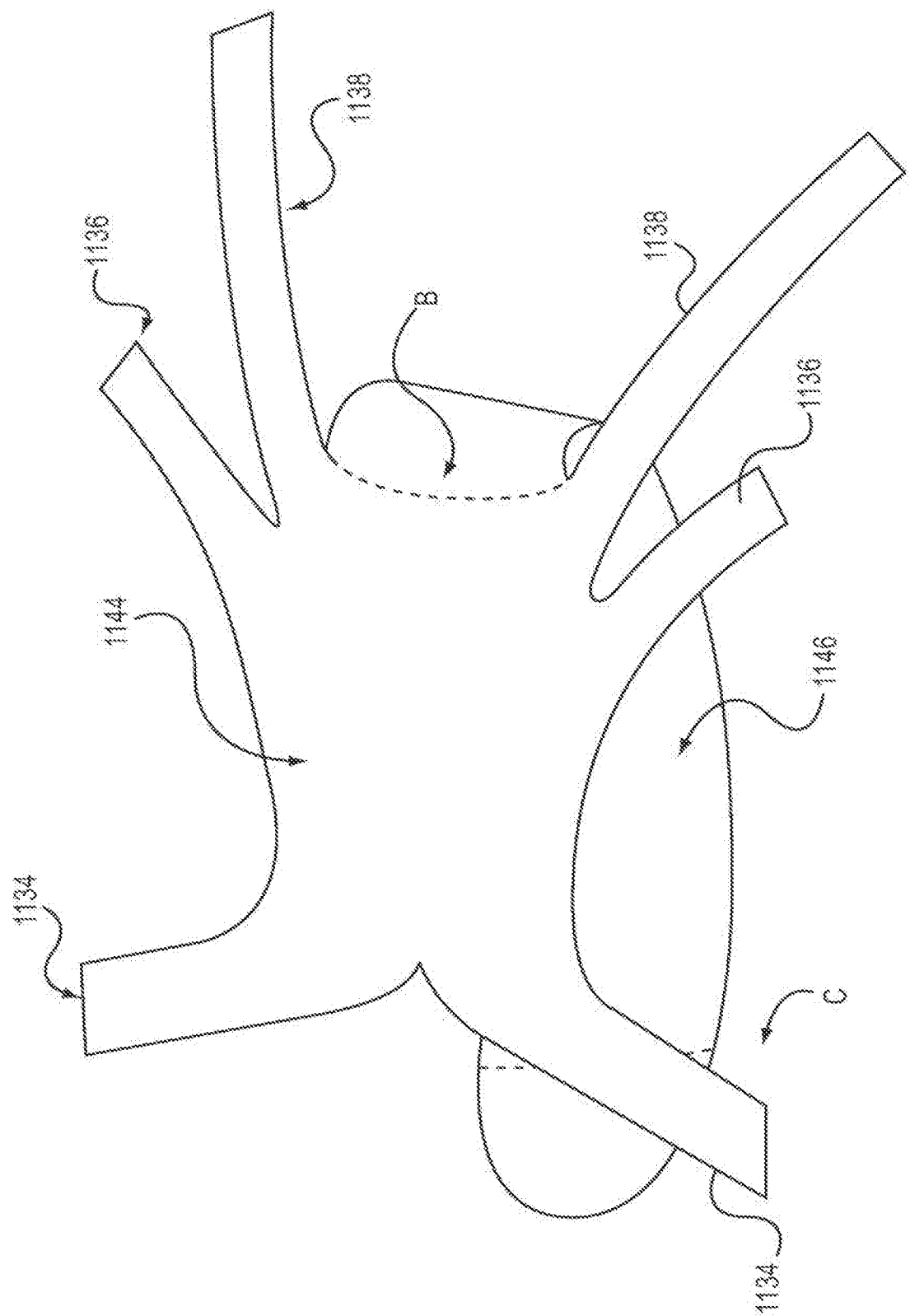
FIG. 25 is a side perspective view of the implant of FIG. 22.

FIG. 25 illustrates the implant 1120 with sleeves removed and in an example orientation within a pelvic region (pelvic region not shown). As shown in FIG. 25, the posterior support portion 1146 can be tucked into the posterior fascia within the pelvic region (not shown). In some cases, for example, for a patient having a uterus, it may be desirable to cut the implant along dotted line B. In such a case, the posterior support portion 1146 can be discarded or placed separately around the posterior area of the vagina. The posterior support portion 1146 can optionally be trimmed to a desired length by cutting the posterior support portion 1146 along, for example, dotted line C.

Each of the straps 1134, 1136, 1138 can be delivered to a pelvic region through an anterior vaginal incision. The mid-line straps 1136 and posterior straps 1138 are angled towards the posterior of the implant 1120 so that excess implant material is displaced towards the posterior end of the implant 1120. The mid-line straps 1136 can be implanted, for example, into an arcus tendineus and the posterior straps 1138 can be implanted, for example, into a sacrospinous ligament. The anterior straps 1134 can be placed into, for example, an arcus tendineus or an obturator membrane or muscle. The order of delivering the straps can vary as described above. A posterior vaginal incision can be made to provide access to the posterior support portion 1146 for wrapping the posterior support portion 1146 around a vaginal cuff and tucking it into a desired position. The straps 1134, 1136, 1138 can be tensioned in any order. The anterior straps 1134 can help position the anterior support portion 1144 anteriorly and laterally. The mid-line straps 1136 (e.g., secured to the arcus tendineus) can provide lateral support to the anterior support portion 1144. The posterior straps 1138 (e.g., secured to the sacrospinous ligament) can provide a deeper anchor point and a desired angle for vaginal support.

Figure 26:
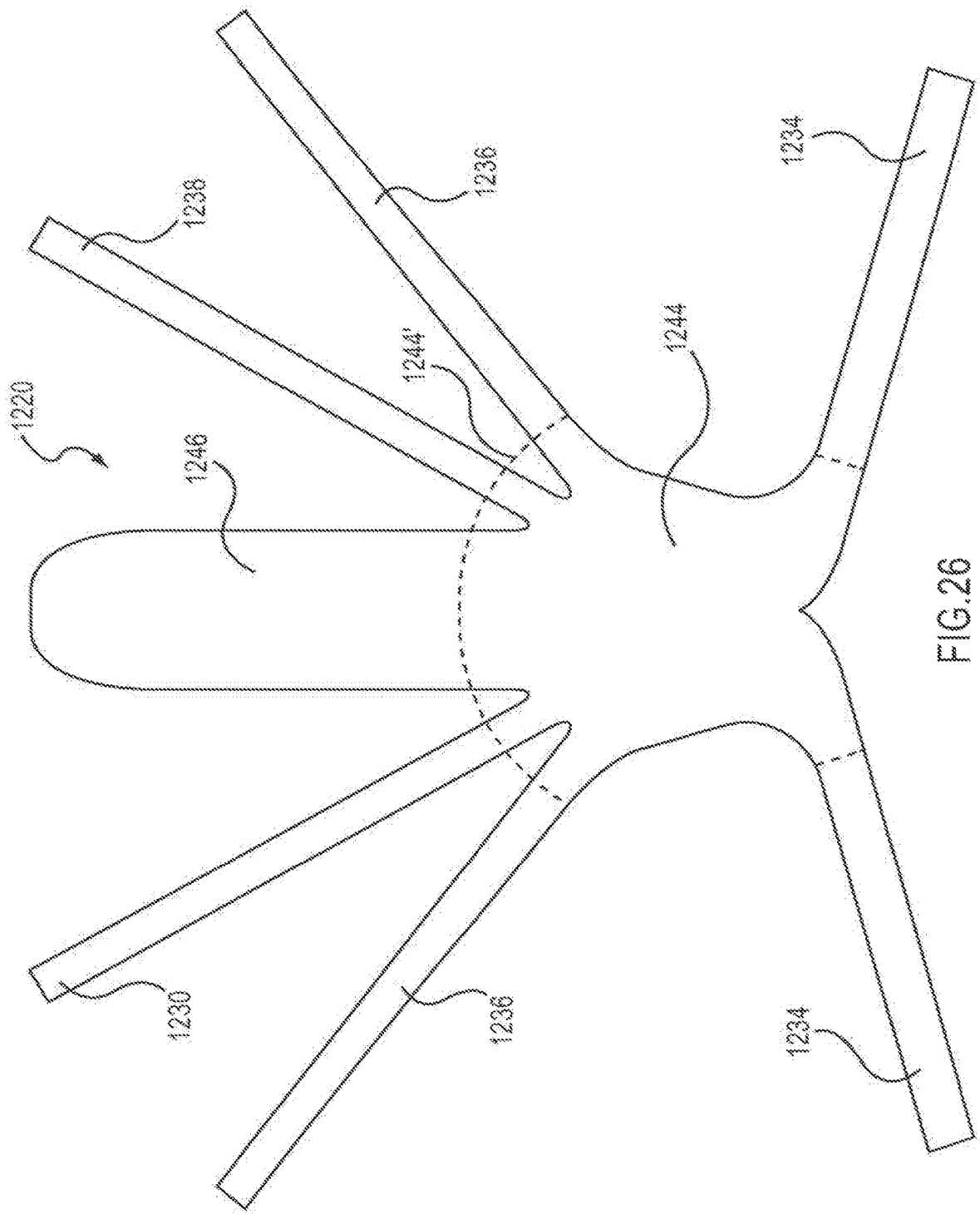
FIGS. 26 and 27 are each a top view of a different embodiment of an implant.

FIG. 26 illustrates an implant similar to the implant 1120 but has longer straps than the implant 1120. An implant 1220 includes anterior straps 1234, mid-line straps 1236, posterior straps 1238, an anterior support portion 1244 and an extended posterior support portion 1246. FIG. 26 illustrates an overlaid portion 1244' that indicates an example of a possible size adjustment to the anterior support portion 1244. The outline 1244' illustrates a larger anterior support portion to fit a large pelvic region described in more detail below. The implant 1220 can be delivered using any of the methods and devices described herein. The straps of the implant 1220 allow the implant 1220 to also be delivered using various other delivery devices not specifically described herein.

The area illustrated between the large outline 1244' and the smaller outline of the support portion 1244 illustrates the amount the implant 1220 can be adjusted in both length and width. As described previously for implant 1120, the straps (1234, 1236, 1238) of the implant 1220 can be pulled into pelvic tissue varying amounts to adjust the effective size of the anterior support portion 1144. For example, the straps can be pulled into pelvic tissue until a desired amount of the support portion 1244 is positioned within an anterior region of the pelvis. In some embodiments, a portion of the anterior support portion 1244 is pulled into the pelvic tissue such that a smaller portion of the support portion 1144 is disposed within the anterior region of the pelvis. In some embodiments, the straps are only pulled partially into the tissue, for example, up to the border of the outline 1244', such that a portion of the straps is disposed within the anterior region of the pelvis. In such a case, the portion of the straps remaining in the anterior region of the pelvis increasing the effective size of the support portion 1244. Thus, a portion of the straps within the large outline 1244' can act as a support portion for larger patients, or can be displaced or pulled into tissue to accommodate a smaller patient.

Figure 27:
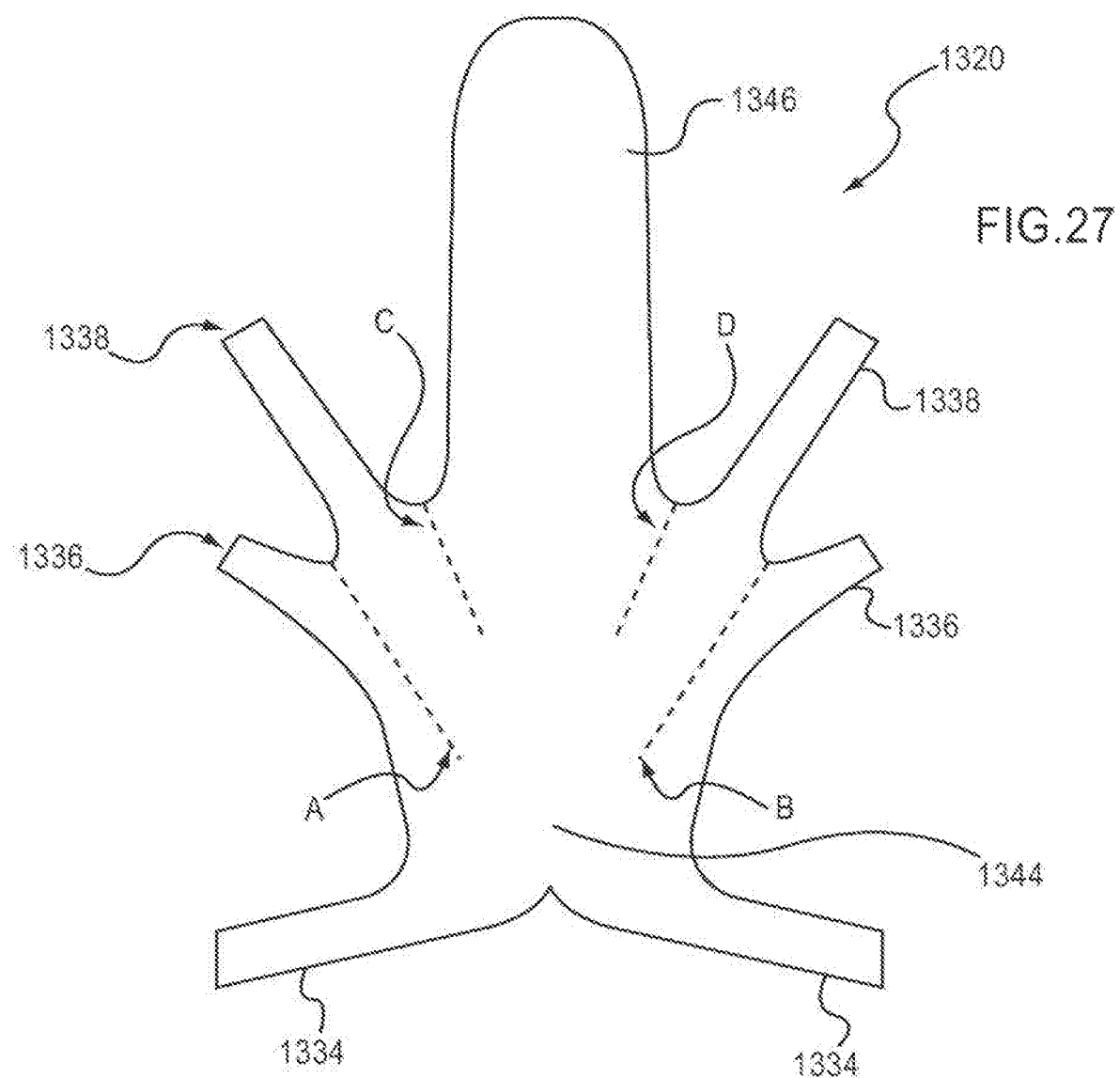

FIG. 27 illustrates another embodiment of an implant that is similar to the implant 1120. An implant 1320 includes anterior straps 1334, mid-line straps 1336, posterior straps 1338, an anterior support portion 1344 and a posterior support portion 1346. The implant 1320 can be custom-fit for an individual patient by cutting a selected portion of the implant 1320. For example, a portion or the entire length of dotted lines A, B, C and/or D can be cut to provide a custom fit for a smaller patient. In one example, cutting the dotted lines A and B lengthens the mid-line straps 1336 and enables the mid-straps 1336 to be pulled further into pelvic tissue, or to reach securement sites within the pelvis that they would otherwise not be able to extend to. For example, lengthening the mid-line straps 1336 allows the mid-line straps 1336 to be passed through a mid-arcus (of an arcus tendineus). In another example, dotted lines C and D can be cut to allow the posterior straps 1338 to be pulled further into tissue. By pulling the straps 1338 further into tissue, the anterior support portion 1344 of the implant 1320 within the anterior region of the pelvis will be smaller. In some embodiments, it may be desirable to cut along lines A, B, C and D to lengthen the straps 1336 and 1338.

Figure 28:
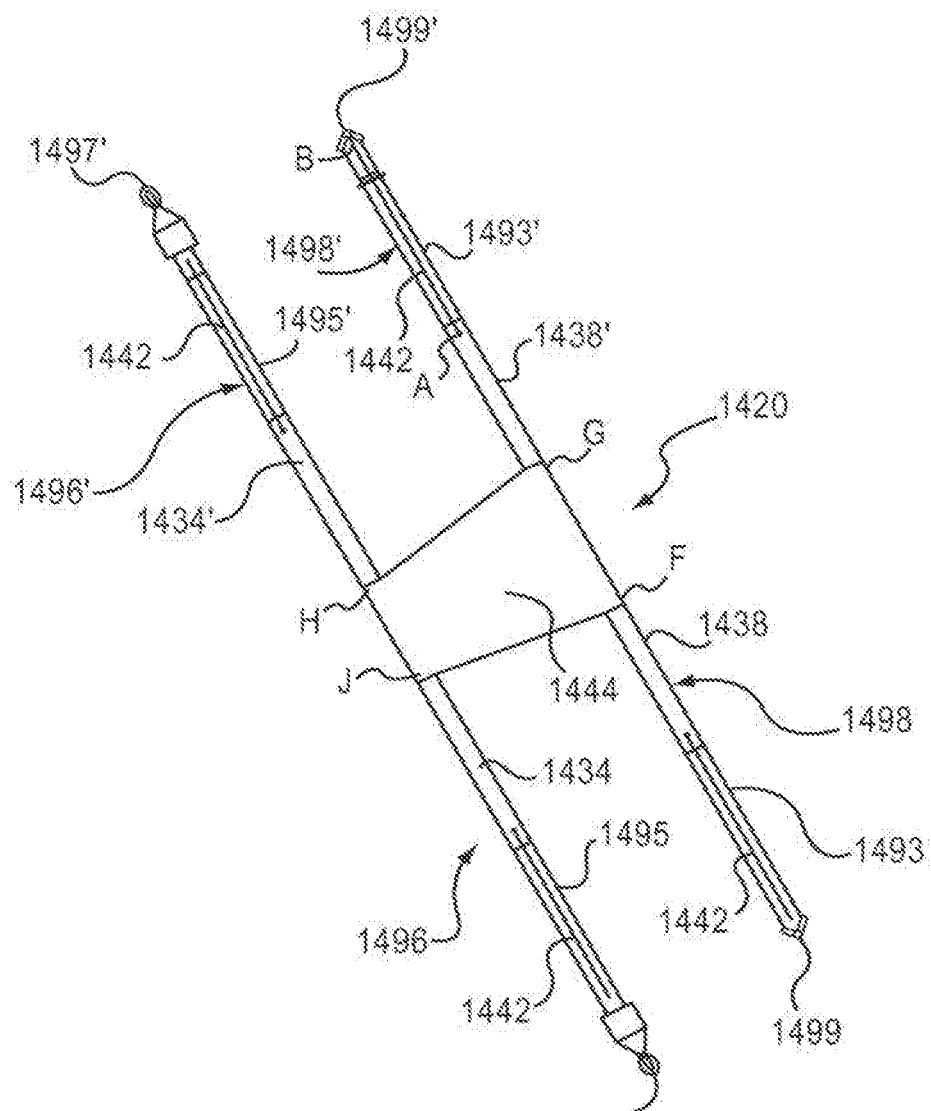
FIG. 28-30 are each a top view of a different embodiment of an implant.

FIG. 28 illustrates an embodiment of an implant that includes attachable sleeve and strap assemblies that can be coupled to a support portion of a pelvic implant prior to, or after implantation into a pelvic region. An implant 1420 includes an anterior support portion 1444, sleeve and strap assemblies 1496 and 1496' attached to the anterior support portion 1444 at corners J and H, respectively, and sleeve and strap assemblies 1498 and 1498' attached to the anterior portion 1444 at corners F and G, respectively. A separate suture and needle (not shown) can be used to secure the strap of the sleeve and strap assemblies 1496, 1496', 1498, 1498' to the support portion 1444. In other embodiments, other attachment methods can be used to secure the straps to the support portion, such as, for example, heat bonding, gluing, or using fasteners. The sleeve and strap assemblies 1496, 1496', 1498, 1498' can each be attached to the support portion 1444 by a user (e.g., a physician or medical technician) prior to implantation or after the sleeve and strap assemblies have been passed through a pelvic tissue. The sleeve and strap assembly 1498 is constructed the same as the sleeve and strap assembly 1498' and will be collectively described below. Similarly, the sleeve and strap assembly 1496 is constructed the same as the sleeve and strap assembly 1496' and will be collectively described below.

The sleeve and strap assemblies 1498, 1498' include a sleeve 1493, 1493', a strap 1438, 1438' and a low profile connector 1499, 1499'. The sleeve and strap assemblies 1496, 1496' include a sleeve 1495, 1495' and a loop connector 1497, 1497'. A suture 1442 is used to secure each of the straps (1434, 1434', 1438, 1438') to its respective sleeve (e.g., 1493, 1493', 1495, 1495'). For example, as shown for the sleeve and strap assembly 1498', a suture 1442 is secured to the strap 1434' at point A, threaded through the inside of the sleeve 1493' and secured to the low profile connector 1499' at or about point B. A similar suture 1442 is secured to each of the other strap assemblies in a similar manner. A single strand of suture 1442 is depicted, but it should be understood that multiple strands can be used in other embodiments.

The connectors 1499, 1499' and connectors 1497, 1497' can each be used to associate to a delivery device, such as the delivery device 264 described above to deliver each of the straps of the implant 1420 to a selected tissue site. The sleeve and strap assemblies 1498, 1498' can be used to secure the straps 1438 to, for example, a sacrospinous ligament or tendineus arch of the levator ani muscle. The sleeve and strap assemblies 1496, 1496' can be used to secure the straps 1434, 1434' to, for example, an arcus tendineus or an obturator muscle or membrane.

Each of the sleeve and strap assemblies 1496, 1496', 1498, 1498' can be pulled through a desired tissue site, and retrieved external to the patient's body, through for example, a vaginal incision or an exterior incision. Once all of the sleeve and strap assemblies 1496, 1496', 1498, 1498' are positioned, the sutures 1424 or both the sutures 1424 and the respective sleeve 1493, 1493', 1495, 1495' can be cut to release them from their respective strap in a similar manner as described above for other embodiments. The sleeves 1493, 1493', 1495, 1495' are then pulled outward away from the body of the patient to leave the straps 1434, 1434', 1438, 1438' to engage the surrounding tissue. The sutures 1424 remain attached to the straps, for example, at point A, allowing the sutures 1424 to be used to retrieve a cut strap portion after trimming the strap, if needed.

Figure 29:
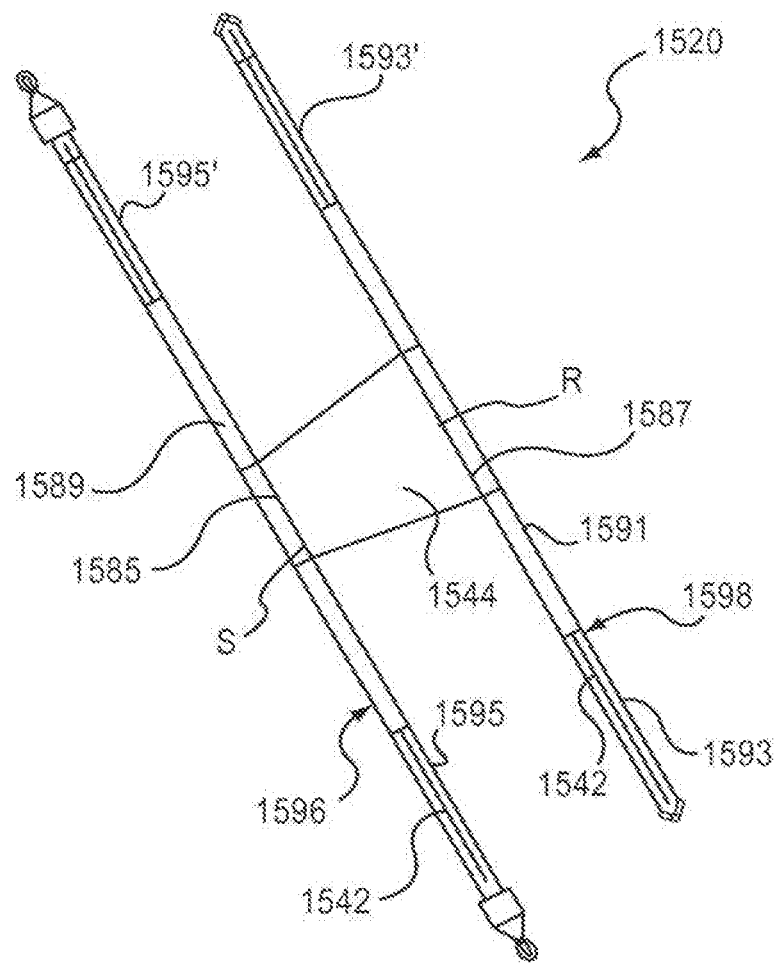

FIG. 29 illustrates another embodiment of an implant similar to the previous embodiment. An implant 1520 includes a sleeve and strap assembly 1598 and a sleeve and strap assembly 1596. The sleeve and strap assemblies 1598 and 1596 are each coupled to a support portion 1544 of the implant 1520. The sleeve and strap assembly 1598 includes a single strap 1591, and a pair of sleeves 1593 and 1593' disposed over opposite ends of the strap 1591. Similarly, the sleeve and strap assembly 1596 includes a single strap 1589, and a pair of sleeves 1595 and 1595' disposed over opposite ends of the strap 1589. Other components of the sleeve and strap assemblies 1598 and 1596 are substantially the same as the sleeve and strap assemblies 1498 and 1596, respectively. For example, a suture 1542 can be used to secure the straps of the implant 1520 to the sleeves.

In this embodiment, the sleeve and strap assembly 1598 is coupled along an edge 1587 of the support portion 1544 as indicated at R. The sleeve and strap assembly 1496 is coupled to the support portion 1544 along an edge 1585 as indicated at S. Each of the ends of the strap 1591 can be secured to a tissue site in a similar manner as described above for straps 1438 and 1438'. Likewise, the ends of strap 1589 can be secured to a tissue site in a similar manner as described above for straps 1434 and 1434'.

Figure 30:
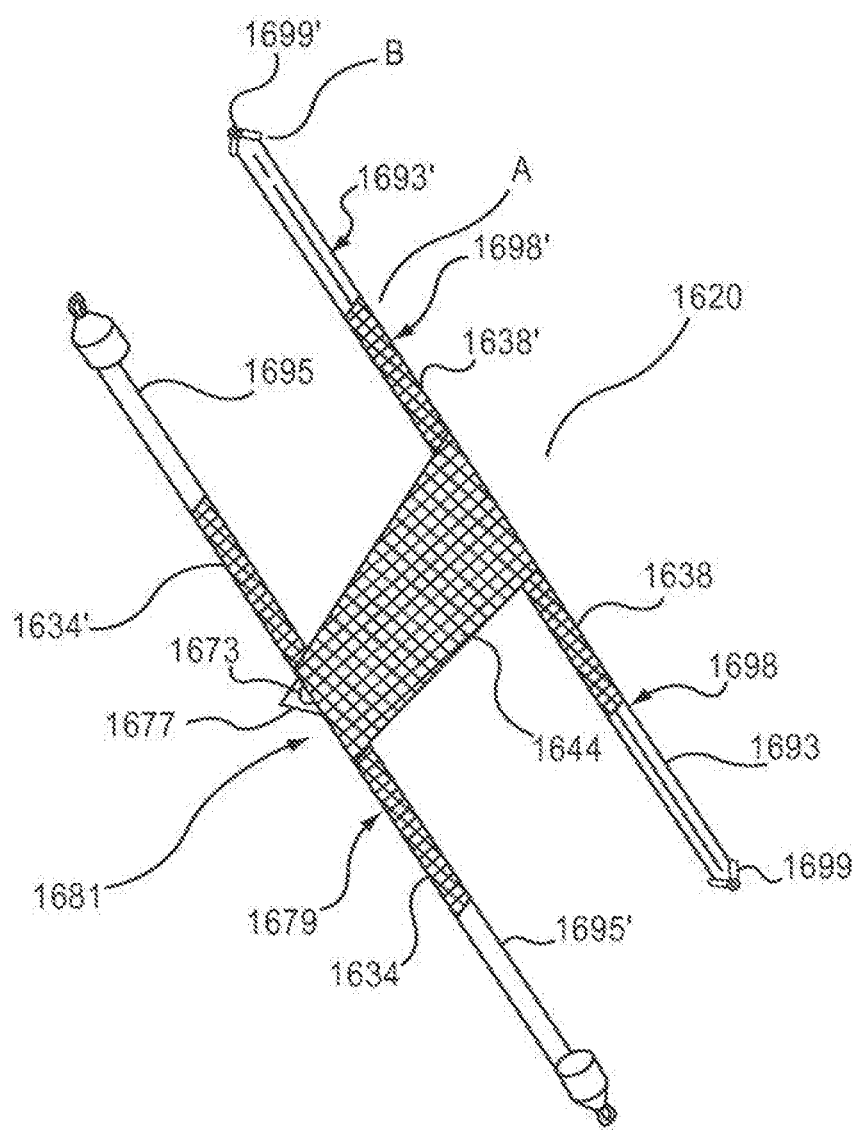

Another similar embodiment of an implant is illustrated in FIG. 30. An implant 1620 includes a support portion 1644, two proximal anterior straps 1634, 1634', and two distal anterior straps (or posterior straps) 1638, 1638'. The straps can be formed as a single component with the support portion 1644 or can be attachable as in the previous two embodiments.

A proximal end portion 1681 of the support portion 1644 is disposed within a sleeve assembly 1679 having a center tab 1677 joining two halves 1695, 1695' of the sleeve assembly 1679. The straps 1634, 1634' are disposed free-floating within the sleeve halves 1695, 1695'. A portion of the support portion 1644 is not disposed within an interior region defined by the sleeve assembly 1679, but in some embodiments the sleeve assembly can include flaps (not shown) that can extend to cover a larger portion of the support portion 1644.

Figure 31:
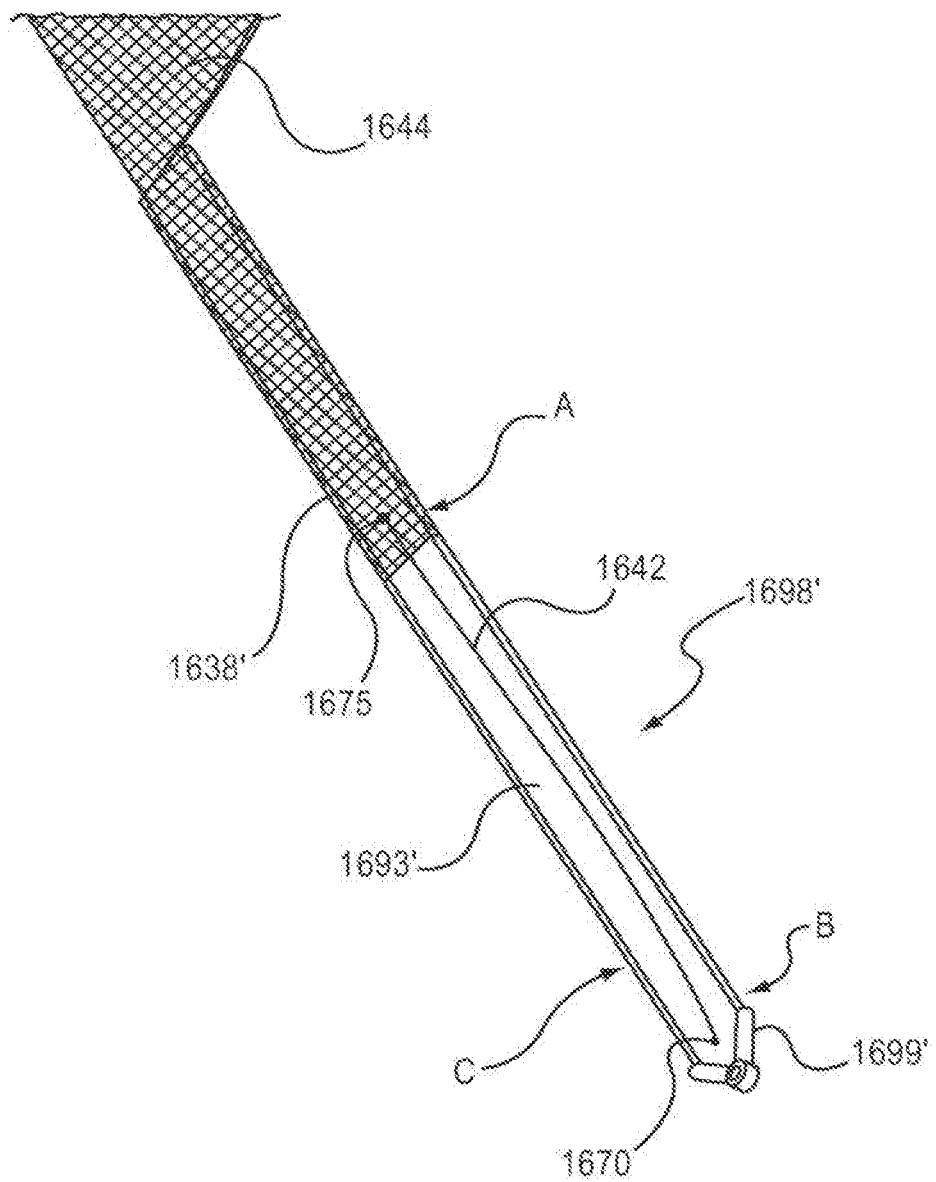
FIG. 31 is a top view of a portion of the implant of FIG. 30.

FIG. 31 illustrates a portion of the implant 1620 including a sleeve assembly 1698' having a sleeve 1693' and a low profile connector 1699', disposed over the strap 1638'. A similar sleeve assembly 1698 is disposed over the strap 1638 (shown in FIG. 30) and includes a sleeve 1693 and a low profile connector 1699. As illustrated in FIG. 31, a suture 1642 is knotted at a first end 1675 and a second end of the suture 1642 is threaded through a first wall or top portion of sleeve 1693' at location A (with the knot preventing the suture 1642 from being pulled through the top portion of the sleeve 1693'), through the strap 1638', and through a second wall or bottom portion of the sleeve 1693' (on a bottom side and not shown in FIG. 31). The second end of the suture 1642 is then run external to the second wall along a length of the sleeve 1693' to a location B where it is threaded back through the second wall of the sleeve 1693', through the strap 1638' and through the first wall of the sleeve 1693'. In some embodiments, the suture 1642 is tensioned or adjusted in length such that the strap 1638' and suture 1642 are substantially equal in length. A knot 1670 is formed at the second end of the suture 1642 at location B to secure the suture 1642 to the sleeve 1693'. In other embodiments, the second end of the suture can be coupled to the sleeve by other means, and/or coupled to the low profile connector 1699'. For example, the second end of the suture can be secured to the sleeve 1693' and/or connector 1699' by a heat seal, gluing, molding, or tying. In some embodiments, the suture can extend from A to B along an inside of the sleeve.

The implant 1620 can be implanted into a pelvic region in the same manner as described for other embodiments. For example, an implant 1620 can be delivered into a pelvic region using an inside-out approach, an outside-in approach, supra-pubic approach, or transvaginal approach. After each of the straps 1638 and 1638' with their respective sleeve assembly 1698, 1698' is pulled through a selected tissue site, and any necessary adjustments and/or tensioning is complete, the sleeve assemblies and sutures can be removed from the strap in a similar manner as described for previous embodiments. For example, the sleeve and suture can be cut at location C (See FIG. 31), to allow the sleeve (with attached suture) to be pulled off the strap. In some embodiments, only the sleeve is cut, as the suture is coupled to the sleeve. In some embodiments, only a suture end is cut (e.g., the knot 1670 is cut off) to release the sleeve from the strap.

The sleeve assembly 1679 disposed over the straps 1634 and 1634' (see FIG. 30) can also be removed after passing the strap through a pelvic tissue. After the straps 1634 and 1634' are pulled through a selected tissue site, the sleeve assembly 1679 can be removed by making a cut through an opening 1673 on the center tab 1677, which releases the two sleeve halves 1695 and 1695'. The two cut portions of the center tab 1677 can be removed and discarded. The sleeves 1695 and 1695' can be pulled to remove them from the straps 1634 and 1634', leaving the straps 1634 and 1634' to engage the surrounding tissue.

Figure 32:
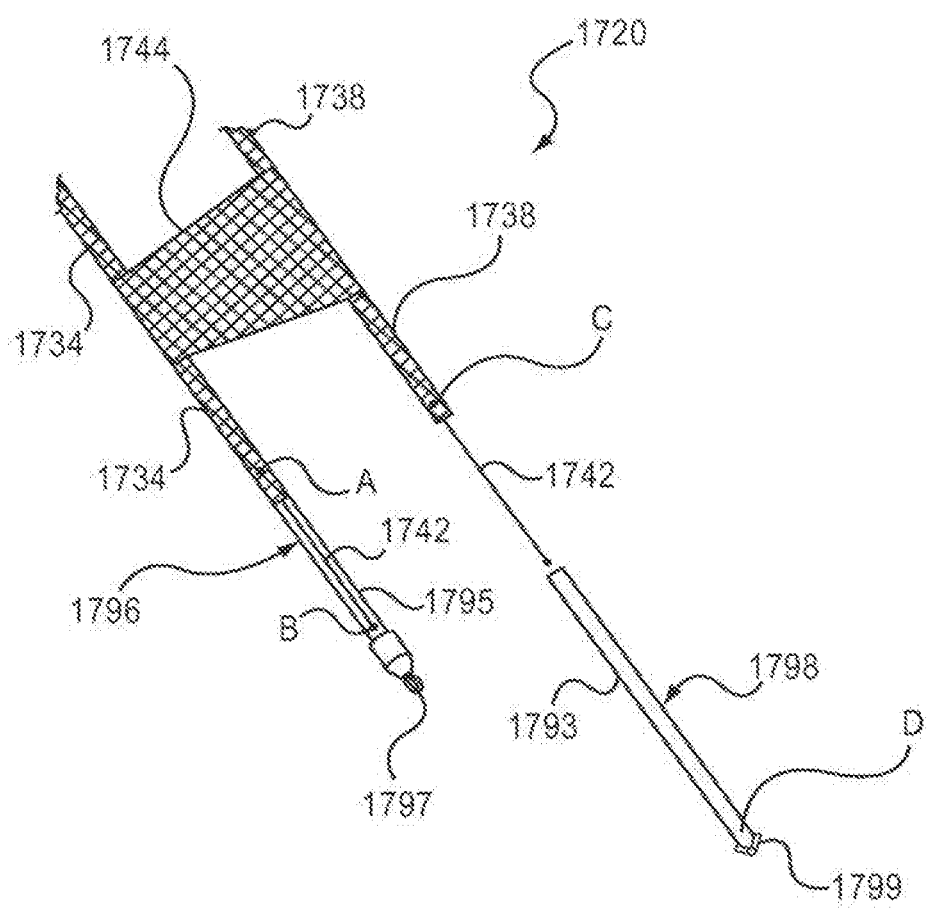
FIG. 32 is a top view of a portion of another embodiment of an implant.

FIG. 32 illustrates a portion of an embodiment of an implant similar to the implant 1620 described above. An implant 1720 includes proximal anterior straps 1734 and distal anterior straps (or posterior straps) 1738 and a support portion 1744. In this embodiment, sleeve assemblies 1796, include a sleeve 1795 and a connector 1797, and are disposed over each of the straps 1734. The sleeve assembly 1796 is coupled to a strap 1734 with a suture 1742. The suture 1742 is secured to the strap 1734 by knotting or tying the suture 1742 to the strap 1734 at location A. The suture 1742 is then extended through an inside of the sleeve 1795 to a location B where it is secured to the sleeve 1795 and/or connector 1797 by knotting, using a heat seal or adhesives or other coupling methods.

Similarly, sleeve assemblies 1798, include a sleeve 1793 and connector 1799, and are disposed over each of the straps 1738. A suture 1742 is secured to a strap 1738 by tying or knotting the suture 1742 to the strap 1738 at location C. Although not shown in FIG. 32, the suture 1742 can be extended through an inside of the sleeve 1793 to a location D where it can be secured to the sleeve 1793 and/or connector 1799 as described for sleeve assemblies 1796. FIG. 32 illustrates the sleeve 1793 removed from the strap 1738 for illustration purposes. In this embodiment, each of the sutures 1742 remain coupled to the straps 1738 and the straps 1734 after removing the sleeve assemblies 1798 and 1796. For example, as shown in FIG. 32, to remove the sleeve assembly 1798 from the strap 1738, the suture end at location D can be cut allowing the sleeve 1793 to be pulled off the strap 1738. The suture end at location C will remain secured to the strap 1738. When the strap 1738 is trimmed (if needed), the suture 1742 (still secured to the cut portion of the strap), can then be used to retrieve the cut portion of the strap. The sleeve assembly 1796 can be removed from the strap 1734 in a similar manner.

Figure 33:
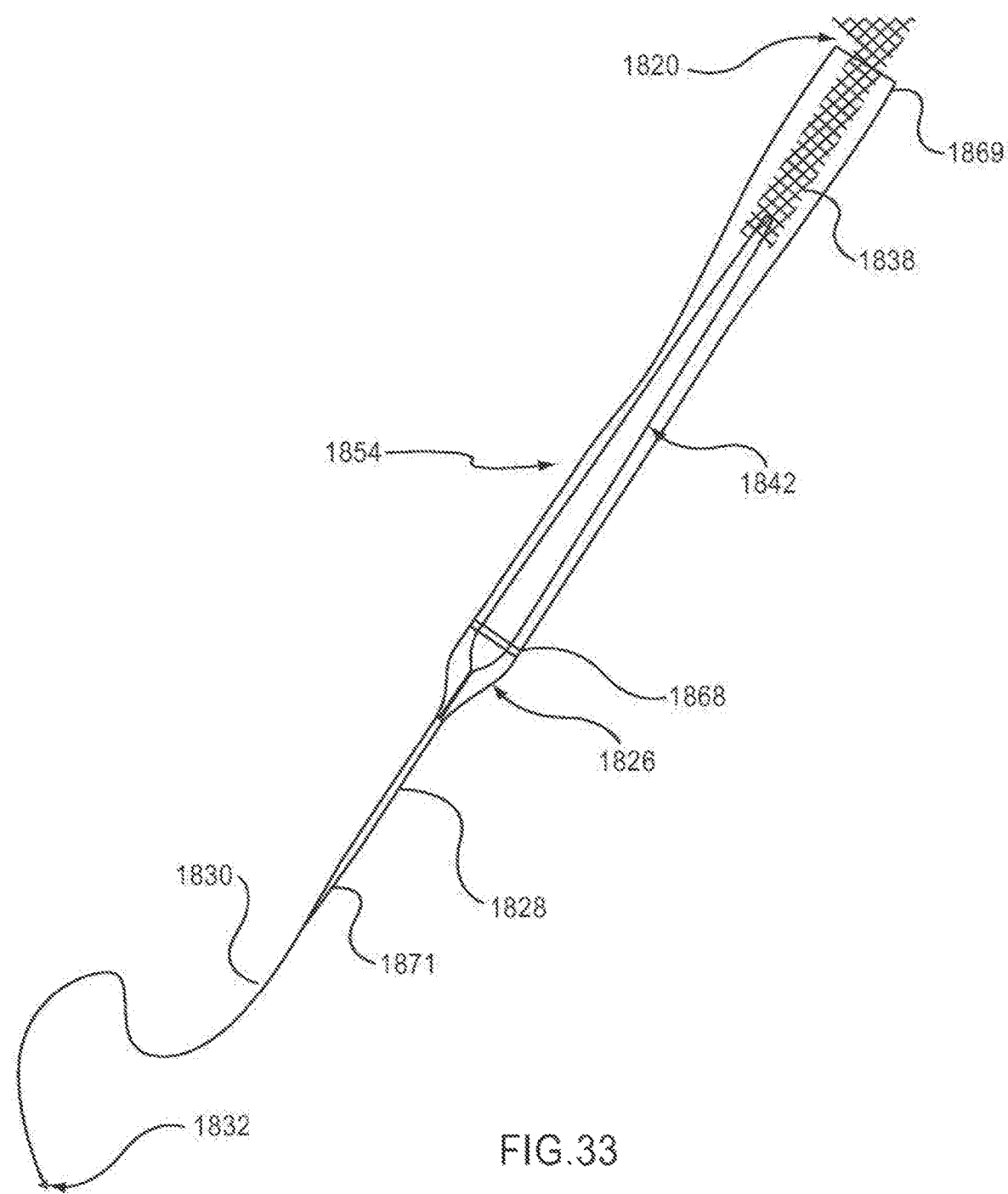
FIGS. 33-36 are each a top view of a different embodiment of a sleeve assembly coupled to a portion of an implant.

FIGS. 33-36 each illustrate an embodiment of a sleeve assembly that can be used to assist in the implantation of a strap of an implant. Each of the embodiments of FIGS. 33-36 can be coupled to a delivery device, such as delivery device 164, and can be inserted into a pelvic region using any of the approaches described herein. FIG. 33 illustrates an embodiment of a sleeve assembly 1854 associated to a strap 1838 of an implant 1820 for illustration purposes. Thus, the sleeve assembly 1854 can be coupled to a variety of different types of straps of a variety of different types or configurations of an implant.

The sleeve assembly 1854 includes a sleeve 1826 and a dilator 1828 coupled to the sleeve 1826. A suture 1842 forms a loop inside of the sleeve 1826 and is threaded through the strap 1838. The suture 1842 extends through the dilator 1828 and exits a distal end portion 1871 of the dilator 1828. A heat seal 1868 can be used to secure the suture 1842 to the sleeve 1826. The portion of the suture 1842 extending outside the dilator 1828 is the leader 1830. A trocar needle 1832 is coupled to an end of the leader 1830 and can be used to associate to a delivery device as described above. An opposite end of the suture 1842 can be knotted within the dilator 1828 (not shown in FIG. 33) to secure it thereto and form the loop within the sleeve 1826.

The dilator 1828 is relatively long and smooth and tapers to the end portion 1871. As described previously for other embodiments, the dilator 1828 can expand a passage formed by the trocar needle 1832 during insertion through a tissue, to ease the transition to a cross-section of the sleeve 1826. The sleeve 1826 is also tapered, which helps provide a lead-in through the passage formed by the dilator 1828 through the tissue. As shown in FIG. 33 a length of the sleeve 1826 is greater than a length of the strap 1838. In some embodiments, the tapered sleeve 1826 can be long enough to extend out of the vagina during delivery so that the suture 1842 can be cut external to the body.

Figure 34:
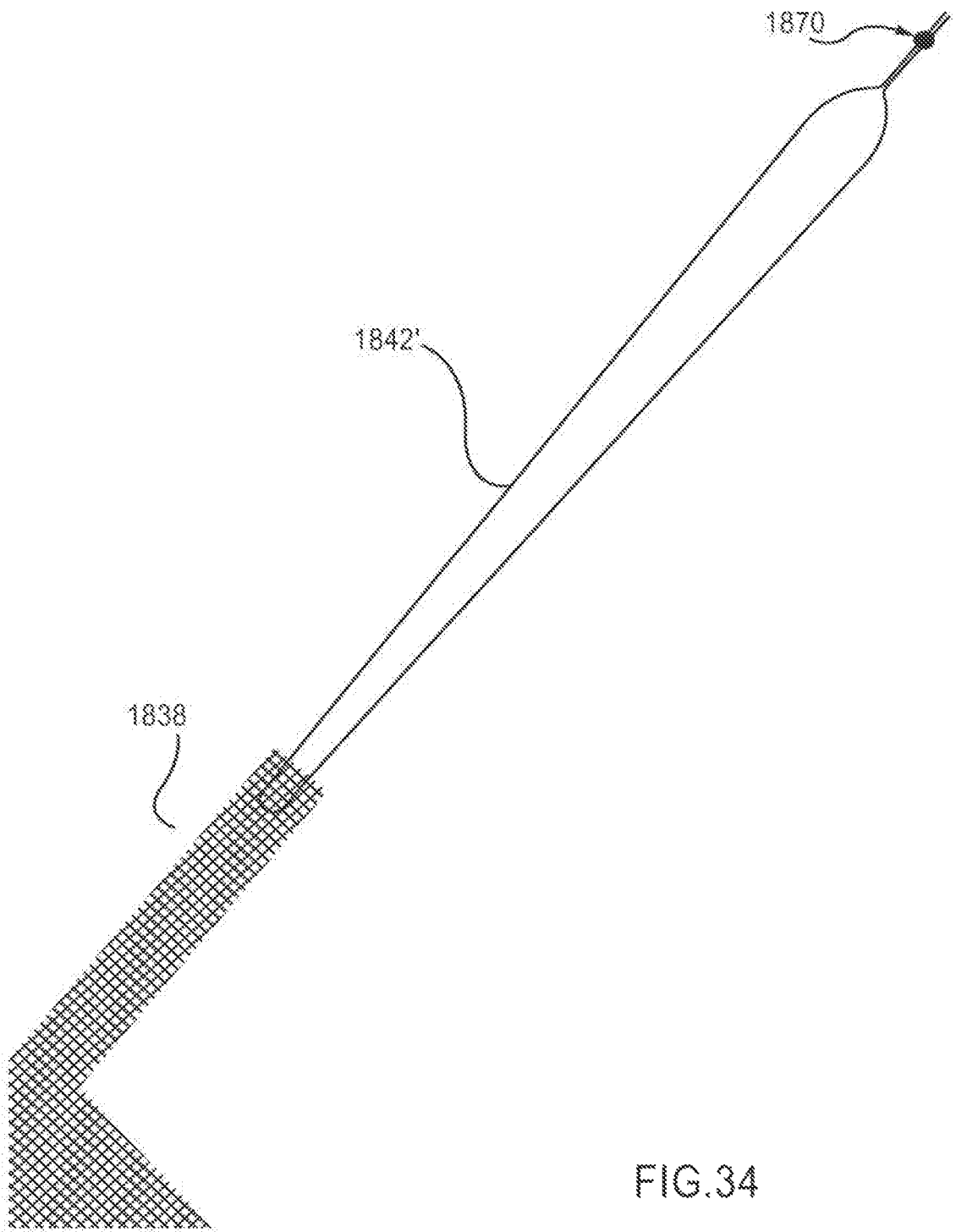

In one example, the sleeve assembly 1854 can be coupled to a strap (e.g., strap 1838), using the suture 1842. The suture 1842 is threaded through the sleeve 1826 and attached to a trailing end of the dilator 1828. A trailing end 1869 of the sleeve 1826 is positioned over the strap 1838. The tapered dilator tip 1871 is associated over a knot (not shown) formed with the suture 1842, to secure the dilator 1828 to the suture 1842. For example, the dilator 1828 can be molded or formed over the knot. FIG. 34 illustrates a portion of an alternative embodiment of a sleeve assembly, where a suture 1842' is threaded through a portion of the strap 1838 and a knot 1870 is tied to form a suture loop. A separate leader suture (not shown) can then be coupled to a leading end of the dilator.

Figure 35:
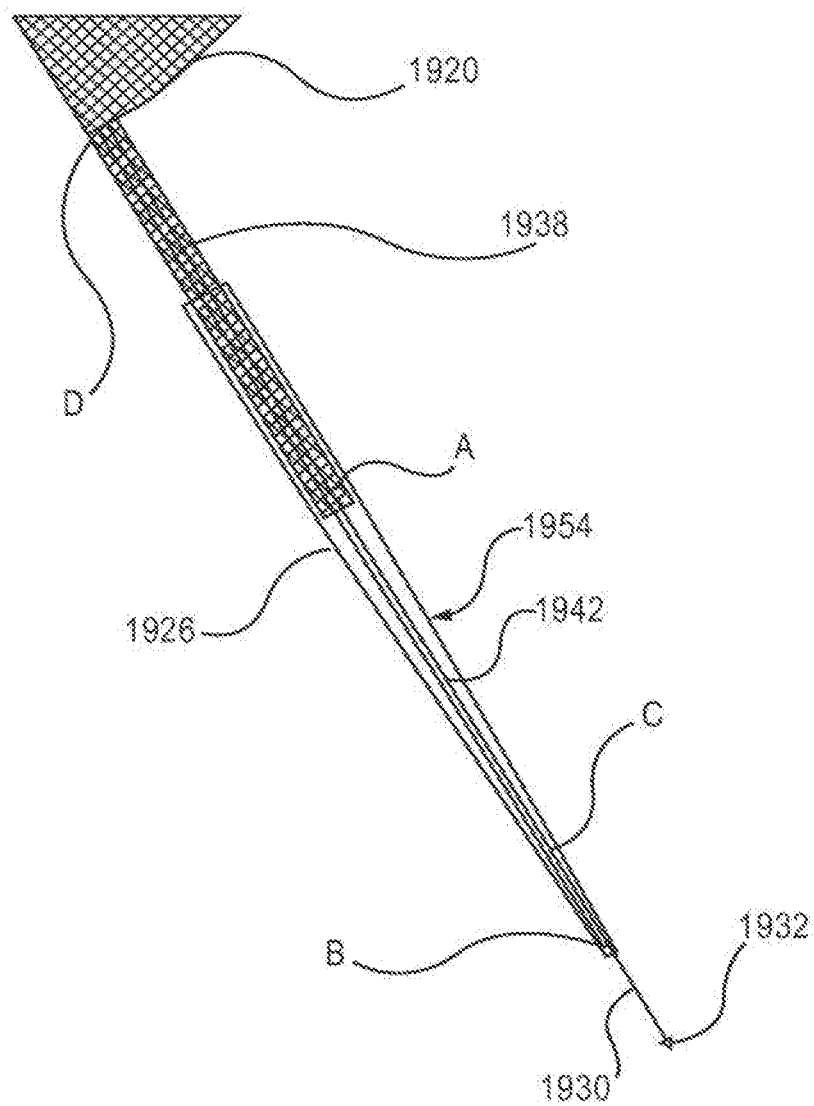

FIG. 35 illustrates a sleeve assembly that does not include a dilator. A sleeve assembly 1954 includes a sleeve 1926, a suture 1942, and a trocar needle 1932 coupled to an end of a leader 1930. The sleeve 1926 is tapered such that it can provide a lead-in through pelvic tissue and is also configured to dilate the tissue as it is being drawn through the tissue. The suture 1942 can be used to secure a strap, such as strap 1938 shown in FIG. 35, to a support portion of an implant 1920. In this embodiment, the sleeve 1926 only covers a portion of the strap 1938.

To secure the suture 1942 to the strap 1938, two ends of the suture 1942 are threaded into and near a corner of the implant 1920 at location D. The two ends are passed back through a loop formed in the suture 1942 to secure the suture 1942 to the implant 1920. The two suture ends are then threaded through the strap 1938 and tied (e.g., knotted) to the strap 1938 at intervals up to, for example, a location A. At this point, the suture 1942 is not secured to the sleeve 1926. The suture ends are then threaded through the inside of the sleeve 1926 to a location B where the suture 1942 is secured to the sleeve 1926. For example, a heat seal can be used to secure one end of the suture 1942 to the sleeve 1926. The other end of the suture 1942 exits the end of the sleeve 1926 and forms the leader 1930.

As with previous embodiments, the trocar needle 1932 that is coupled to the leader 1930 can be associated to a delivery device, such as, for example, delivery device 164, and used to deliver the implant strap to a tissue site. In the area of location C, the suture 1942 and sleeve 1926 can be cut to release the sleeve 1926 from the strap 1938. After being cut, a portion of the suture 1942 that is attached to the sleeve 1926 (at location B) is discarded. The portion of the suture 1942 that is attached to the strap 1938 at location A remains attached to the strap 1938, as the sleeve 1926 is removed. The suture portion attached to the strap 1938 at A can subsequently be used to remove a trimmed portion of the strap 1938. The suture portion attached to the implant 1920 at location D and along the strap 1938 can remain attached to the strap 1938.

In other embodiments, the suture can be coupled to the sleeve by other means. For example, the suture can be molded to a connector at location B, tied to a connector, tied to one wall of the sleeve, tied to both walls of the sleeve, or otherwise secured. In some embodiments, more than one suture can be used. The suture can optionally be disposed external to the sleeve to facilitate cutting of the suture only, and not the sleeve. For example, the sleeve can include a window or opening exposing a portion of the suture.

Figure 36:
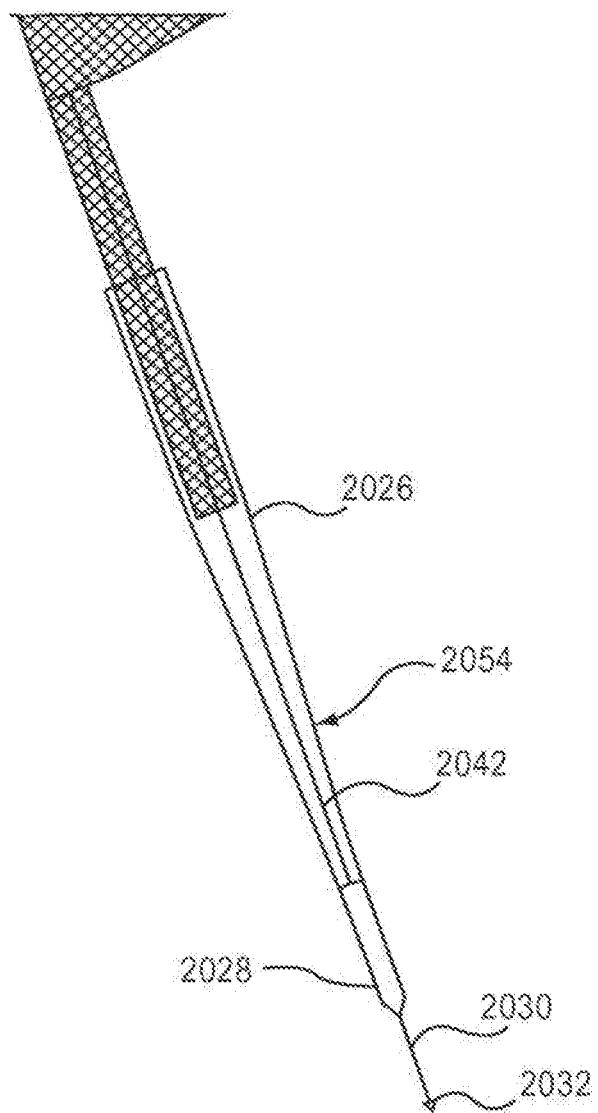

FIG. 36 illustrates a sleeve assembly that is similar to the sleeve assemblies 1854 and 1954. In this embodiment, a sleeve assembly includes a dilator to aid in dilating an insertion tract. A sleeve assembly 2054 includes a sleeve 2026, a tapered dilator 2028, a suture 2042, and a trocar needle 2032 coupled to an end of a leader 2030. The sleeve assembly 2054 is constructed the same as the sleeve assembly 1954 except for the addition of the dilator 2028. The suture 2042 can be secured to the sleeve 2026 and/or dilator 2028.

FIGS. 37-48 illustrate various embodiments of implants that can be used, for example, to repair a cystocele and a rectocele. Such implants include straps to secure an anterior support portion of an implant to an anterior region of a pelvis (e.g., to an arcus tendineus or obturator), and straps to secure a posterior support portion of the implant to a posterior region of the pelvis (e.g., a sacrospinous ligament). In some cases, an implant can be cut into two pieces to use as two separate implants, for example, an implant to be placed in an anterior region of a pelvis and an implant to be placed in a posterior region of a pelvis. Although not necessarily shown, each of the implants can be formed in part or wholly with a mesh material. The implants can include a sleeve assembly or dilator assembly disposed over one or more of the straps of the implant, as described herein, to use during the placement of the implant. The implants can alternatively include a coupling feature (e.g., on a strap) to associate a strap of the implant to a delivery device. The implants can also be secured to a pelvic tissue using sutures.

Figure 37:
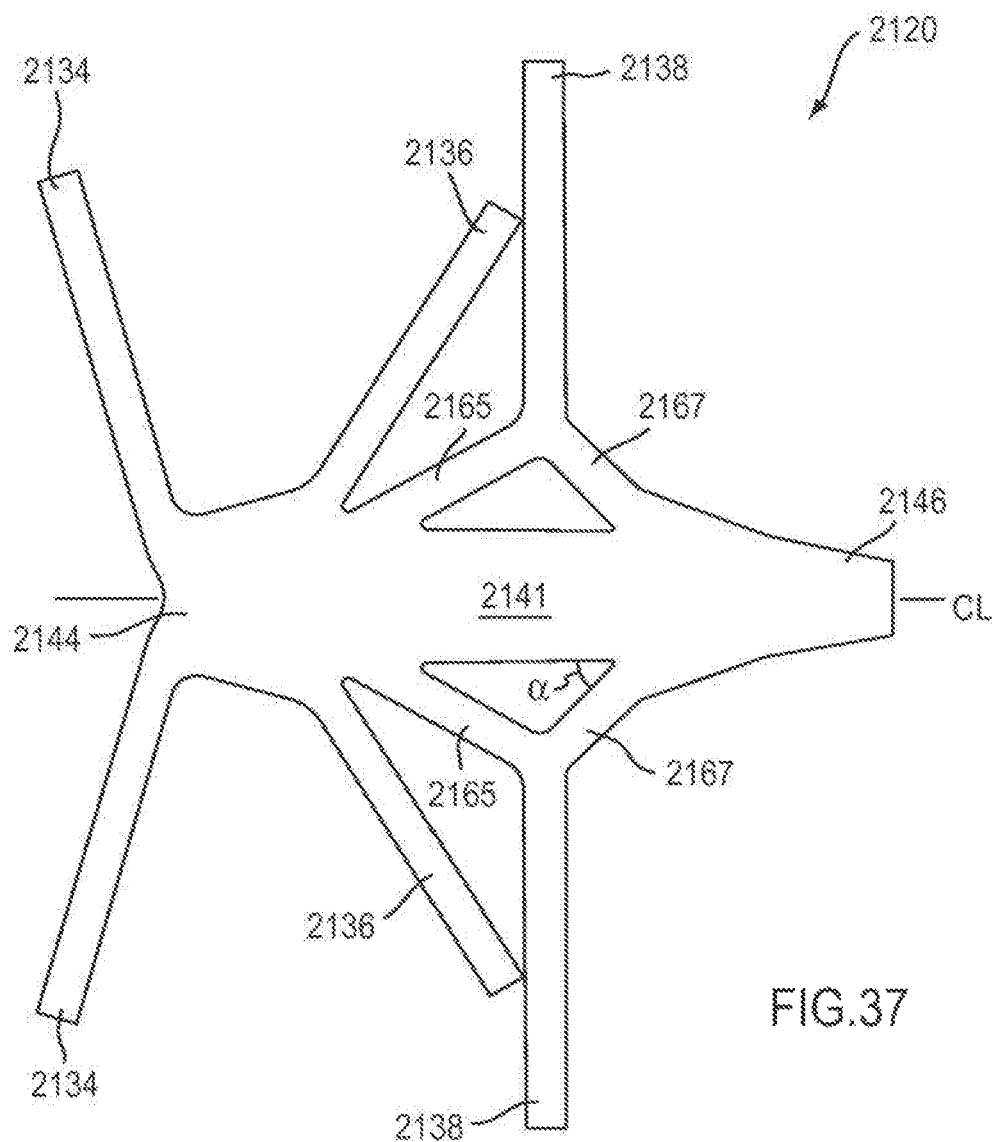
FIGS. 37 and 38 are each a top view of a different embodiment of an implant.

An implant 2120 includes two anterior straps 2134 and two mid-line straps 2136 extending from an anterior support portion 2144, and two posterior straps 2138 extending from a posterior support portion 2146. The implant 2120 also includes posterior reinforcement straps 2167 and anterior reinforcement straps 2165, which are configured to help locate and support the posterior straps 2138. In this embodiment, the posterior straps 2138 are substantially perpendicular to a centerline CL of the implant 2120, and the reinforcement straps 2167 are angled and extend toward the posterior at, for example, an angle α (relative to the centerline CL) of approximately 48 degrees. In other embodiments, reinforcement straps 2167 can be angled, for example, between about 15 and 80 degrees. Each of the different straps can be placed within a pelvic region using the methods and devices described herein. For example, the anterior straps 2134 can be secured to an arcus tendineus or an obturator (muscle or membrane), the mid-line straps 2136 can be secured to an arcus tendineus, and the posterior straps 2138 can be secured to a sacrospinous ligament. The posterior support portion 2146 can be wrapped around a vaginal cuff as described above for other embodiments. For example, the implant 2120 can be folded or curved over at a vaginal wrap portion 2141, as shown in FIG. 37.

Figure 38:
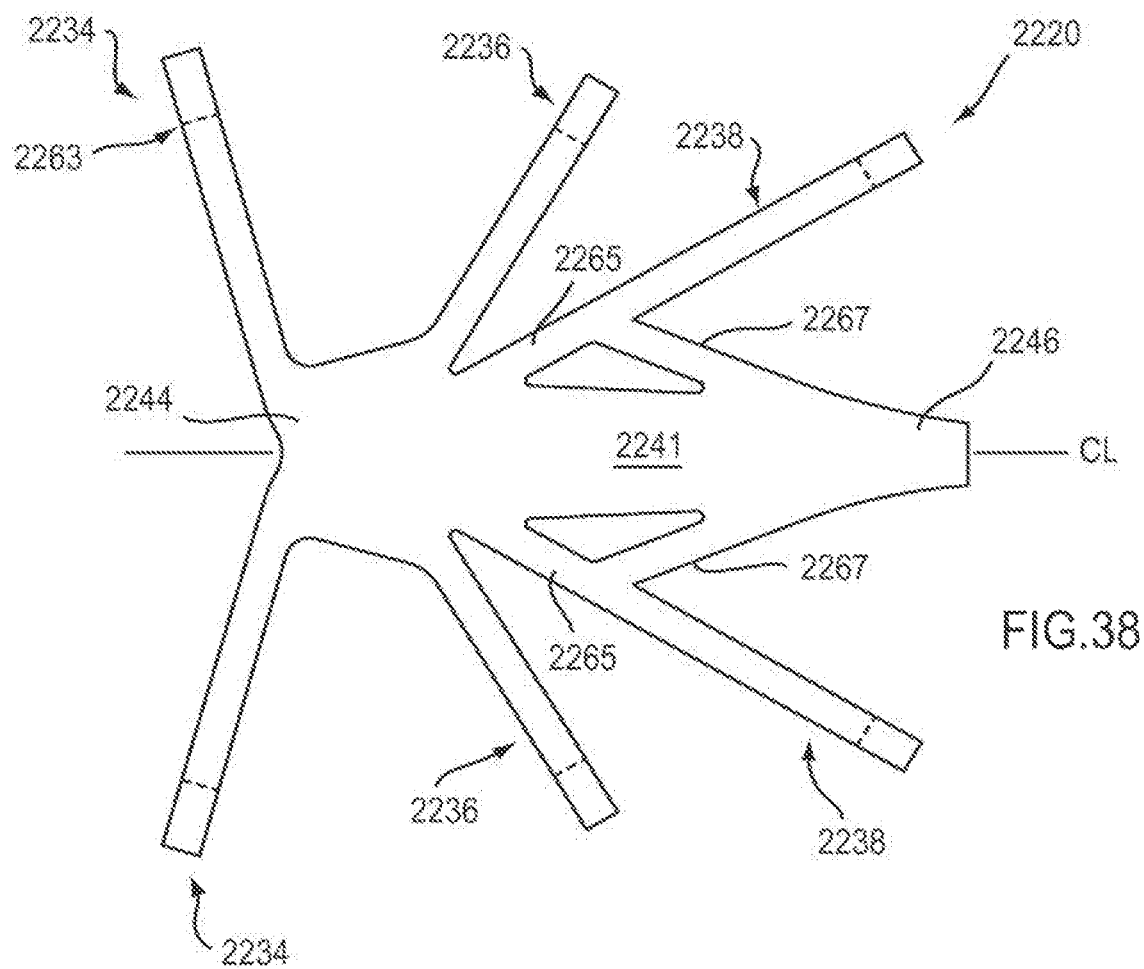

FIG. 38 illustrates another implant similar to the implant 2120 but the posterior straps are angled rather than being perpendicular with respect to a centerline of the implant. An implant 2220 includes two anterior straps 2234 and two mid-line straps 2236 extending from an anterior support portion 2244, and two posterior straps 2238 extending from a posterior support portion 2246. The implant 2220 also includes posterior reinforcement straps 2267, and anterior reinforcement straps 2265. In this embodiment, the posterior straps 2238 are angled with respect to a centerline CL of the implant 2220.

A dashed fold line 2263 is included near an end of each strap. The fold lines 2263 can be used to indicate where the straps can be associated to a dilator or sleeve device. The straps can also be folded at the fold lines 2263 to make the association to, for example, a loop connector of a dilator or sleeve device easier. The posterior reinforcement straps 2267 can provide, for example, posterior apical support. The anterior support portion 2244 can support the anterior portion of the vagina, for example, for cystocele repair. The implant 2220 can be wrapped around a vagina at location 2241 to support the vaginal cuff for example, for an enterocele repair. The posterior support portion 2246 can provide support to the posterior side of the vagina, for example, for rectocele repair. The implant 2220 can be placed and secured to pelvic tissue according to the methods described herein. For example, the anterior straps 2234 can be placed through an obturator, retro-pubically, supra-pubically or pre-pubically. The mid-straps 2236 can be placed, for example, through an arcus tendineus or distal to the ischial spine. The posterior straps 2238 can be placed, for example, through a sacrospinous ligament.

Figure 39:
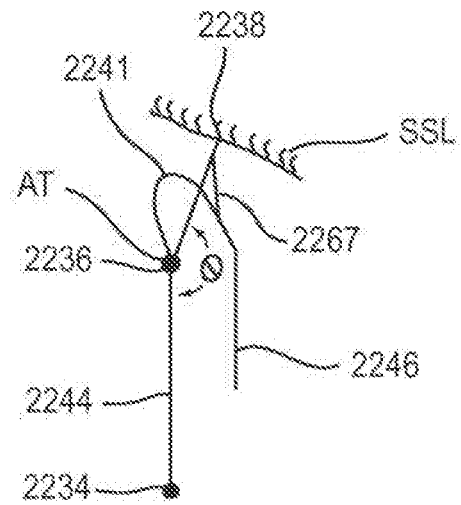
FIG. 39 is a side schematic view of the implant of FIG. 38 shown in an orientation as implanted within a pelvic region.

FIG. 39 is a schematic side-view of the implant 2220 oriented in an example position within a pelvic region. As shown, the implant 2220 can be placed in an anatomically-correct vaginal angle of support θ when the implant 2220 is secured, for example, to the arcus tendineus AT and the sacrospinous ligament SSL. FIG. 39 illustrates the attachment of straps 2234, 2236, and 2238 and the position and orientation of the posterior reinforcement straps 2267, the anterior support portion 2244, the vaginal wrap 2241 and the posterior support portion 2246.

Figure 40:
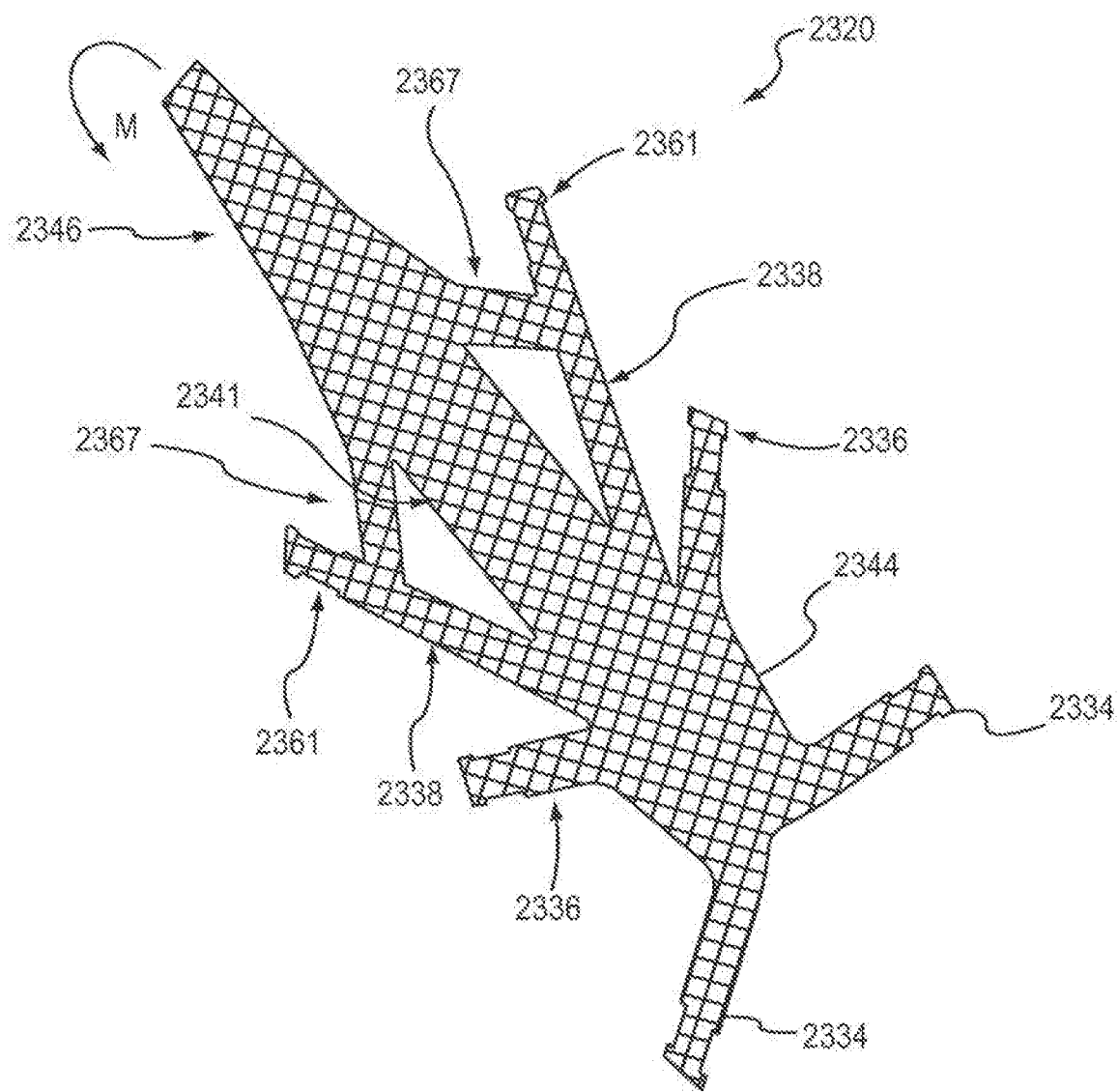
FIG. 40 is a side perspective view of an embodiment of an implant.

FIG. 40 illustrates another embodiment of an implant. An implant 2320 includes anterior straps 2334, midline straps 2336 and posterior straps 2338. The posterior straps 2338 extend from an anterior support portion 2344 and are connected to posterior reinforcement straps 2367. The posterior reinforcement straps 2367 extend from a posterior support portion 2346. Each of the straps include grooves or recessed portions 2361 to indicate where to attach to a dilator or sleeve assembly (not shown). The implant 2320 can be placed according to the methods described herein.

For example, a dilator (not shown) can be associated to a posterior strap 2338 and used to draw both the posterior strap 2338 and its associated posterior reinforcement strap 2367 through, for example, a sacrospinous ligament at the same time. The posterior straps 2338 and the posterior reinforcement straps 2367 can be used, for example, to support both the anterior support portion 2344 and the posterior support portion 2346 of the implant 2320 within the pelvic region. The posterior support portion 2346 can be tucked around the vaginal cuff and/or secured, for example, with sutures, to a posterior vaginal compartment, to provide posterior support. For example, the posterior portion 2346 can be wrapped at 2341 and tucked in a direction of arrow M shown in FIG. 40.

The anterior straps 2334 and midline straps 2336 can be secured for example, to an arcus tendineus to support the anterior support portion 2344 within the pelvic region. The anterior support portion 2344 can also optionally be further secured with sutures, to, for example, pelvic fascia or the vaginal cuff to complete an apical support.

FIGS. 41-43 illustrate an implant that is similar to the implant 120 illustrated in FIG. 3. An implant 2420 includes anterior straps 2434 and middle straps 2436 that extend from an anterior support portion 2444, and posterior straps 2438 that extend from a posterior support portion 2446. A vaginal wrap portion 2441 is disposed between the anterior support portion 2444 and posterior support portion 2446. The implant 2420 can be placed in a pelvic region using methods and devices disclosed herein. The straps 2434, 2436, 2438 can include tangs as described above and/or can include barbs or other protrusions configured to engage tissue. The anterior straps 243 also include dimples 2440 configured to increase the holding strength of the anterior straps 2434.

FIG. 42 is an enlarged view of an anterior strap 2440, and FIG. 43 is an enlarged side view of a portion of a strap 2434 illustrating a profile of the dimples 2440. As shown in FIG. 43, the dimples 2440 are disposed in alternating, opposed directions on the top and bottom surfaces of the strap 2434. The number of dimples 2440 can vary and can also be included on other straps of the implant and/or some or all of the support portions 2444 and 2446. The dimples 2440 can be sized and shaped as described above for implant 120.

Figure 44:
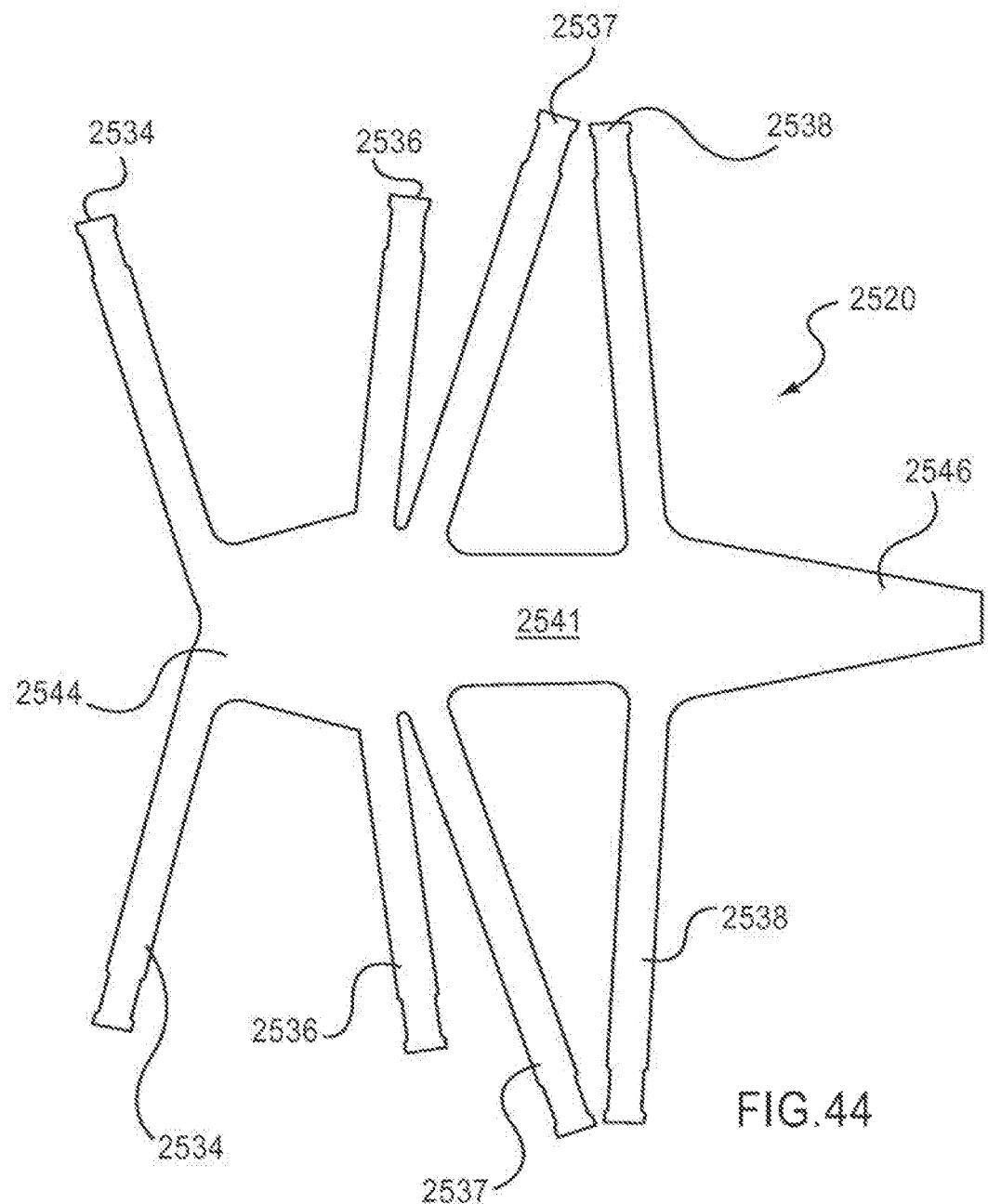
FIGS. 44-46 are each a top view of a different embodiment of an implant.

FIG. 44 illustrates an embodiment of an implant having eight straps. An implant 2520 includes six straps extending from an anterior support portion 2544 and two posterior straps 2538 extending from a posterior support portion 2546. The straps extending from the anterior support portion 2544 include anterior straps 2534, first or anterior midline straps 2536 and second or posterior midline straps 2537. The implant 2520 also includes a vaginal wrap portion 2541 disposed between the posterior support portion 2546 and the anterior support portion 2544.

The various straps of the implant can be placed within a tissue site individually as described in previous embodiments, or alternatively the posterior straps 2538 can be combined with second midline straps 2537 (on one side of the implant) and placed together at a tissue site within a pelvic region. The posterior straps 2538 and second midline straps 2537 on the contra-lateral side can likewise be combined for placement. For example, the posterior straps 2538 and second midline straps 2537 can be combined and passed through a sacrospinous ligament. The anterior straps 2534 and first midline straps 2536 can be placed according to methods disclosed herein.

Figure 45:
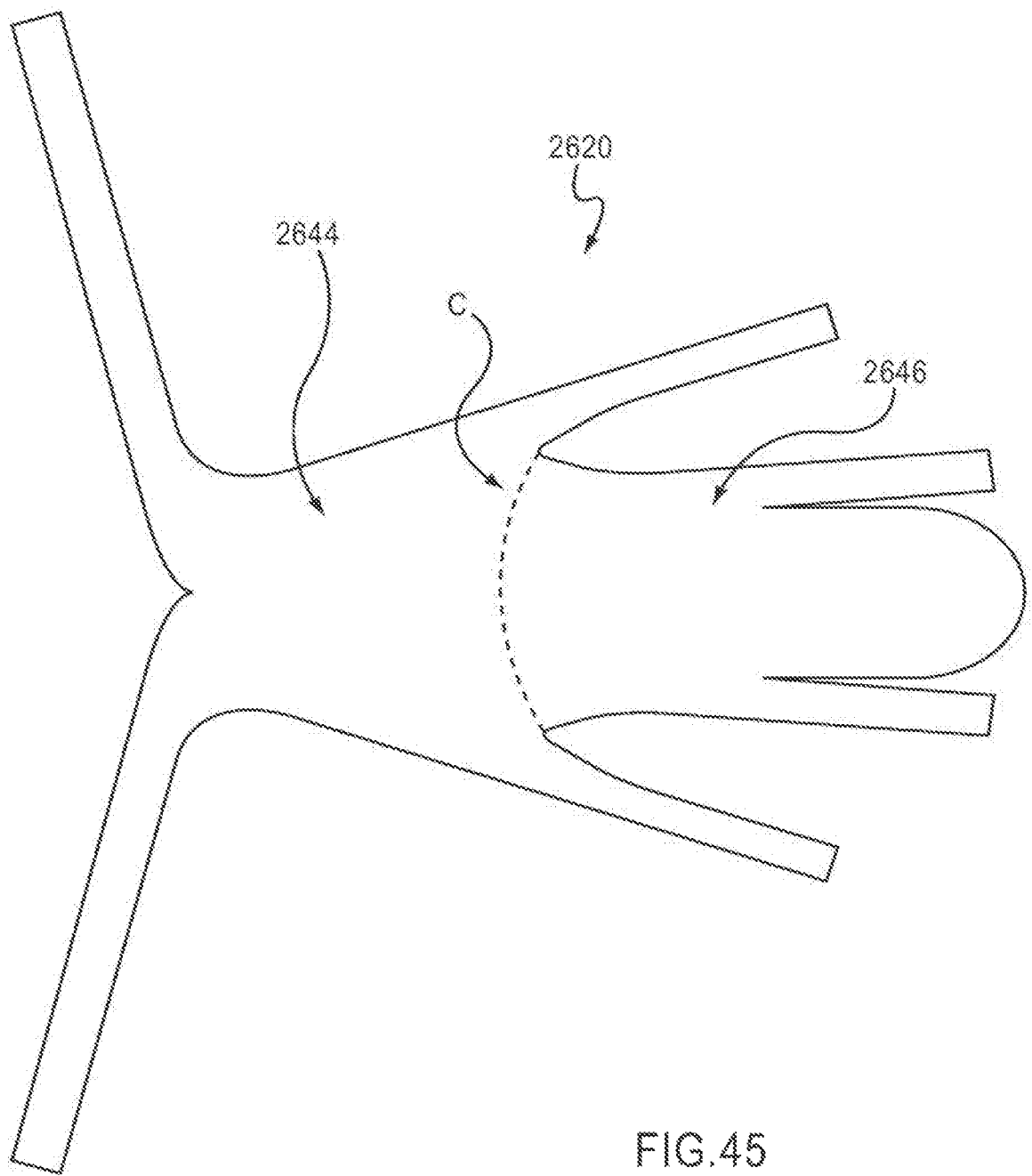

FIG. 45 illustrates an implant 2620 that can be placed within a pelvic region in its entirety, or can be cut, for example, along a dashed line C to form a posterior repair implant 2646 and an anterior repair implant 2644. When implant 2620 is cut, both anterior repair implant 2644 and posterior repair implant 2646 can be individually placed into a pelvic region of a patient as needed for the particular condition. Alternatively, a portion of the implant not used can be discarded or saved for a later use. The versatility of implant 2620 allows a physician flexibility in fashioning the most appropriate procedure for the patient. The various straps of the implant 2620 can be placed according to the methods and devices described herein.

Figure 46:
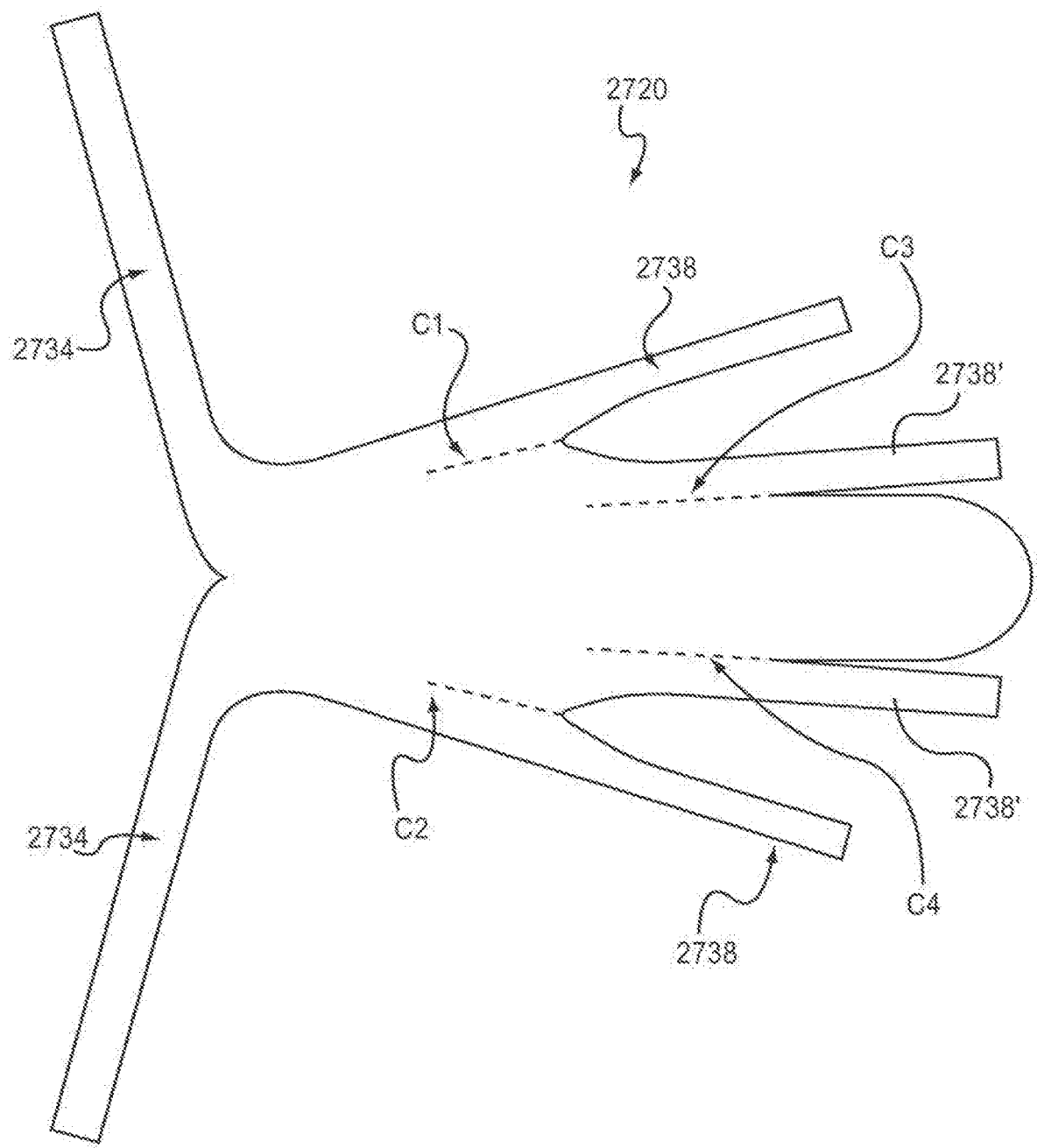

FIG. 46 illustrates another embodiment of an implant having six straps. An implant 2720 includes a pair of anterior straps 2734 and four posterior straps 2738, 2738'. Similar to the implant 1320 (FIG. 27) the implant 2720 can be adjusted to fit a particular patient. The implant 2720 includes dashed cut lines C1, C2, C3, C4 that indicate example locations where the implant 2720 can be cut, either entirely or partially, to fit the patient. For example, as described above for implant 1320, cutting the implant along lines C1 and C2 allows the posterior straps 2738 to be pulled further into a tissue. Cutting along lines C3 and C4 allows the posterior straps 2738' to be pulled further into tissue. The posterior straps 2738' can be anchored, for example, to a sacrospinous ligament (SSL) or an arcus tendineus, or can be removed (cut-off) from the implant 2720. Similarly, posterior straps 2738 can be anchored to the arcus tendineus or the SSL, or can be removed from the implant 2720. In one example modification of the implant 2720, if the posterior straps 2738' are removed (e.g., cut off), implant 2720 can optionally be anchored to the arcus tendineus using straps 2738, rather than securing the straps 2738 to the SSL. In another example, if the posterior straps 2738 are removed, the implant 2720 can be anchored, for example, to the SSL, using the straps 2738'. Implant 2720 can be placed within a pelvic region using the methods and devices described herein.

Figure 47:
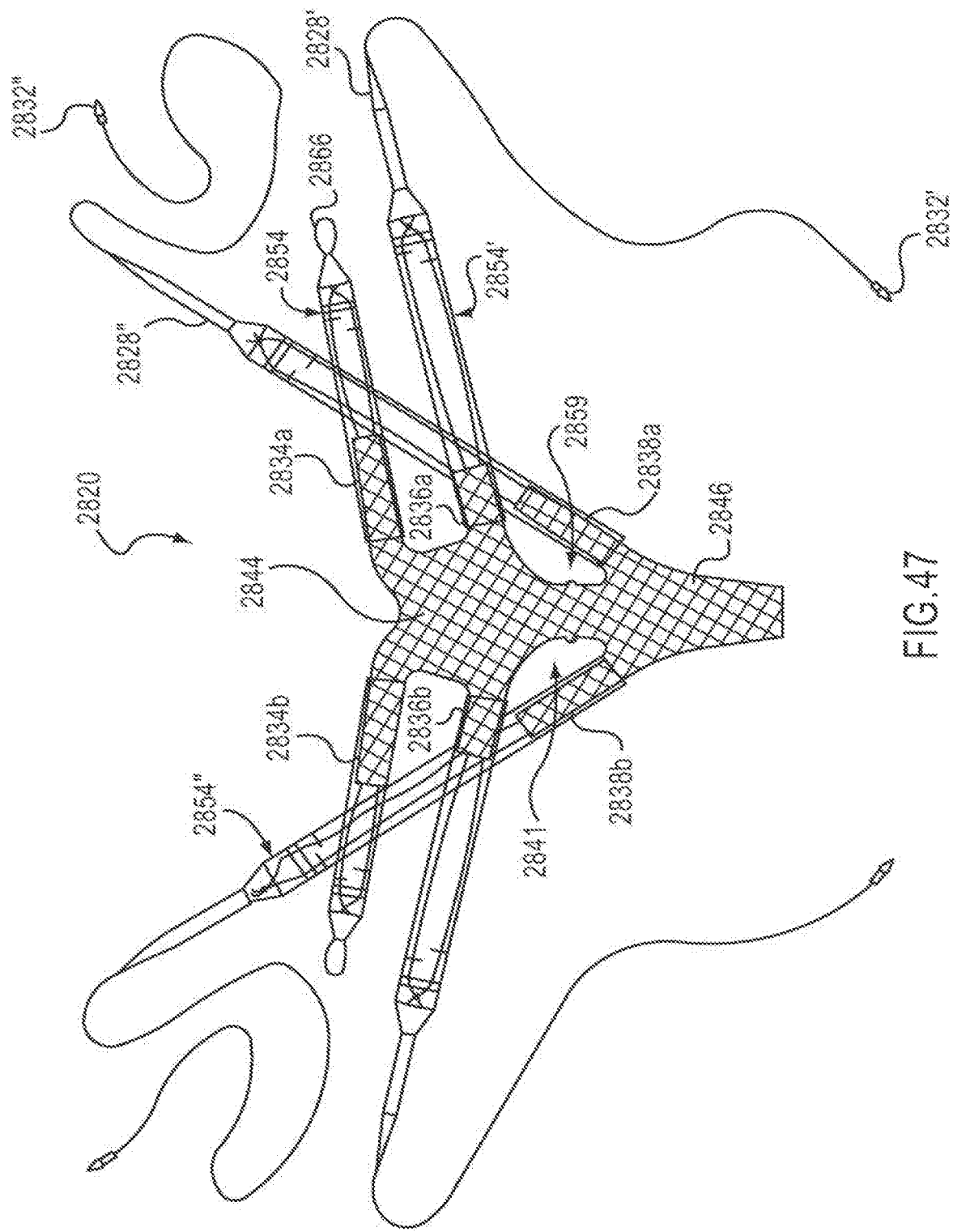
FIG. 47 is a top view of another embodiment of an implant.

FIG. 47 illustrates an implant having sleeve assemblies attached to its six straps. An implant 2820 includes anterior straps 2834a, 2834b and midline straps 2836a, 2836b extending from an anterior support portion 2844, and posterior straps 2838a, 2838b extending from a posterior support portion 2846. Various embodiments of a sleeve assembly are disposed over the straps. The sleeve assemblies are similar to those described herein. For example, the sleeve assembly 2854 disposed over strap 2834a (and 2834b) is similar to the sleeve assembly described with reference to FIG. 9. The sleeve assembly 2854 includes a loop connector 2866 to associate to a delivery device having an engagement notch, such as delivery device 264. The sleeve assembly 2854' disposed over strap 2836a (and 2836b) and the sleeve assembly 2854" disposed over strap 2838a (and 2838b) are each similar to the sleeve assemblies described with reference to FIG. 23 and FIG. 33. The sleeve assemblies 2854' and 2854" each include a dilator 2828', 2828" and a trocar needle 2832', 2832" to associate to a delivery device such as delivery device 164. As described above for previous embodiments, each of the straps of the implant 2820 are shorter in length than its surrounding sleeve, reducing the need to trim the length of the strap after placement.

Implant 2820 can also be cut into an anterior repair implant and a posterior repair implant as described above with reference to FIG. 45. In this embodiment, protrusions 2859 are provided on lateral sides of a vaginal wrap portion 2841 of the implant 2820 to indicate a cut location for separating the anterior support portion 2844 from the posterior support portion 2846. For example, when a patient has a uterus, the total repair implant 2820 can be separated (cut into two parts) and the anterior support portion 2844 and posterior support portion 2846 can each be positioned separately, rather than wrapping the posterior support portion 2846 around the vaginal cuff of a hysterectomy patient.

Figure 48:
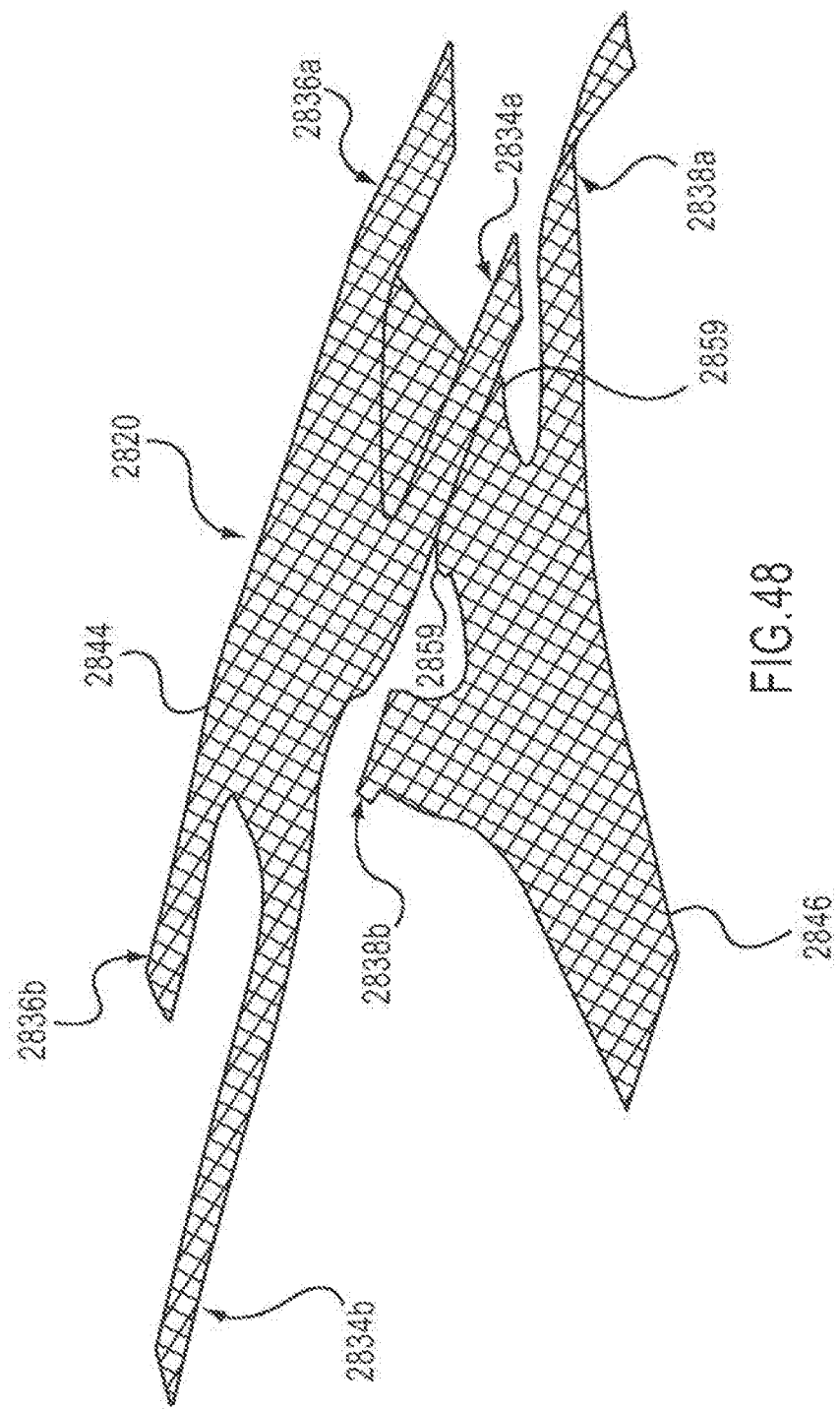
FIG. 48 is a side perspective view of the implant of FIG. 47 shown in an orientation as implanted within a pelvic region.

FIG. 48 illustrates a three-dimensional view of the implant 2820 simulating a deployed configuration within a patient. The position of implant 2820 illustrated in FIG. 48 can be obtained, for example, by securing the mid-straps 2836a, 2836b to an arcus tendineus (on opposite sides of a pelvis, the anterior straps 2834a, 2834b to an obturator muscle or membrane (on opposite sides of the pelvis) and the posterior straps 2838a, 2838b to a sacrospinous ligament (on opposite sides of the pelvis). The posterior support portion 2846 is shown after being wrapped around a vaginal cuff and positioned to provide support to the posterior side of the vagina.

As shown in FIG. 47, prior to placing the implant 2820 within a pelvic region, the posterior straps 2838a and 2838b are angled toward the anterior straps 2834a, 2834b and the mid straps 2836a, 2836b. When, however, the implant 2820 is deployed within a pelvic region and the posterior support portion 2846 is wrapped around a vaginal cuff (e.g., of a hysterectomy patient), the posterior straps 2838a, 2838b are angled in a direction of the sacrospinous ligaments (SSL) as shown in FIGS. 48 and 49.

Figure 49:
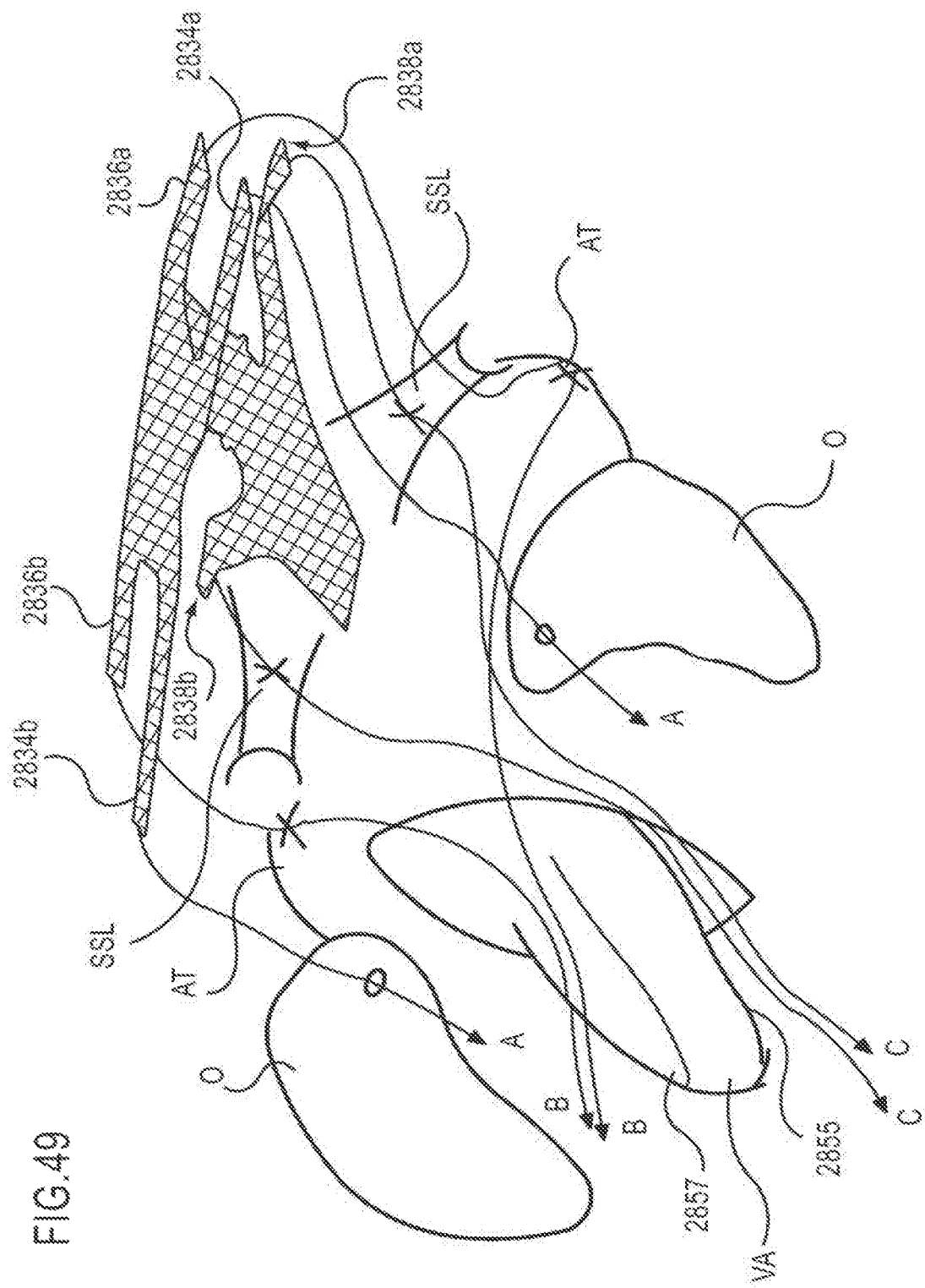
FIG. 49 is a side perspective view of the implant of FIG. 47 shown partially disposed within a schematic illustration of a portion of a pelvic region.

FIG. 49 illustrates the deployment of the implant 2820 within a schematic illustration of a pelvic region. The procedure described applies to securement of straps of the implant 2820 on both sides of the pelvic region. FIG. 49 illustrates the implant 2820 without the sleeve assemblies attached to the straps. Implant 2820 is configured to be delivered in a collapsed configuration through an anterior and/or posterior vaginal incision. For example, an anterior incision 2857 is made in a vagina and the implant 2820 is placed though the incision 2857. The anterior straps 2834a, 2834b are pulled through the obturator foramen O and the sleeve assemblies (not shown) coupled to the straps 2834a, 2834b can be pulled out through the anterior incision 2857, as shown by the directional arrows A in FIG. 49. An insertion tool such as delivery device 264 can be used for the placement of the anterior straps 2834a, 2834b. An apical stitch can also optionally be made from a midline of implant 2820 to the vaginal apex VA.

The midline straps 2836a, 2836b can be pulled through an arcus tendineus AT using a suturing device, such as delivery device 164, and the respective sleeve assemblies (not shown) can be pulled out through the anterior incision 2857, as indicated by the directional arrows B.

A posterior vagina incision 2855 can then be made for access to secure the posterior straps 2838a, 2838b and position the posterior support portion 2946. Alternatively, the posterior straps 2838a, 2838b and posterior support portion 2946 can be secured via access through the anterior incision. The posterior support portion 2846 can be wrapped around the posterior side of the vagina. The posterior straps 2838a, 2838b can be pulled through a sacrospinous ligament SSL using a suturing device, such as delivery device 164, and the respective sleeve assemblies (not shown) can be pulled out through the posterior incision 2855, as indicated by the directional arrows C.

When all of the sleeve assemblies have been pulled out through either the anterior incision 2857 or posterior incision 2855, the implant 2820 can be adjusted and centered by pulling the sleeve assemblies until a desired implant position is achieved. When the implant 2820 is positioned correctly, the straps of the implant are released from the sleeve assemblies in a manner as previously described (e.g., by cutting the sleeve and/or suture and pulling the sleeve assembly off the strap). Anterior straps 2834a, 2834b can be trimmed externally to the body, as necessary.

Other embodiments of sleeves and/or dilator assemblies can alternatively be used. In some embodiments, the dilators and sutures with bullet/trocar needles can be replaced with a delivery tube configured for use with, for example, the BSC Advantage® or the Prefyx™ delivery devices and their respective delivery approaches. In some embodiments, the midline straps 2836a, 2836b are removed. In such an embodiment, the implant 2820 can be secured, for example, to the arcus tendineus with the anterior straps 2834a, 2834b and/or the anterior support portion 2844 can be attached to the arcus tendineus using separate sutures.

FIGS. 50-55 each illustrate a different embodiment of an implant. that can be used, for example, to treat a rectocele, or provide support to a posterior side of a vagina. These are merely examples of the possible uses of the implants of FIGS. 50-55, as other uses of the implants are also possible. An implant can include straps to secure a posterior support portion of the implant to, for example, sacrospinous ligaments. An implant can include a vaginal wrap portion as described above for the total repair implants that can be wrapped around a vaginal cuff or an apical portion of a vagina. Although not necessarily shown in FIGS. 50-55, each of the implants can be formed in part or wholly with a mesh material. The implants can include a sleeve assembly or dilator assembly disposed over one or more of the straps, as described herein, for use during the placement of the implant. The implants can alternatively include a coupling feature to associate a strap of an implant to a delivery device. The implants can also or alternatively be secured to a tissue using sutures.

Figure 50:
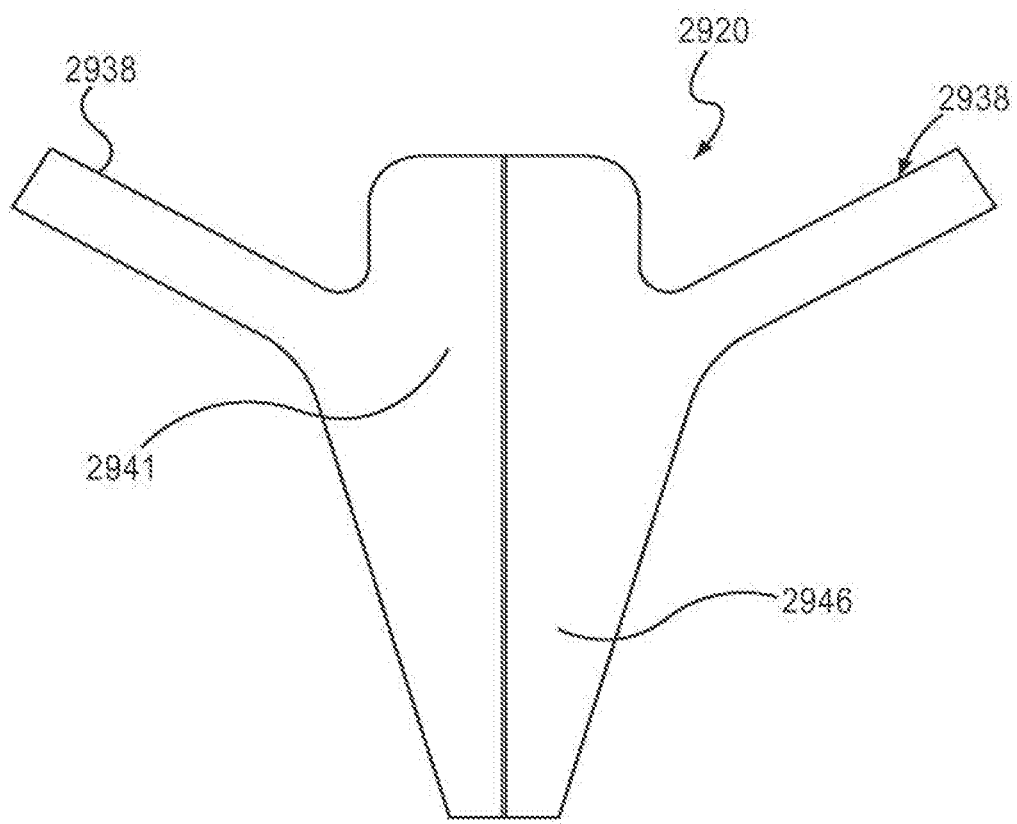
FIGS. 50-52 are each a top view of a different embodiment of an implant.

As shown in FIG. 50, an implant 2920 includes a posterior support portion 2946 and two posterior straps 2938 that can each be secured, for example, to a sacrospinous ligament. The implant 2920 also includes a vaginal wrap portion 2941 that can be wrapped around a vaginal cuff or apical area of a vagina as described above for previous embodiments.

Figure 51:
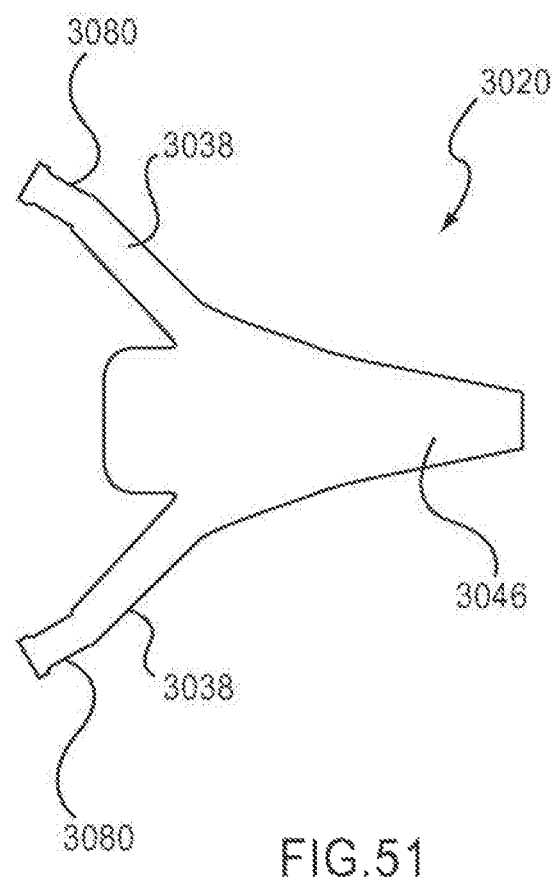

FIG. 51 illustrates an implant 3020 that is similar to the implant 2920. In this embodiment, the implant 3020 includes a posterior support portion 3046 and two posterior straps 3038 that include grooves 3080 that can be used to facilitate association of the respective strap to, for example, a dilator device. As with the previous embodiment, posterior straps 3038 can be placed into a sacrospinous ligament for anchoring. The implant 3020 can also be wrapped around a vagina as described above.

Figure 52:
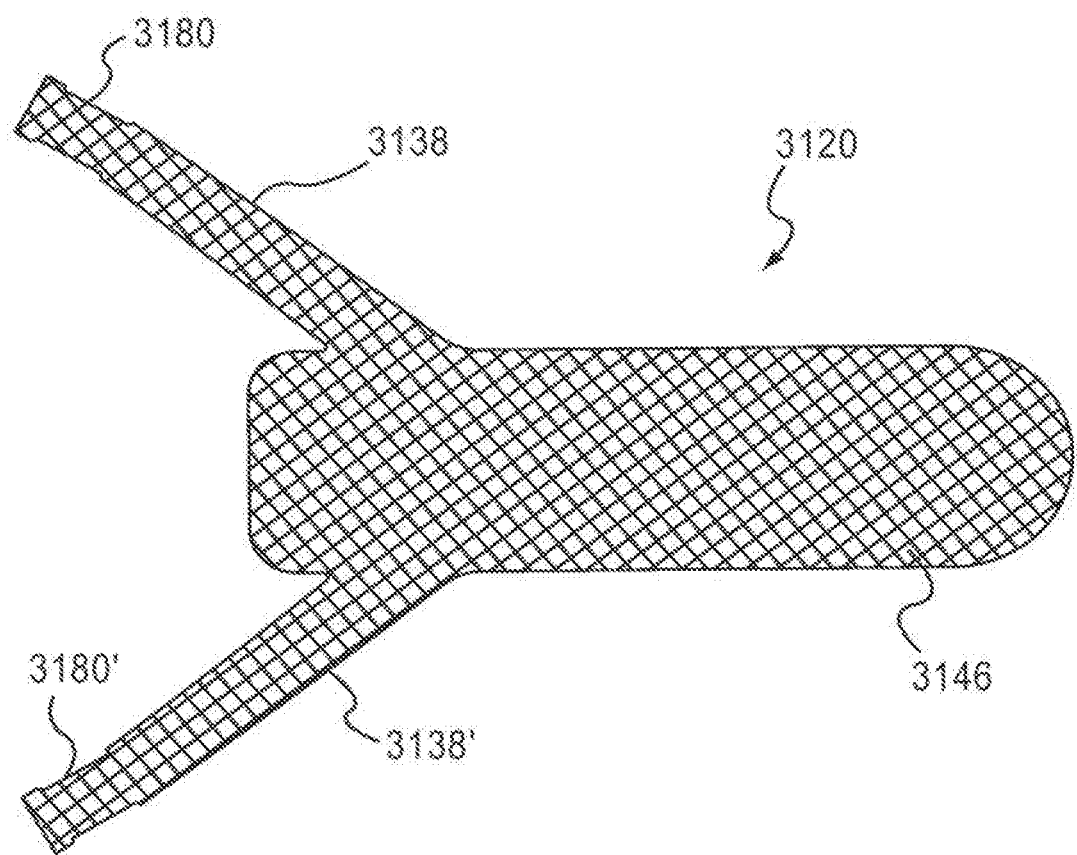
Figure 53:
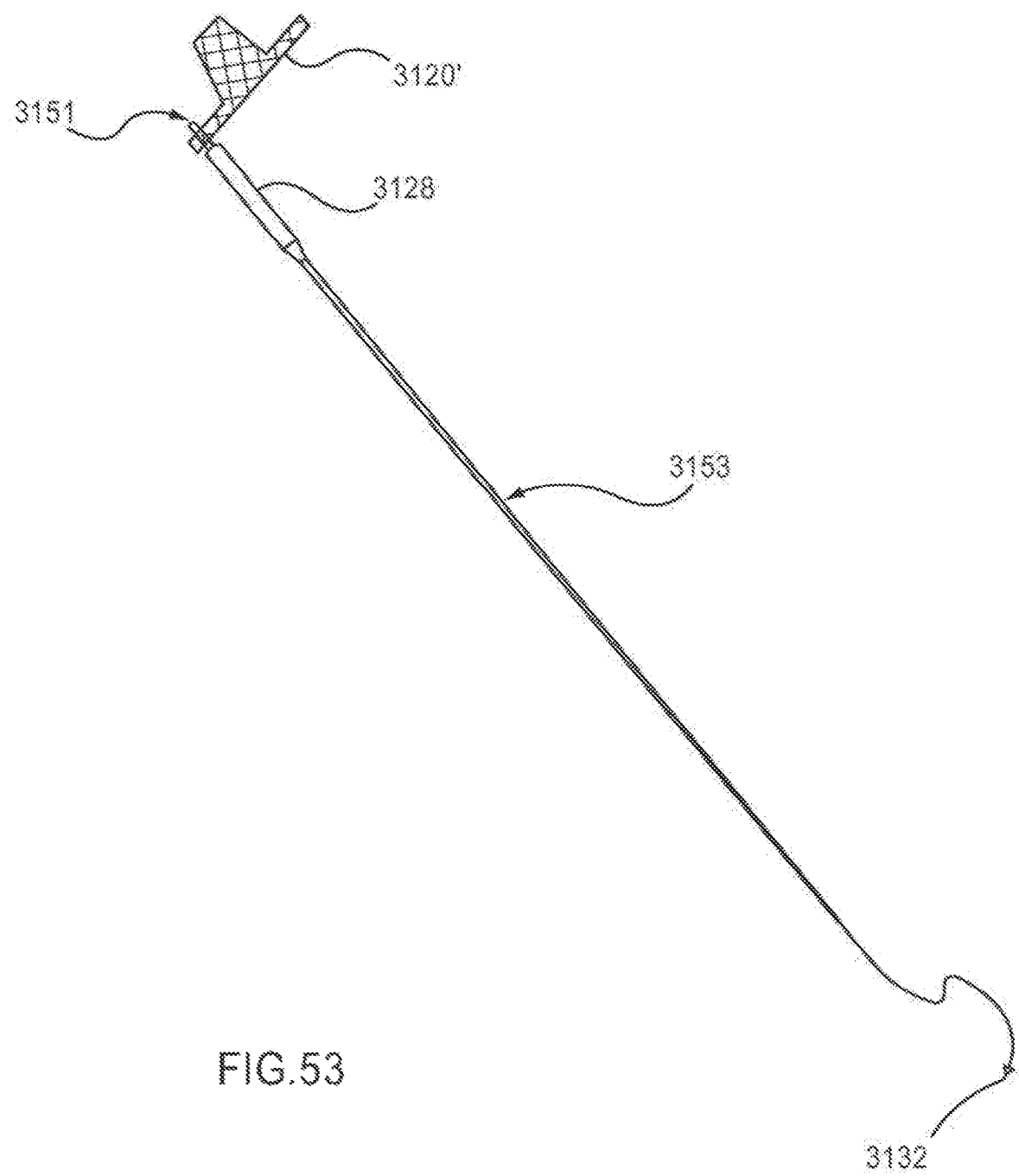
FIG. 53 is a top view of an implant coupled to a dilator device.

FIG. 52 illustrates an implant 3120 that is similar to the implant 3020. The implant 3120 includes a posterior support 3146 and two posterior straps 3138, 3138' that include grooves 3180, 3180' to facilitate association of the respective strap to, for example, a dilator device. Posterior straps 3138, 3138' can each be anchored, for example, to a sacrospinous ligament (SSL). FIG. 53 illustrates a dilator device 3153 that can be used to pull the straps 3138, 3138' through a tissue. The dilator device 3153 includes a tapered dilator 3128 and a loop connector 3151. A strap of an implant 3120' is shown placed through the loop connector 3151 to secure it to the dilator device 3153. The dilator device 3153 can be associated to a delivery device, such as delivery device 164, with a trocar needle 3132. The dilator device 3153 can be used to pull a strap of an implant through a pelvic tissue in the same manner as described above for the sleeve assemblies.

Figure 54:
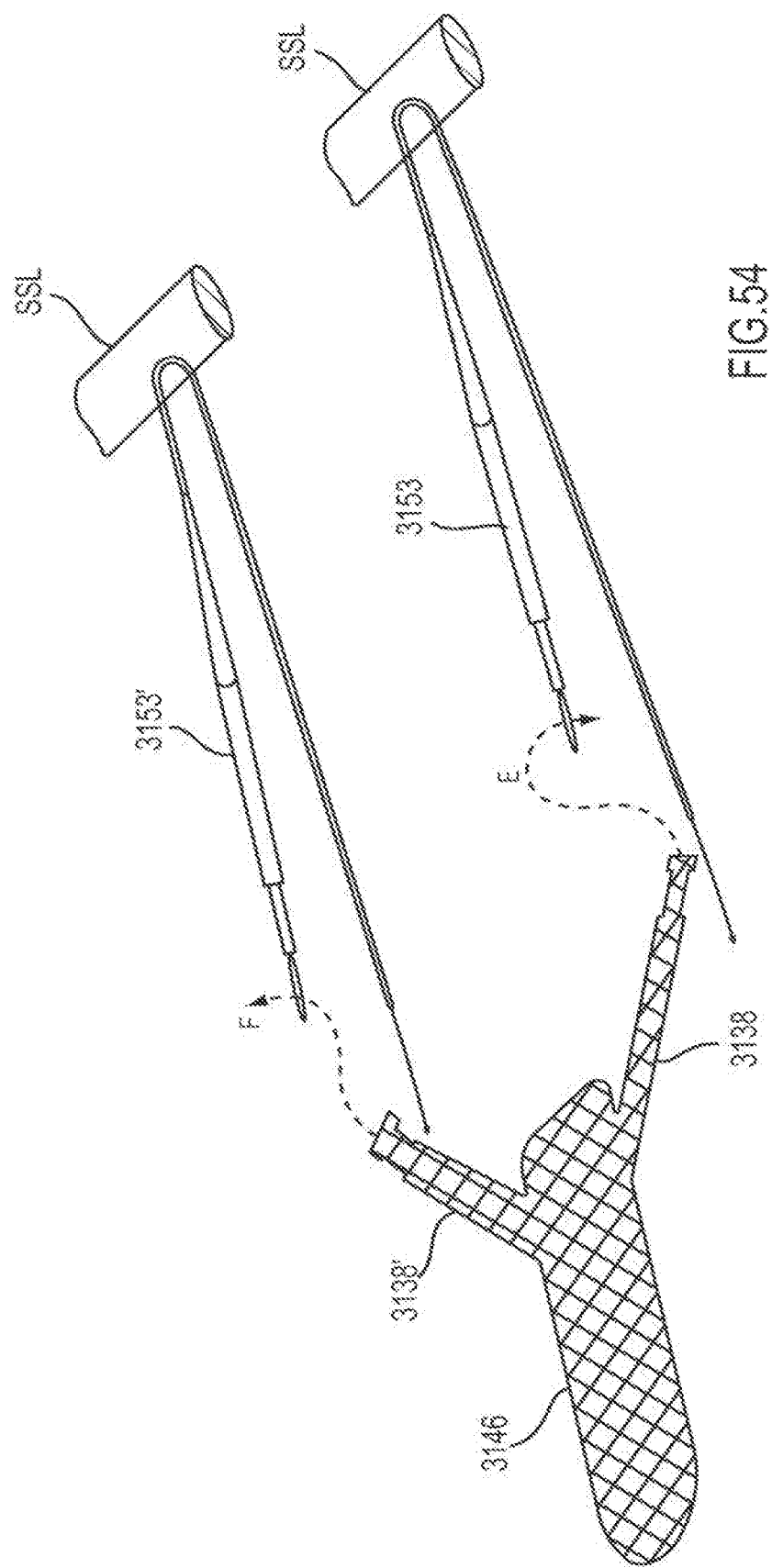
FIG. 54 is a perspective view of the implant of FIG. 52 shown partially disposed within a schematic illustration of a portion of a pelvic region.

FIG. 54 illustrates a pair of dilator devices 3153, 3153' after being passed through a schematic representation of sacrospinous ligaments SSL using for example, a delivery device 164. For example, the dilator devices 3153 and 3153' can be passed through an anterior or a posterior vaginal incision and pulled through an SSL on contra-lateral sides of a pelvic region. The straps 3138, 3138' can each be placed through the loop connectors 3151, 3151' of the respective dilator devices 3153, 3153' as indicated by the directional arrows E and F, respectively. The dilator devices 3153, 3153' can then be used to pull the straps 3138, 3138' through the sacrospinous ligaments. Alternatively, the straps can be coupled to the dilator devices prior to inserting the dilator devices into a pelvic region.

Figure 55:
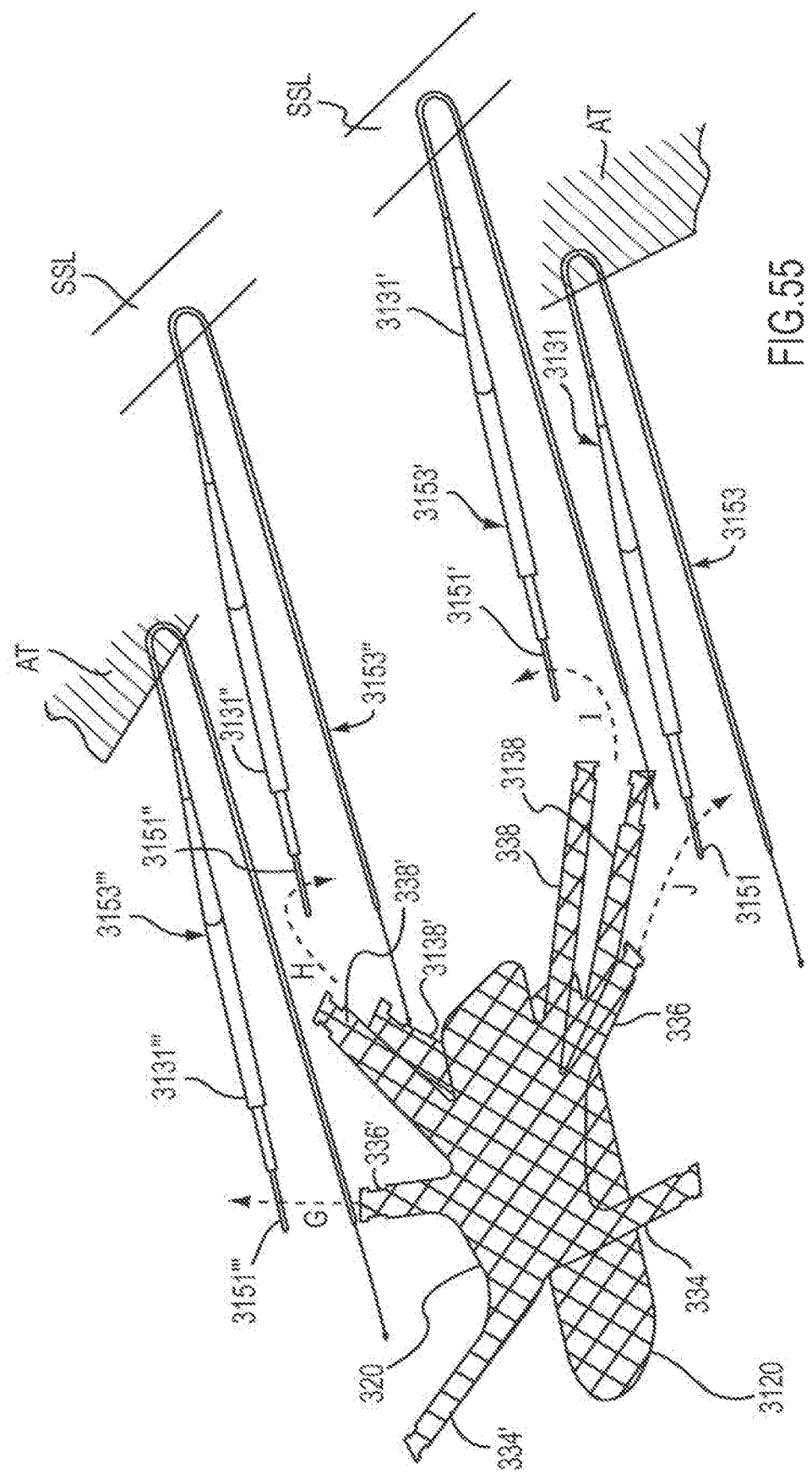
FIG. 55 is a side perspective view of four dilator devices and the implants of FIGS. 11 and 52 shown disposed within a schematic illustration of a portion of a pelvic region.

FIG. 55 illustrates the use of dilator devices to deliver both the implant 320 shown in FIG. 12, and the posterior implant 3120 at the same time. A schematic representation of the sacrospinous ligaments SSL and the arcus tendineus AT are also illustrated in FIG. 55. The straps 338, 338' on implant 320 and the straps 3138, 3138' on implant 3120 are combined and placed through the loops 3151' and 3151" on the dilator devices 3153' and 3153", respectively, as indicated by the paths of directional arrows 1 and H, respectively. A slidable tube member 3131', 3131" can then be slid over the loops 3151' and 3151" in the same manner as described above with reference to FIG. 13. The dilator devices 3153' and 3153" can then be used to pull the straps 338, 3138 and the straps 338', 3138' through the sacrospinous ligaments SSL on each side of a pelvic region. Placing two straps (e.g. 338, 3138) through a tissue (e.g., the SSL) with one dilator at the same time reduces the procedure time as well as reduces damage to the SSL during the delivery process. The dilator devices can be placed in the SSL by either an anterior or posterior vaginal incision.

The straps 336, 336' of the implant 320 can be placed through the loops 3151 and 3151''' of the dilators 3153 and 3153''', respectively, as indicated by the paths of the directional arrows J and G, respectively. Slidable tube members 3131 and 3131''' of the dilators 3153 and 3153''', respectively, can then be slid over the loops 3151 and 3131''', respectively, as described above. The dilators 3153 and 3153''' can then be used to pull the straps 336, 336' through, for example, the arcus tendineus AT on each side of a pelvic region. The straps 334, 334' can be delivered in a similar manner or using any of the devices described herein. The straps 334, 334' can be secured, for example, to the arcus tendineus or an obturator.

Figure 56:
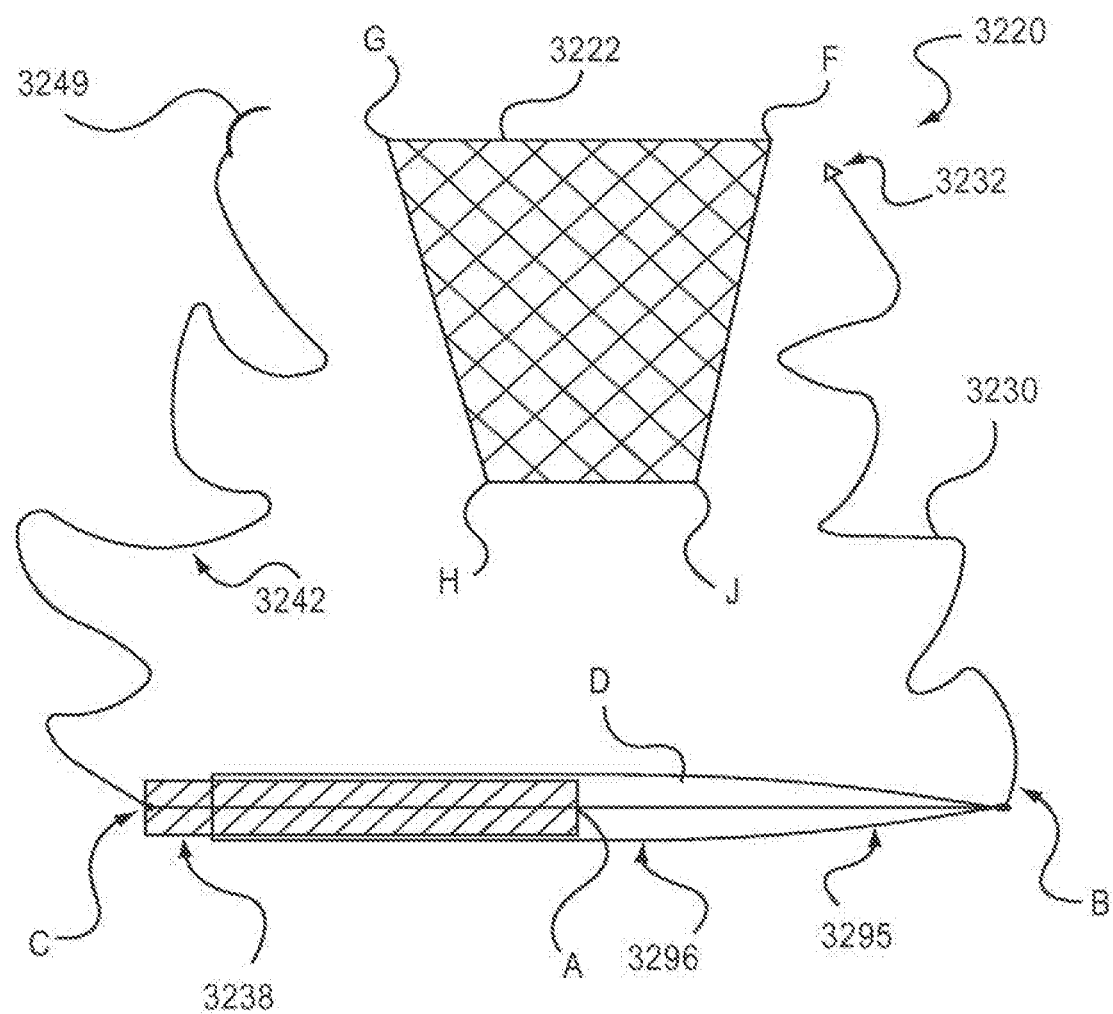
FIG. 56 is a top view of another embodiment of an implant shown unassembled.

FIG. 56 illustrates an embodiment of an implant unassembled. A user (e.g., a physician, or medical professional) can select an implant support portion and a suitable sleeve and strap assembly, and assemble them as needed. An implant 3220 can be assembled such that it is configured similar to the implant 1420 described above with reference to FIG. 28. The implant 3220 includes a support portion 3222 having four corners G, F, H, J. Although only a single sleeve and strap assembly 3296 is shown, it should be understood that more than one sleeve and strap assembly can be coupled to the support portion 3222, for example, at one or more of the corners G, F, H, J. For example, an implant can be assembled with a sleeve and strap assembly coupled at each of the corners G and F to form an implant. In another example, a sleeve and strap assembly can be coupled to corners H and J, to form another embodiment of an implant. To assemble the implant 3220, a user can cut to size and assemble the implant to his or her preference (e.g., in a sterile environment).

The strap and sleeve assembly 3296 includes a strap 3238, a sleeve 3295, a suture 3242, a trocar needle 3232 and a curved needle 3249. The suture 3242 is knotted or otherwise secured to an exposed portion of the strap 3238 at point C, threaded in and out of the strap 3238 to point A where it is again secured to the strap 3238 (e.g., by tying a knot). The suture 3242 can also be knotted intermittently along the strap 3238 between points C and A. The suture 3242 continues from point A inside the sleeve 3295 to point B where it is secured and exits the sleeve 3295. The suture extends from the sleeve forming a leader 3230 to which the trocar needle 3232 is attached. The curved needle 3249 is secured to the suture 3242 and can be used to sew or stitch the strap 3238 to the support portion 3222, for example, at corner G. After the sleeve and strap assembly 3296 has been secured to the support portion 3222, the curved needle 3249 and excess suture extending from the securement site at point G can be cut off. As stated above, a sleeve and strap assembly can be attached in the same manner at one or more of the other corners of the support portion 3222.

The resulting implant 3220 can be implanted within a pelvic region by associating the bullet trocar needle 3232 to a delivery device, such as delivery device 164 and using the delivery device to pull the strap assembly 3296 through a selected tissue, such as a sacrospinous ligament or tendineus arch of the levator ani muscle. The procedure for pulling such a sleeve and strap assembly through a tissue site has been described above with reference to other embodiments. After the implant 3220 is placed in a desired position, the suture 3242 or the sleeve 3295 and suture 3242 are cut at, for example, location D, to release the sleeve 3295 from the strap 3238, and the sleeve 3295 is pulled off the strap 3238 as previously described. If a suture portion remains attached to the strap 3238 at point A, it can be used to retrieve a cut strap portion after trimming the strap 3238 (if needed).

The sleeve and strap assembly 3296 can also be used alone, for example, for uterine suspension or to provide vaginal apical support. In such a procedure, the sleeve and strap assembly 3296 is placed through a vaginal incision, and the strap 3238 at point C is anchored (e.g., sutured or stitched) to the vaginal apex using the curved needle 3249 and suture 3242. The bullet trocar needle 3232 is then associated to a delivery device, such as device 164, or other suturing insertion device, to pass the trocar needle 3232 through the sacrospinous ligament (SSL). The trocar needle 3232 and attached suture leader 3230 are then retrieved and drawn outside the body by the catch of the delivery device. The sleeve and strap assembly 3296 is then pulled (via the leader 3230) through the SSL, or other anchoring tissue, until the strap 3238 can be seen (through the sleeve 3295) to exit on the other side of the SSL or anchoring tissue. The sleeve 3295 and strap 3238 are positioned and adjusted for the correct tension. Once positioned correctly, the leader 3230 and sleeve 3295 arc cut and the sleeve 3295 is gripped and pulled outward away from the body to leave the strap 3238 to engage the surrounding tissue. A remnant of the suture leader 3230 will still be attached to the strap 3238 at point A, and can be used to retrieve any cut portion of the strap from the body after trimming the strap 3238 (if necessary) as previously described.

Figure 57:
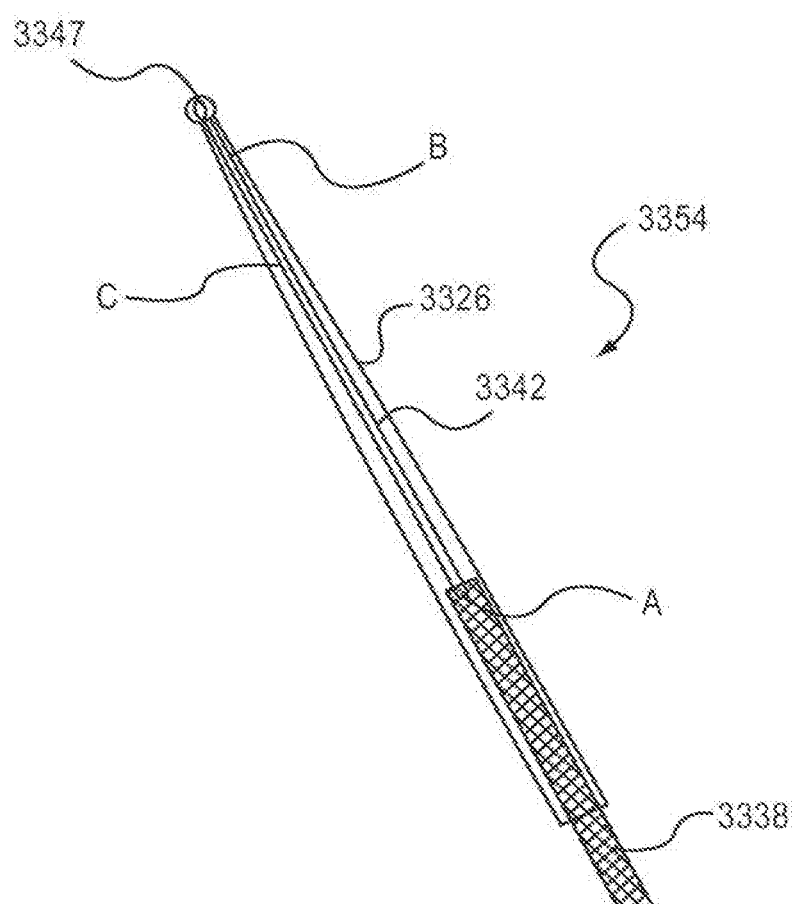
FIGS. 57 and 58 are each a top view of a different embodiment of a sleeve assembly.

FIG. 57 illustrates an embodiment of a sleeve assembly 3354 that is similar to the sleeve assemblies 1954 and 2054 described above. The sleeve assembly 3354 can be coupled to a strap of an implant to facilitate the delivery of the strap when inserted into tissue. The sleeve assembly 3354 includes a sleeve 3326, a suture 3342, and a connector 3347 coupled to an end of the sleeve 3226. As shown in FIG. 57, the sleeve 3326 only covers a portion of a strap 3338. For example, in some embodiments, only the portion of the strap that will be anchored in tissue is covered by the sleeve. In some embodiments, the sleeve covers substantially all of a strap.

The suture 3342 is threaded into an end portion of the strap 3338 at point A and forms a loop within the sleeve 3326. For example, to secure the suture 3342 to the strap 3338, two ends of the suture 3342 can be threaded into the strap 3338 at location A. The two ends are passed back through a loop formed in the suture 3342 to secure the suture 3342 to the strap 3338. The suture can alternatively be tied to the strap 3338. The suture ends are then threaded through the inside of the sleeve 3326 to a location B where the suture 3342 is secured to the sleeve 3326 and/or the connector 3347. For example, a heat seal can be used to secure one end of the suture 3342 to the sleeve 3326. In other embodiments, the suture 3342 can be molded to the connector 3347, tied to the connector 3347, tied to one wall of the sleeve 3326, tied to both walls of the sleeve 3326, or otherwise secured. In this embodiment, the connector 3347 can be used to associate to a delivery device, such as delivery device 264 to pass the sleeve assembly 3354 (and attached strap 3338) through a tissue.

After the sleeve assembly 3354 is pulled through a tissue, the suture 3342 and sleeve 3326 can be cut at, for example, location C, to release the sleeve 3326 from the strap 3338. In some embodiments, the suture 3342 can be exposed at point B (e.g., external to the sleeve 3326) such that only the suture 3342 need be cut to release the sleeve 3326 from the strap 3338. In other embodiments, the suture 3342 can run outside of the sleeve 3326. In some embodiments, a single strand of suture or multiple strands of suture can be used to secure the sleeve 3326 to the strap 3338.

Figure 58:
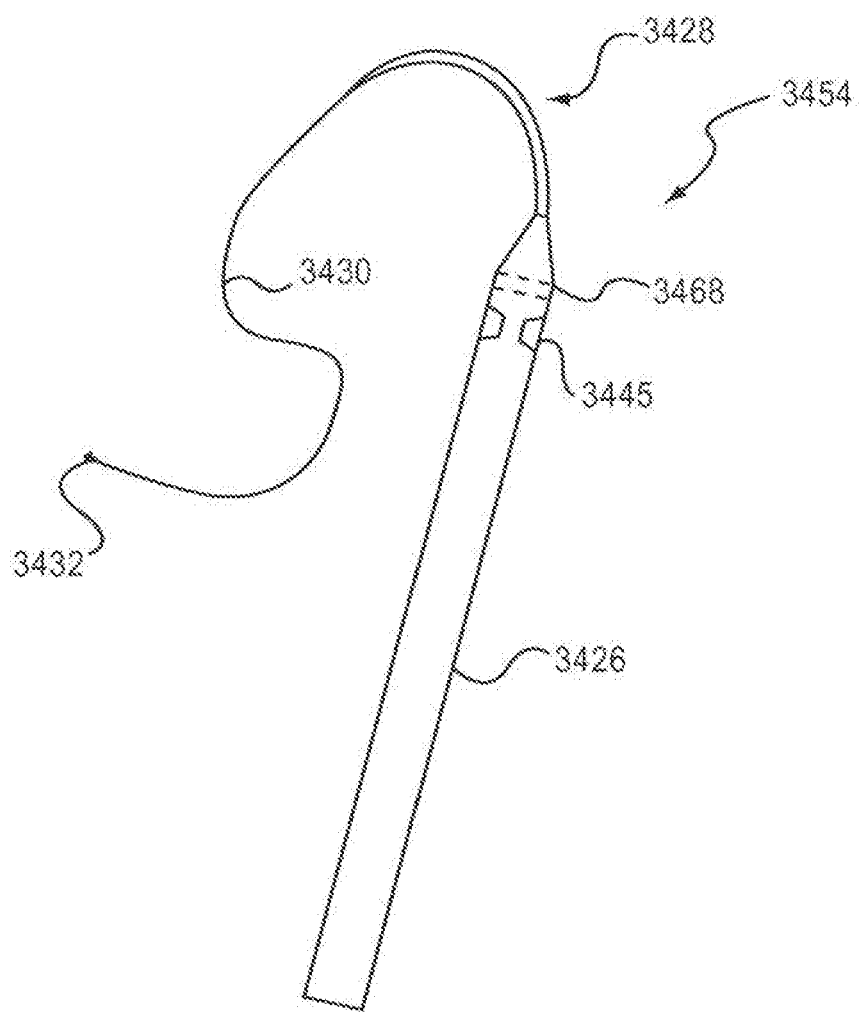

FIG. 58 illustrates a sleeve assembly having a curved and/or flexible dilator. A sleeve assembly 3454 includes a sleeve 3426 coupled to a dilator 3428, a leader 3430 and a trocar needle 3432. The trocar needle 3432 can be used to associate to a delivery device as previously described. The dilator 3428 can be pre-formed with a curved shape or can be flexible such that the dilator 3428 can curve or bend during insertion through a tissue. For example, the dilator 3428 can be configured to travel about 180 degrees at locations within a pelvic region, such as through a sacrospinous ligament or arcus tendineus and out through a vaginal incision. A heat seal 3468 can be used to secure the sleeve 3426 to a strap (not shown). For example, two walls of the sleeve 3426 can be heat bonded over the strap material.

The sleeve 3426 includes windows 3445 to provide access to cut a strap disposed within the sleeve 3426, or to cut a single wall of the sleeve 3426 and the strap to release the sleeve 3426 from the strap. The sleeve 3426 can then be removed by pulling the dilator 3428. If the strap and both walls of the sleeve 3426 are cut at window 3445, the window 3445 forms two flaps to allow easy grasping access for removal of the sleeve remnant. In an alternative embodiment, the sleeve 3426 can be sealed over a suture loop (not shown) threaded into the material of a strap. In such an embodiment, the strands of the suture loop can be arranged as far apart as possible within the sleeve 3426 to facilitate cutting a single strand of the suture loop for release of the sleeve 3426 from a strap of an implant. The windows 3445 can provide access to the suture loop for cutting.

Figure 59:
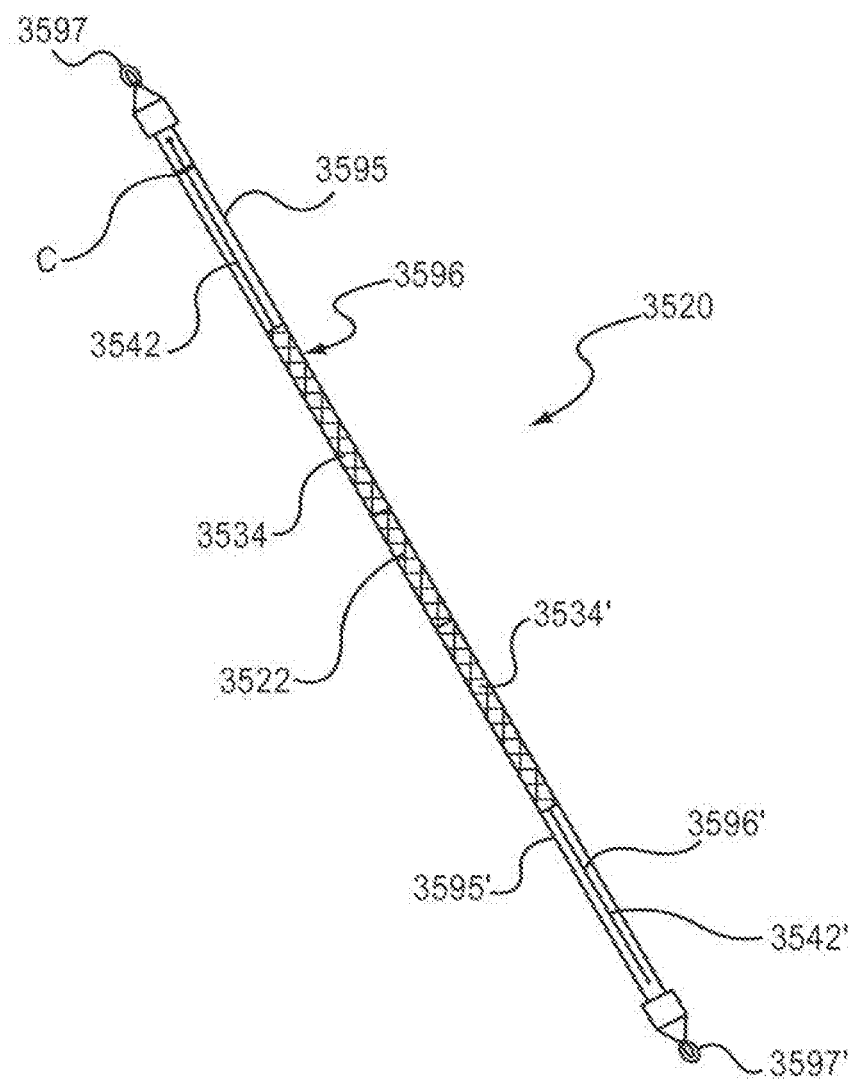
FIG. 59 is a top view of an embodiment of an implant.

FIG. 59 illustrates an embodiment of an implant that can be used, for example, as a urethral sling to treat, for example, incontinence. An implant 3520 can be delivered into a pelvic region through a small vaginal incision (e.g., a transvaginal approach). An incision can be made, for example, along an anterior vaginal mucosa. The incision can be, for example, 1.5 to 2.0 cm (0.59 to 0.79 inches) in length and can extend approximately 0.5 cm (0.2 inches) to the meatus. The vaginal epithelium is dissected from the underlying periurethral fascia. The implant 3520 is formed by attachment of two sleeve and strap assemblies 3596, 3596' to a urethral support 3522. The sleeve and strap assemblies 3596, 3596' are constructed the same as the sleeve and strap assemblies 1496 and 1496' described with reference to FIG. 28. Only the sleeve and strap assembly 3596 is described below, as the sleeve and strap assembly 3596' is similarly constructed and can be used and removed in the same manner as the sleeve assembly 3596.

The sleeve and strap assembly 3596 includes a sleeve 3595 disposed over a strap 3534, a suture 3542, and a loop connector 3597 (similar components, 3595, 3534', 3542' and 3597' are shown for sleeve and strap assembly 3596' in FIG. 59). The strap 3534 of the sleeve and strap assembly 3596 can be secured to the urethral support portion 3522 in a similar manner as for implant 3220 described with reference to FIG. 56. For example, a curved needle (or other type needle) can be used to suture or sew the strap 3534 to an end of the urethral support 3522. The connectors 3597 can be used to associate to a delivery device, such as delivery device 264 described herein. The sleeve 3595 can be removed from the strap after implantation as described above for previous embodiments. For example, the sleeve 3595 and/or suture 3542 can be cut at location C.

In some embodiments, it may be desirable to cut the implant 3520 into two halves, thereby creating two sleeve and strap assemblies that the user can then attach to a selected implant. In another alternative embodiment, a urethral support sling can have a length such that it includes straps. A sleeve assembly as described herein can be used to help deliver and secure the straps of the urethral support within a pelvic region.

The implant 3520 can be used in incontinence and uterine preservation procedures as well as pelvic floor repair procedures, and for other procedures or a combination thereof. Other types and configurations of sleeve and strap assemblies can alternatively be used. For example, a sleeve and strap assembly can include a trocar needle to associate to a delivery device 164. The urethral support 3522 can be made from a single piece of synthetic mesh material, and the center portion of the mesh can be de-tanged, with the straps (e.g., 3534) tanged for engagement with surrounding tissue. The implant 3520 can be deployed via a vaginal approach. The implant 3520 can be placed using various approaches, such as a vaginal approach or a pre-pubic approach.

Figure 60:
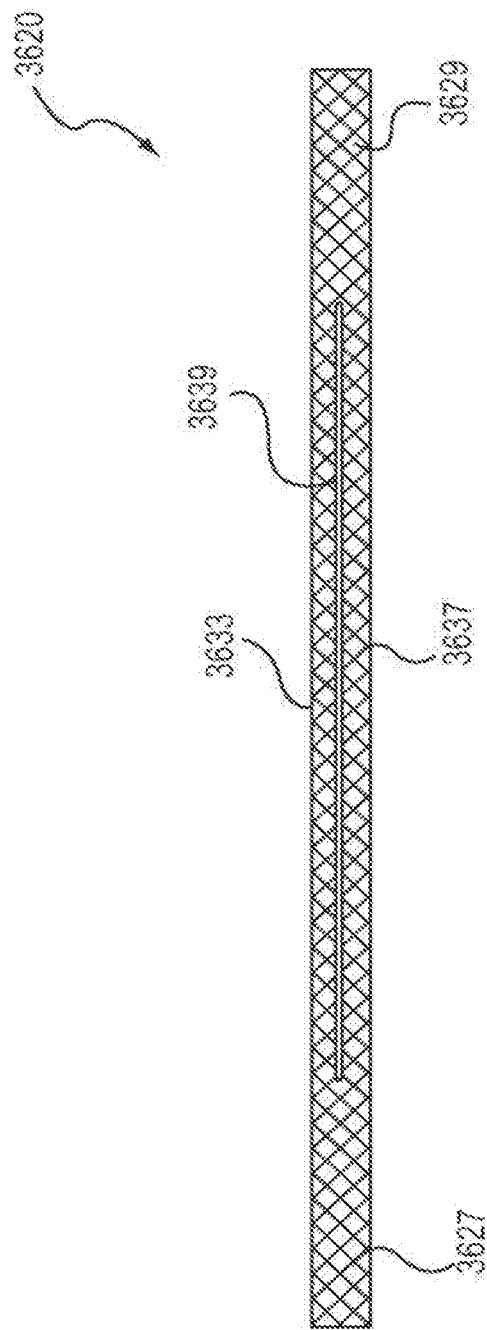
FIG. 60 is a top view of an other embodiment of an implant.
Figure 61:
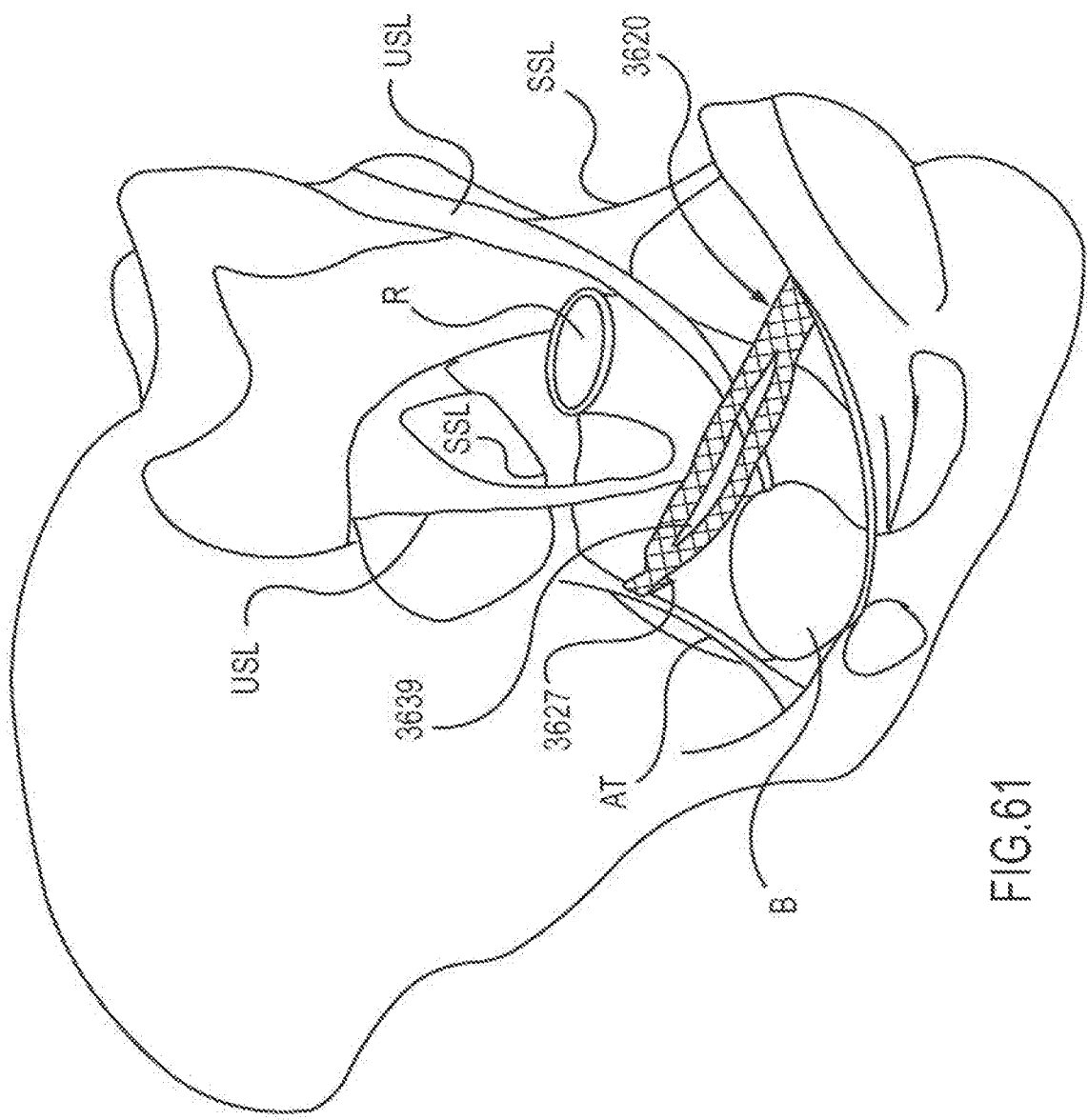
FIG. 61 is a side perspective view of a portion of a pelvic region and the implant of FIG. 60 disposed within the pelvic region.
Figure 62:
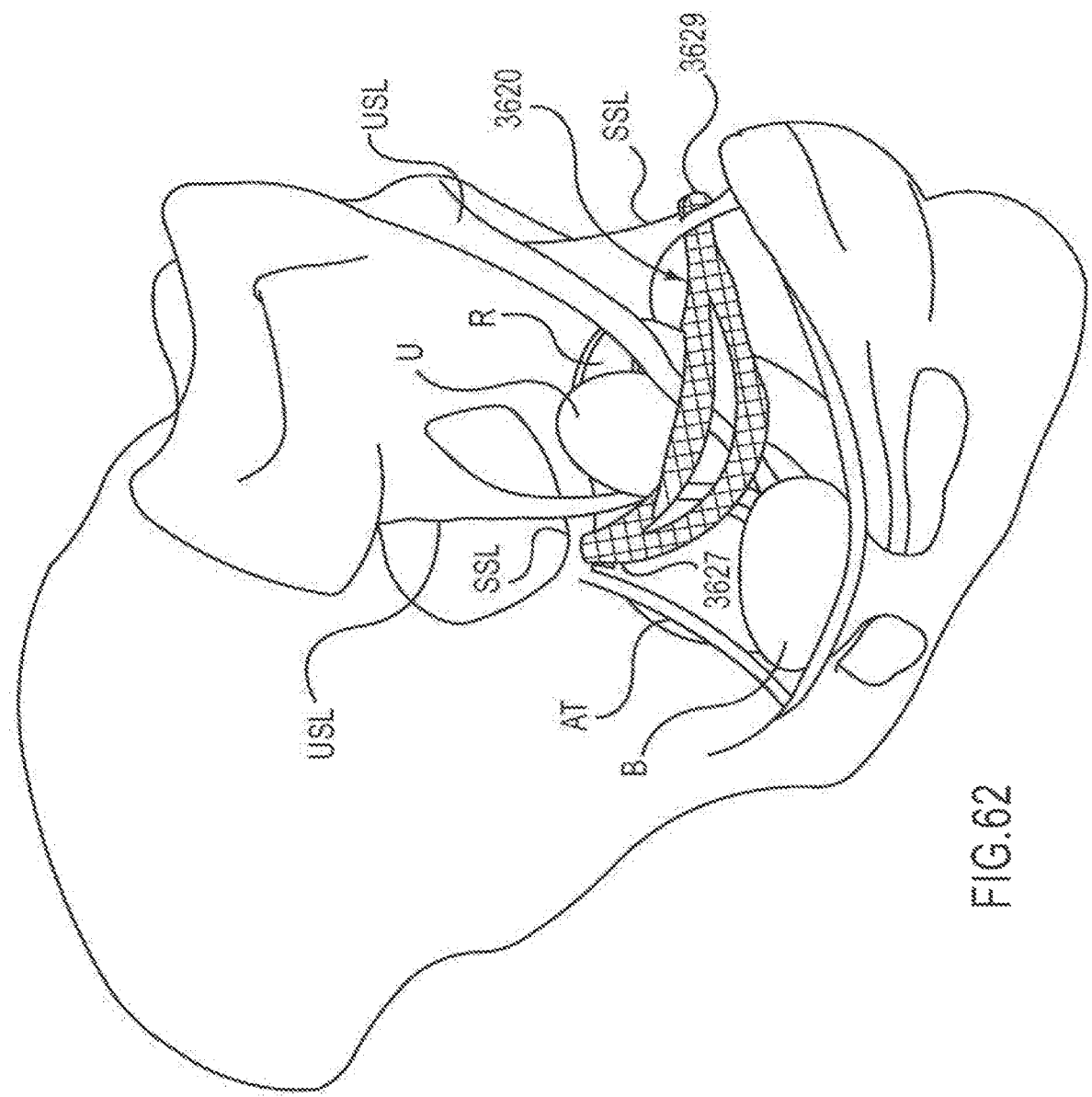
FIG. 62 is a side perspective view of a portion of a pelvic region and the implant of FIG. 60 disposed within the pelvic region.

FIGS. 60-62 illustrate another embodiment of an implant that can be placed in multiple different locations within a pelvic region to treat various female pelvic floor dysfunctions. An implant 3620 includes two support portions 3633 and 3637 that are separated by an opening 3639 defined by the implant 3620. The opening 3639 allows the support portions 3633 and 3637 to be spaced apart at various distances depending, for example, on the length and/or width of the opening. Although one opening is shown, in other embodiments, and implant can include multiple openings that define multiple support portions. In another embodiment, the implant has no opening and only a single support portion. In yet another embodiment the support portion is wider than the strap portion.

The implant 3620 also includes anchoring straps 3627 and 3629 that extend from the support portions 3633 and 3637. The implant 3620 can be placed within a pelvic region using any of the methods, devices and approaches described herein, and the anchoring straps 3627 and 3629 can be placed through a variety of different tissues and/or ligaments to support the support the support portions 3633 and 3637 in a desired position. The implant 3620 can also be formed with a mesh material to promote tissue in-growth as described above for previous embodiments. The two support portions 3633 and 3637 provided by the implant 3620 can reduce the number of implants needed to treat a particular prolapse condition or to treat multiple prolapse conditions.

In one example, the implant 3620 can be placed in a pelvic region and the anchoring straps 3627 and 3629 can be placed through an arcus tendineus (i.e., white line) on contra lateral sides of the pelvic region. FIG. 61 is a cut-away partial view of a pelvic region showing uteral sacral ligaments USL, sacrospinous ligaments SSL, a cut-away of the rectum R, the bladder B, and an arcus tendineus AT (on one-side only). As shown in FIG. 61, the implant 3620 can be placed within the pelvic region with the anchoring strap 3627 anchored to the arcus tendineus AT on one side of the pelvic region. The anchoring strap 3629 can be similarly secured to an arcus tendineus on the contra lateral side of the pelvic region (not shown in FIG. 61). The implant 3620 can be secured such that the opening 3639 is spread or pulled open a desired amount.

FIG. 62 illustrates another example of the implant 3620 placed in a pelvic region. FIG. 62 is a cut-away partial view of a pelvic region showing uteral sacral ligaments USL, a cut-away of the rectum R, the bladder B, an arcus tendineus AT (on one side only), sacrospinous ligaments SSL and a uterus U. In this example, the anchoring straps 3627 and 3629 of the implant 3620 are secured to a sacrospinous ligament SSL on each side of the pelvic region. This example illustrates the use of the implant 3620 for uterine preservation. The implant 3620 can be placed in a pelvic region and secured to alternative locations, such as, for example, pubo-urethral tissue, or an obturator.

Figure 63:
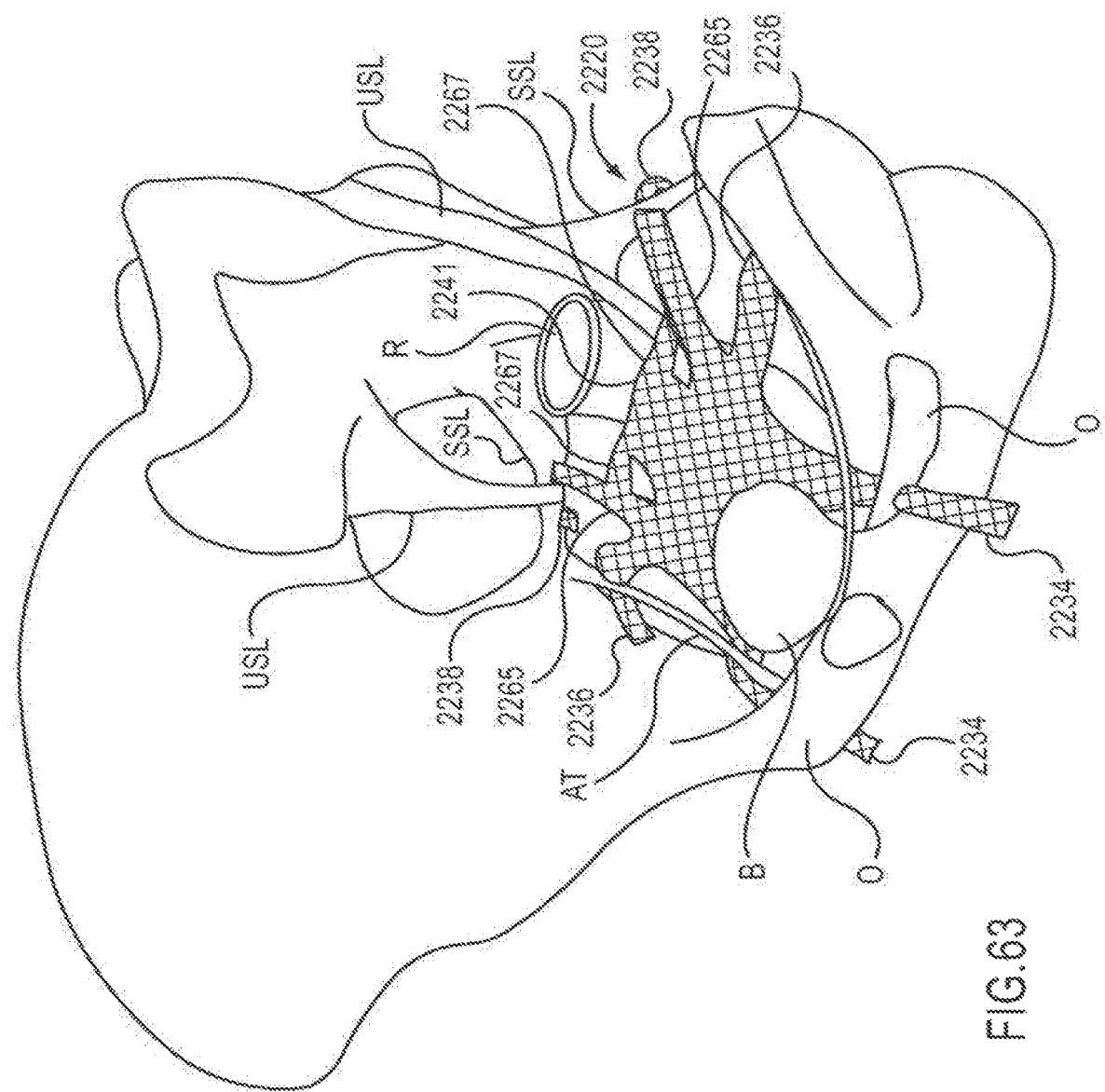
FIG. 63 is a side perspective view of a portion of a pelvic region and the implant of FIG. 38 shown disposed within the pelvic region.
Figure 64:
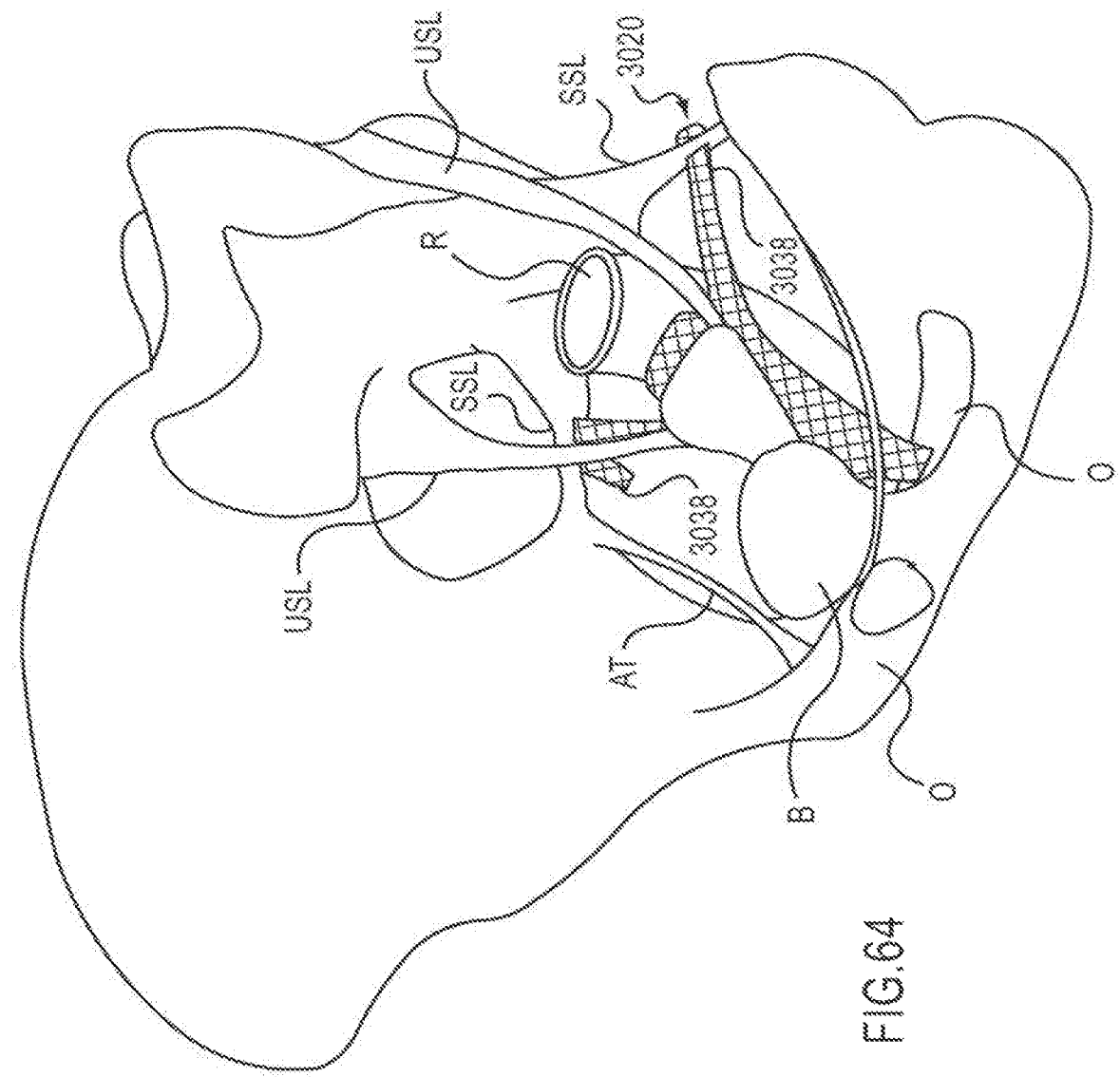
FIG. 64 is a side perspective view of a portion of a pelvic region and the implant of FIG. 51 shown disposed within the pelvic region.

FIGS. 63 and 64 each illustrate an example placement of an implant within a pelvic region. FIG. 63 is a cut-away partial view of a pelvic region showing uteral sacral ligaments USL, a cut-away of the rectum R, the bladder B, an arcus tendinous AT (on one side only), sacrospinous ligaments SSL and obturators O. In this example, the implant 2220 described above with reference to FIG. 38 is shown placed within the pelvic region. The straps 2234 are shown placed through obturators O. The straps 2236 are shown placed through the arcus tendineus AT, and the straps 2238 are shown placed through the sacrospinous ligaments SSL. The vaginal wrap portion 2241 is tucked around the vaginal cuff on a posterior side of the vagina (not shown). The posterior reinforcement straps 2267 can provide posterior apical support and the anterior reinforcement straps 2265 can provide anterior apical support.

FIG. 64 is a cut-away partial view of a pelvic region showing uteral sacral ligaments USL, a cut-away of the rectum R, the bladder B, an arcus tendineus AT (on one side only), sacrospinous ligaments SSL and obturators O. In this example, the implant 3020 described above with reference to FIG. 51 is shown placed within the pelvic region. The straps 3038 of the implant 3020 are shown placed through the sacrospinous ligaments SSL and the support portion 3046 is wrapped around the vaginal cuff.

Figure 65:
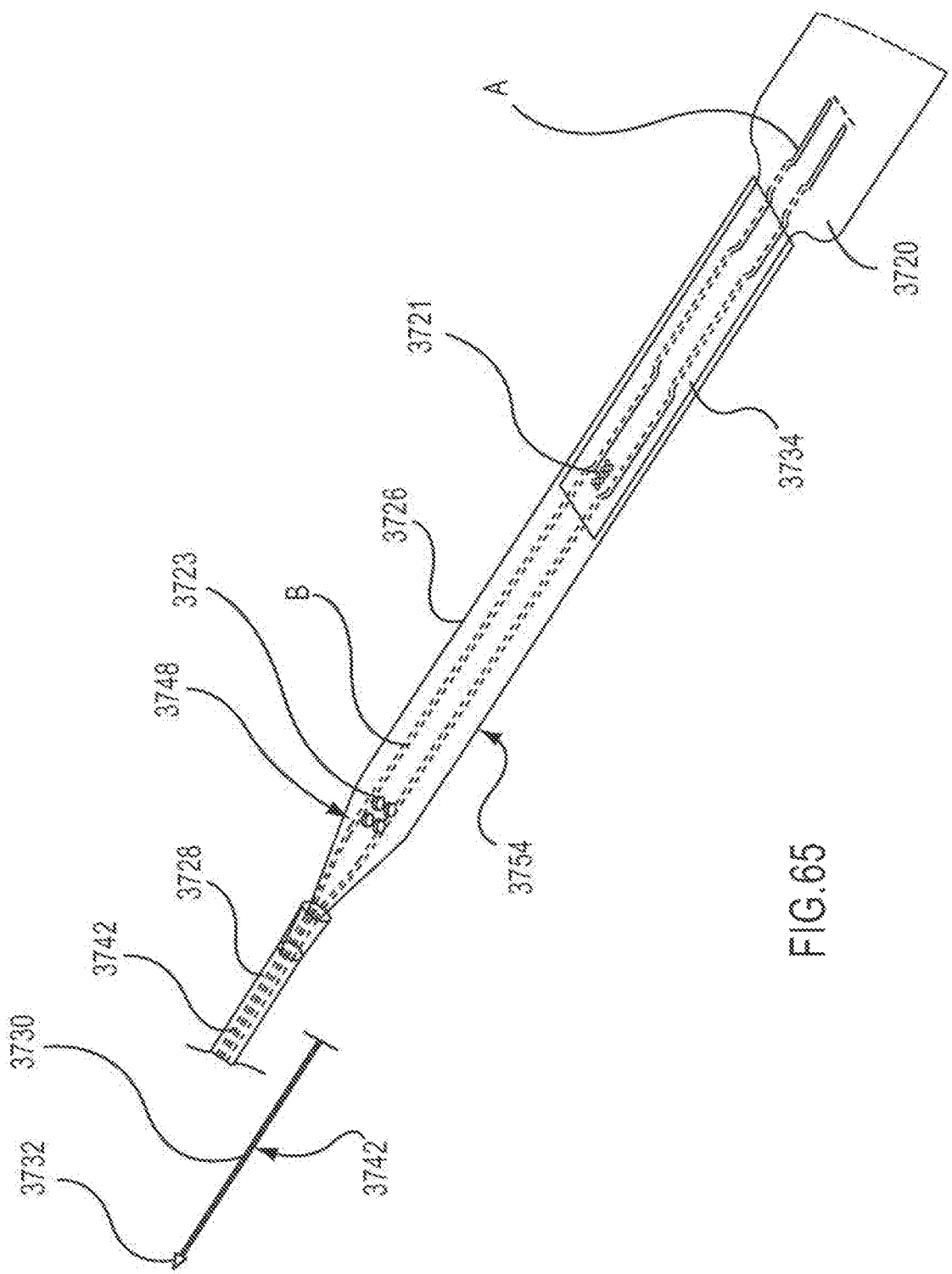
FIG. 65 is a side perspective view of a portion of an implant according to another embodiment of the invention.

FIG. 65 illustrates a portion of another embodiment of an implant illustrating a separator member in the form of a set of tacks. As shown in FIG. 65, an implant 3720 includes a strap 3734. A sleeve assembly 3754 is coupled to and disposed over the strap 3734. The sleeve assembly 3754 includes a sleeve 3726 and a tapered dilator 3728. The dilator 3728 can be coupled to the sleeve 3726 as described above for other embodiments, for example, by crimping, heat sealing, stitching, stretching, tip tipping, etc. Alternatively, the sleeve 3726 can be formed to include a portion that forms a tapered dilator. The dilator 3728 can be used to expand or enlarge a passage during insertion through a tissue, to ease the transition to a cross-section or size of the sleeve 3726. The sleeve 3726 is also tapered, which also helps provide a lead-in through the tissue.

The sleeve 3726 is secured to the strap 3734 with a suture 3742. The suture 3742 is looped within the sleeve 3726 and weaved or threaded through the implant 3720 at location A. The suture 3742 can alternatively be coupled to the strap 3734 using, for example, any of the methods described above for the dilator to sleeve coupling, for example, by crimping, heat sealing, stitching, stretching, tip tipping, etc. In some embodiments, a suture can be threaded to or secured to a strap, for example by knotting. The strands of the sutures 3742 forming the loop through the sleeves 3726 extend through an interior of the dilator 3728 and can be crimped closed and heat bonded to an interior wall of the dilator 3728 (not shown in FIG. 65) to maintain the strap 3734 within the sleeve 3726.

A leader suture 3730 is coupled to and extends distally from the dilator 3728. Alternatively, a leader portion of the suture 3742 can extend distally from the dilator 3728. A trocar needle 3732 is coupled to a distal end of the leader suture 3730. As described previously, the trocar needle 3732 can be used to associate the implant 3720 to a delivery device, such as a delivery device 164 described above.

In this embodiment, the sleeve assembly 3754 includes a separator 3748 in the form of a set of tacks 3723 (four tacks 3723 are shown, but other quantities can be used) disposed between two strands of the looped suture 3742 and near a distal end of the sleeve 3726. The set of tacks 3723 couple a top wall and a bottom wall of the sleeve 3726 together, and maintain separation of the strands of the looped suture 3742 within the sleeve 3726. A second set of tacks 3721 can be used to lightly secure the strap 3734 to the sleeve 3726. As described above, the separation of the strands of the suture 3742 enable or help facilitate a cut to be made through only a single strand of the looped suture 3742 at, for example, location B, during removal of the sleeve 3726. Using a set or group of small tacks (rather than a single large tack) can help maintain flexibility of the strap 3734 during delivery of the strap 3734 into a pelvic region where it may need to fold or bend during insertion.

Figure 66A:
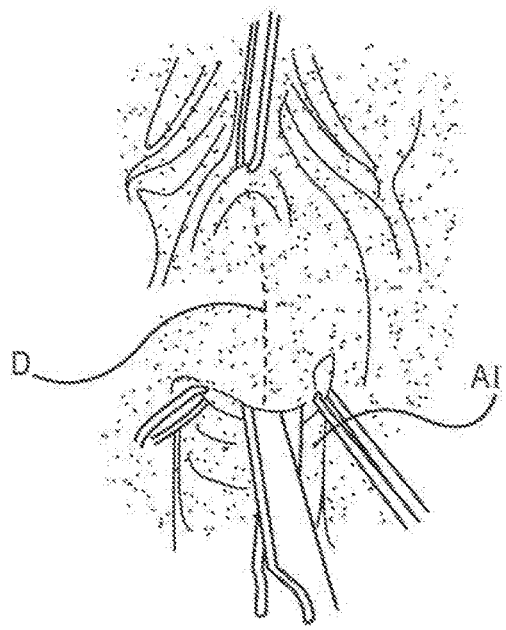
FIGS. 66A-66D illustrate an example of an anterior incision procedure.
Figure 66B:
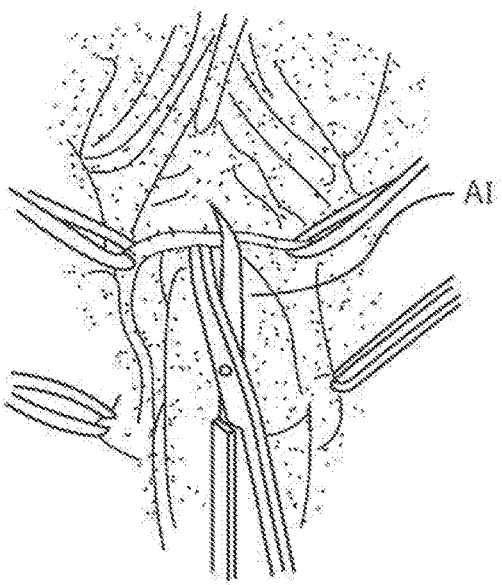
Figure 66C:
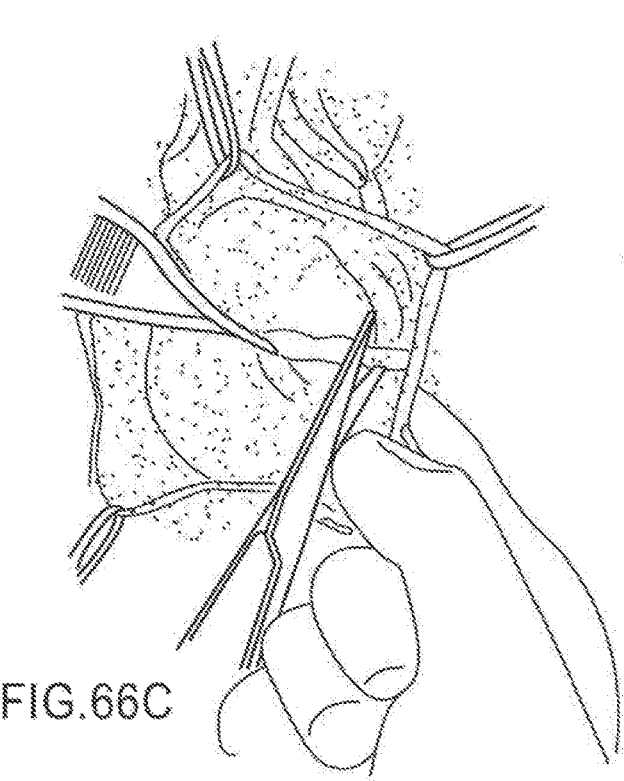
Figure 66D:
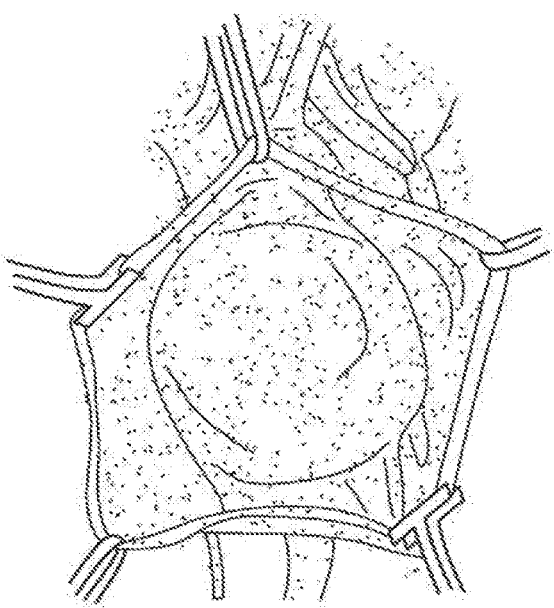

FIGS. 66A-66D illustrate a procedure for making an anterior incision in a vagina. FIG. 66A illustrates an initial midline anterior vaginal wall incision AI. The anterior incision AI can be, for example, about 4 cm long extending about 1 cm from the cervix to the level of the proximal urethra as shown by the dashed line D shown in FIG. 66A. FIG. 66B shows the incision extended to the level of the proximal urethra. FIG. 66C illustrates a dissection and traction on the bladder. Such a sharp dissection and traction can facilitate dissection of the bladder off the vaginal wall. FIG. 66D illustrates a completed mobilization of a cystocele off the vaginal wall.

Figure 67A:
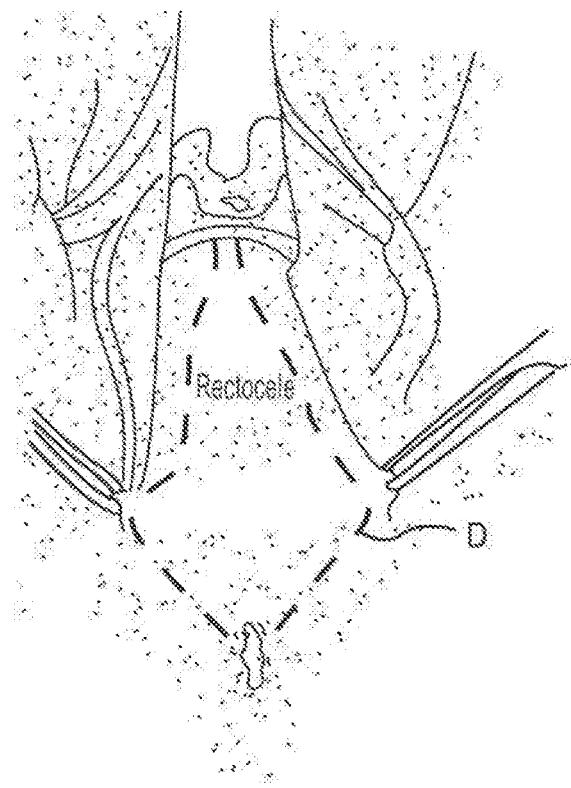
FIGS. 67A-67F illustrate an example of a posterior incision procedure.
Figure 67B:
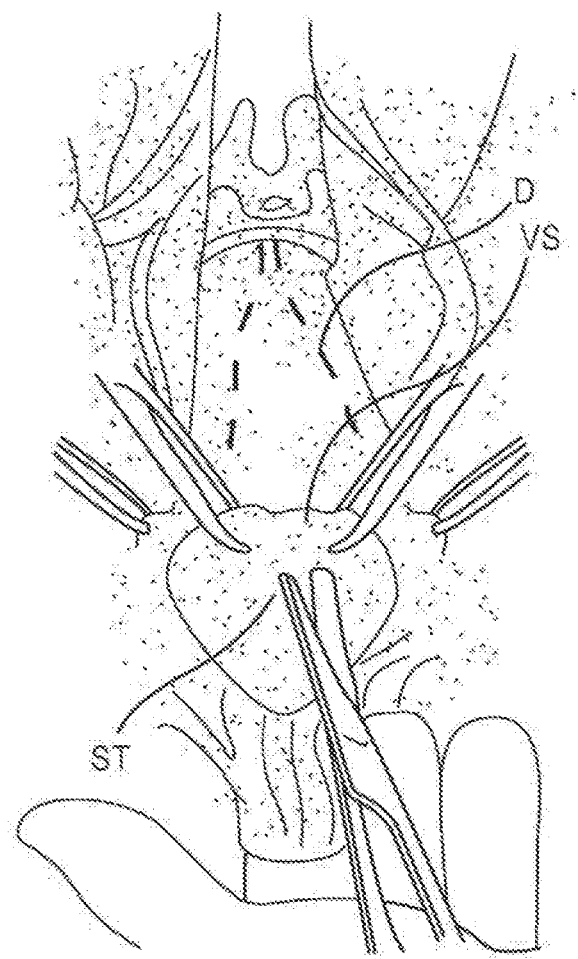

FIGS. 67A-67F illustrate an example procedure for making a posterior incision where excess tissue is excised in a vagina to treat, for example, a rectocele. The dashed line D illustrates the area of perineal skin and posterior vaginal wall to be excised. FIG. 67B illustrates a sharp dissection of the posterior vaginal wall from the anterior rectal wall. As shown in FIG. 67B, the dissection can be aided with a finger in the patient's rectum. Also shown in FIG. 67B is the subepithelial tunnel of rectovaginal space labeled ST, and a full thickness vaginal strip to the apex of the vagina labeled VS.

Figure 67C:
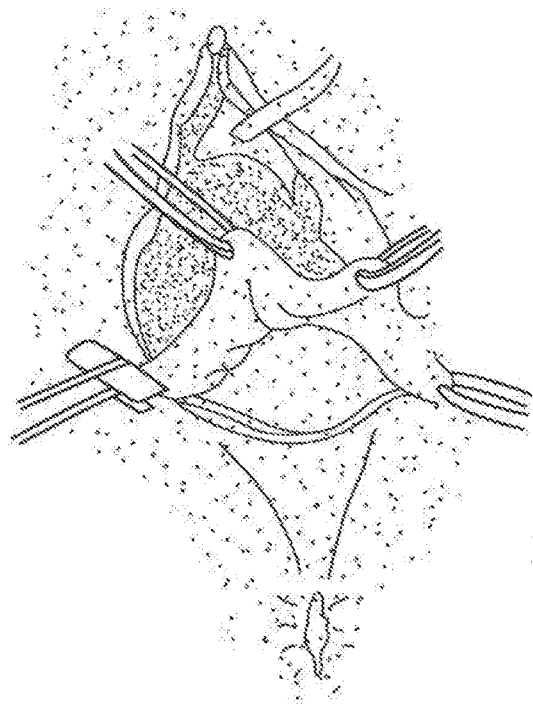
Figure 67D:
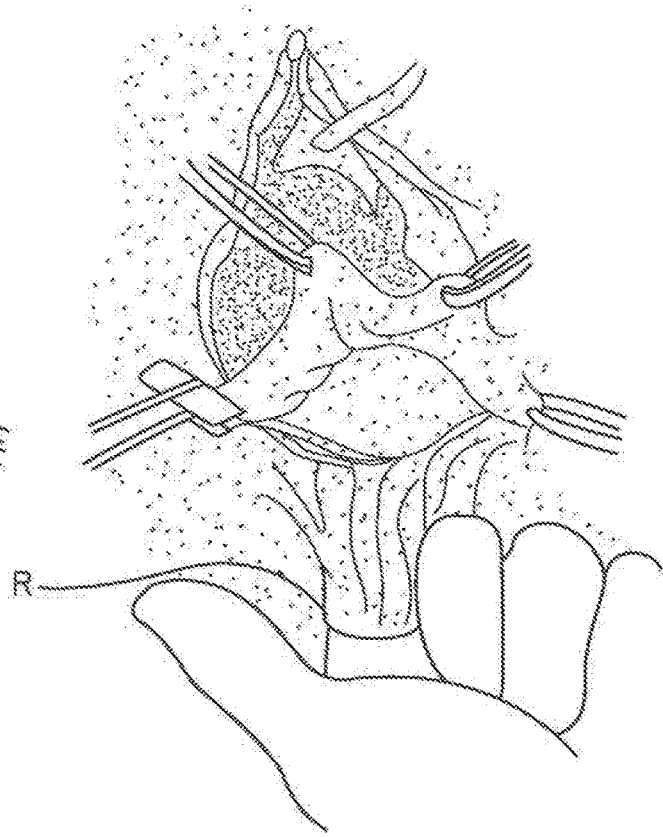
Figure 67E:
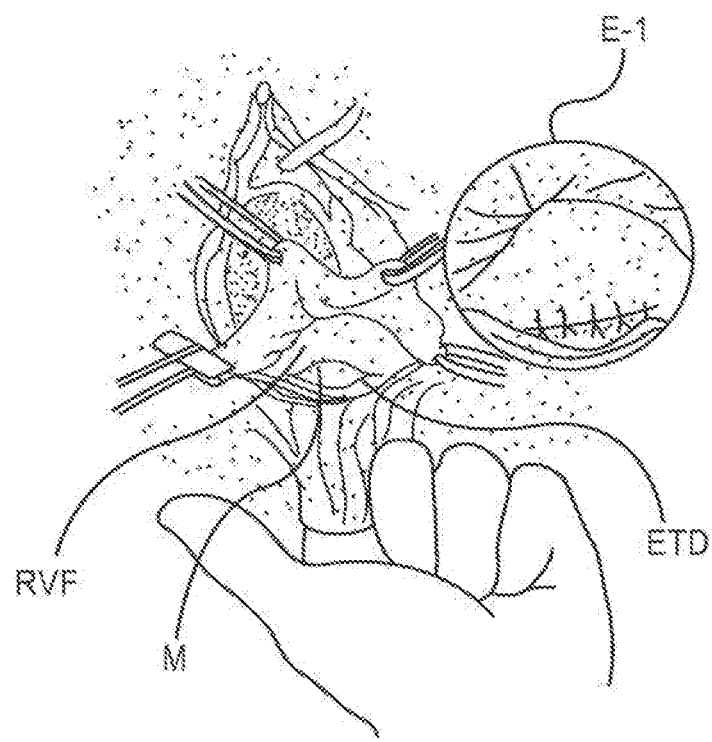
Figure 67F:
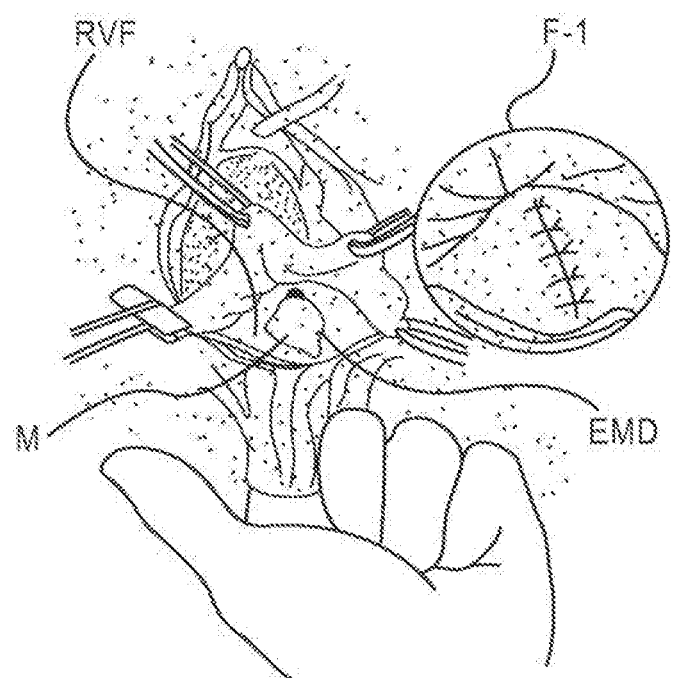

FIG. 67C illustrates various potential defects that may be encountered at the time of a rectocele repair procedure, and FIG. 67D illustrates how placing a finger in the rectum R and elevating the anterior rectal wall can help delineate fascial tears. FIG. 67E shows the rectovaginal fascia RVF, the anterior rectal mucosa M, and an edge of a transverse defect ETD. FIG. 67E illustrates a low transverse defect between the perineum and a distal edge of the rectovaginal fistula. The inset figure labeled E-1 illustrates a defect-specific closure with interrupted sutures. FIG. 67F shows the rectovaginal fascia RVF, the anterior rectal mucosa M, and an edge of a midline defect EMD. FIG. 67F illustrates a midline longitudinal defect and the inset figure labeled F-1 illustrates a defect-specific closure with interrupted sutures.

The implants described herein can be formed with a variety of different materials, such as biocompatible plastics and/or metals. In some embodiments, the implant is formed at least in part with a mesh material to promote tissue in-growth. In implant can also be formed fully or in part with biological or natural materials or combinations of biological and synthetic materials. An implant can be formed at least in part with, for example, the Advantage® Mesh by BSC. Alternatively the implant can be formed with Polyform® Synthetic Mesh material by BSC.

The sutures can be a monofilament or braided and can be formed with a variety of different biocompatible materials. For example, the suture material can include absorbable and non-absorbable material, and/or a combination thereof. The various other components described herein can be formed with one or more biocompatible plastics and/or metals.

In one embodiment, an apparatus includes a support member implantable within a pelvic region and a strap extending from the support member. The strap has a length and is configured to be secured within a pelvic tissue to support the support member within the pelvic region. A sleeve is releasably disposed over at least a portion of the strap and has a length greater than the length of the strap. In some embodiments, of this apparatus the length of the sleeve is at least twice as long as the length of the strap. In some embodiments, the length of the strap is such that the strap can be positioned at a tissue securement location within the pelvic region, but cannot extend to a vaginal incision after being placed at least partially through the tissue securement location, and the length of the sleeve is sufficiently long such that the sleeve can extend from the strap after being positioned at the tissue securement location to the vaginal incision.

The above apparatus can also include the following features. In some embodiments, the sleeve includes a first portion and a second portion that define an interior, and the apparatus further includes a suture disposed at least partially within the interior of the sleeve and forming two strands of suture within the interior of the sleeve. The two strands are separated by a distance defined by a separator portion of the sleeve. In some embodiments, the support member is formed with a first material and the strap is formed with a second material different than the first material. In some embodiments, the strap is secured to the sleeve with a suture. In some embodiments, the sleeve includes a first wall and a second wall defining an interior and the apparatus further includes a suture at least partially disposed within the sleeve and coupled to the support portion. In some embodiments, the support member includes a first portion that is configured to support a bladder neck and a second portion that is configured to be wrapped at least partially around a vaginal cuff in a posterior region of the pelvic space. In some embodiments, the support member includes a first portion configured to support a bladder neck and a second portion configured to support a uterus. In some embodiments, the support member includes a portion configured to support a uterus.

In another embodiment, an apparatus includes a support member implantable within a pelvic region and a strap extending from the support member and configured to be secured within a pelvic tissue to support the support member within the pelvic region. A sleeve is releasably disposed over at least a portion of the strap and has a first wall and a second wall that define an interior space. A suture is coupled to the strap and also to the sleeve. The suture is disposed at least partially within the interior space of the sleeve and forms two strands of suture within the interior space of the sleeve. The two strands are separated by a distance defined by a separator portion of the sleeve. In some embodiments, the apparatus also includes a dilator that is coupled to the a distal end portion of the sleeve. In some embodiments, the sleeve defines a window and the strap is accessible within the interior space of the sleeve through the window. In some embodiments, the strap is formed with a mesh material and includes a tanged edge to engage tissue within a pelvic region. In some embodiments, the strap includes protrusions formed on a surface of the strap that are configured to engage pelvic tissue to help anchor the strap to the pelvic tissue. In some embodiments, the support member is configured to provide support to a bladder neck when the strap is secured to a pelvic tissue.

In another embodiment, an apparatus includes a support member that is implantable within a pelvic region. A first strap extends from the support member and configured to be secured to a an arcus tendineus when the support member is implanted within the pelvic region. A second strap extends from the support member and distal of the first strap and is configured to be secured to a sacrospinous ligament when the support member is implanted within a pelvic region. The first strap has a length such that the first strap can be secured to the arcus tendineus but cannot extend to a vagina after being secured to the arcus tendineus. The second strap has a length such that the second strap can be secured to the sacrospinous ligament but cannot extend to the vagina after being secured to the sacrospinous ligament. The first strap and the second strap are configured to help support the support member at least partially beneath the bladder neck when the first strap is secured to the arcus tendineus and the second strap is secured to the sacrospinous ligament.

The above apparatus can also include the following features. In some embodiments, the apparatus can further include a tail portion that extends from the support member and is configured to be wrapped around a vaginal cuff in a posterior region of the pelvic region. In some embodiments, the apparatus further includes a sleeve disposed over at least one of the first strap or the second strap, a dilator coupled to a distal end of the sleeve, a suture coupled to the strap and to the sleeve, and a needle coupled to a distal end portion of the suture that is configured to associate the strap to a delivery device.

In some embodiments, the apparatus includes a sleeve disposed over at least one of the first strap or the second strap and a suture that couples the sleeve to the strap. The suture has a first strand and a second strand disposed within the sleeve and is separated by a separator portion of the sleeve. In some embodiments, the apparatus includes shoulder extending from the support member and proximal of the first strap and that is configured to be secured to at least one of the arcus tendineus or an obturator. In some embodiments, the apparatus includes a shoulder extending from the support member and proximal of the first strap that is configured to be secured to at least one of the arcus tendineus or an obturator via a suture. In some embodiments, the apparatus includes a first dilator coupled to the first strap, and a second dilator coupled to the second strap. The first dilator is a first color and the second dilator is a second color that is different than the first color.

In another embodiment, a method includes inserting a pelvic implant through an anterior vaginal incision and into a pelvic region. The pelvic implant includes a support portion, a strap extending from the support portion, and a sleeve disposed over the strap, where the sleeve has a length greater than a length of the strap. The sleeve and strap are pulled at least partially through a pelvic tissue such that a first portion of the sleeve is disposed within the pelvic tissue and a second portion of the sleeve extends through the vaginal incision and the strap is disposed at least partially within the pelvic tissue but does not extend through the vaginal incision. The sleeve is removed from the strap leaving the strap at least partially disposed within the pelvic tissue. In some embodiments of this method the pelvic tissue is an arcus tendineus.

In another embodiment, a method includes inserting an implant through a vaginal incision and into a pelvic region. The implant includes a first strap and a second strap both extending from a support portion. The first strap is placed through a sacrospinous ligament of a first side of the pelvic region and the second strap is placed through an arcus tendineus of the first side of the pelvic region. An anterior portion of the support portion is secured to at least one of an obturator or the arcus tendineus of the first side of the pelvic region. In some embodiments, the implant includes a third strap and a fourth strap, and the method includes placing the third strap through a sacrospinous ligament of a second contra lateral side of the pelvic region and placing the fourth strap through an arcus tendineus of the second contra lateral side of the pelvic region.

In another embodiment, a method includes providing a pelvic implant having a strap extending from a support portion of the implant and the strap has a first length. A portion of the support portion of the implant is cut such that the strap has a second length greater than the first length of the strap. After cutting the implant, at least a portion of the strap is placed through a pelvic tissue to at least partially secure the implant within a pelvic region of a patient. In some embodiments, cutting the implant includes making a first cut on the support portion of the implant adjacent a first side of the strap, and making a second cut on the support portion of the implant adjacent a second side of the strap. In some embodiments, the implant includes a cut line disposed on the support portion of the implant to indicate a location for cutting the portion of the support portion of the implant.

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of embodiments as described herein. Thus, the breadth and scope of the invention should not be limited by any of the above-described embodiments, but should be defined only in accordance with the following claims and their equivalents.

For example, the implants described herein can be delivered and implanted within a pelvic region using any of the devices, methods and approaches described herein or other devices and delivery methods not specifically described. Various delivery aids such as sleeves, dilators, connectors, etc., can be used to deliver the implants to a pelvic region. An implant can have various other shapes, sizes and configurations not specifically described. Any of the implants described herein can include tangs, dimples, protrusions or other anchoring features. An implant according to any of the embodiments can be assembled to a delivery device or delivery aid by a user (e.g., physician) or provided preassembled to the user.

In another example, any of the implants described herein can be cut to a desired size. For example, a strap and/or support portion can be cut or trimmed to a desired size (e.g., length and/or width). The implants described herein can be used to treat a variety of different female pelvic floor dysfunctions including, for example, cystoceles, rectoceles, enteroceles, and/or vaginal prolapses. The implants can also be used to treat paravaginal repairs, provide uterine support, or treat incontinence.

In addition, a fixation or placement device does not have to be included as part of a strap, sleeve, or any other element of an implant. For example, an implant can be secured within tissue using other fixation methods, such as, for example, a heating element, glue stick, or a needle and suture. Other attachment methods include a thermal energy source, mechanical or chemical fixation techniques or a combination thereof.

What is claimed is:

1. An apparatus, comprising:
    a support member implantable within a pelvic region;
    a first strap extending from the support member, the first strap being configured to be secured within a pelvic tissue to support the support member within the pelvic region;
    a shoulder extending from the support member and disposed proximal of the first strap;
    a first sleeve releasably disposed over at least a portion of the first strap;
    a dilator coupled to a distal end portion of the sleeve;
    a second strap extending from the support member and disposed distal of the first strap; and
    a second sleeve disposed apart from the first sleeve and being releasably disposed over at least a portion of the second strap.

2. The apparatus of claim 1, wherein a length of the first sleeve is at least twice as long as a length of the first strap.

3. The apparatus of claim 1, wherein a length of the first strap is such that the first strap can be positioned at a tissue securement location within the pelvic region, but cannot extend to a vaginal incision after being placed at least partially through the tissue securement location, a length of the first sleeve is sufficiently long such that the first sleeve can extend from the first strap after being positioned at the tissue securement location to the vaginal incision.

4. The apparatus of claim 1, wherein the first sleeve includes a first portion and a second portion defining an interior, the apparatus further comprising:
    a suture disposed at least partially within the interior of the first sleeve and forming two strands of suture within the interior of the sleeve, the two strands being separated by a distance defined by a separator portion of the first sleeve.

5. The apparatus of claim 1, wherein the support member is formed with a first material and the first strap is formed with a second material different than the first material.

6. The apparatus of claim 1, wherein the first strap is secured to the first sleeve with a suture.

7. The apparatus of claim 1, wherein the first sleeve includes a first wall and a second wall defining an interior, the apparatus further comprising:
    a suture at least partially disposed within the first sleeve and coupled to the support portion.

8. The apparatus of claim 1, wherein the support member includes a first portion and a second portion, the first portion configured to support a bladder neck, the second portion configured to be wrapped at least partially around a vaginal cuff in a posterior region of the pelvic region.

9. The apparatus of claim 1, wherein the support member includes a first portion and a second portion, the first portion configured to support a bladder neck, the second portion configured to support a uterus.

10. The apparatus of claim 1, wherein the support member includes a portion configured to support a uterus.

11. An apparatus comprising:
a support member implantable within a pelvic region;
a first strap extending from the support member and configured to be secured to an arcus tendineus when the support member is implanted within the pelvic region;
a second strap extending from the support member and distal of the first strap and configured to be secured to a sacrospinous ligament when the support member is implanted within the pelvic region,
the first strap having a length such that the first strap can be secured to the arcus tendineus but cannot extend to a vagina after being secured to the arcus tendineus, the second strap having a length such that the second strap can be secured to the sacrospinous ligament but cannot extend to the vagina after being secured to the sacrospinous ligament, the first strap and the second strap configured to help support the support member at least partially beneath a bladder neck when the first strap is secured to the arcus tendineus and the second strap is secured to the sacrospinous ligament; and
a shoulder extending from the support member and disposed proximal to the first strap, the shoulder being configured to be secured to bodily tissue.

12. The apparatus of claim 11, further comprising:
a tail portion extending from the support member and configured to be wrapped around a vaginal cuff in a posterior region of the pelvic region.

13. The apparatus of claim 11, further comprising:
a sleeve disposed over at least one of the first strap or the second strap;
a dilator coupled to a distal end of the sleeve;
a suture coupled to the at least one of the first strap or the second strap and to the sleeve; and
a needle coupled to a distal end portion of the suture, the needle configured to associate the strap to a delivery device.

14. The apparatus of claim 11, further comprising:
a sleeve disposed over at least one of the first strap or the second strap; and
a suture coupling the sleeve to the at least one of the first strap or the second strap, the suture having a first strand and a second strand disposed within the sleeve and separated by a separator portion of the sleeve.

15. The apparatus of claim 11, wherein the shoulder configured to be secured to the at least one of the arcus tendineus or an obturator via a suture.

16. The apparatus of claim 11, further comprising:
a first dilator coupled to the first strap, the first dilator being a first color; and
a second dilator coupled to the second strap, the second dilator being a second color different than the first color.

17. The apparatus of claim 11, wherein the shoulder is configured to be secured to at least one of a levator muscle, the arcus tendinous, and an obturator.

18. A method, comprising:
inserting a pelvic implant through an anterior vaginal incision and into a pelvic region, the pelvic implant including a support portion, a strap extending from the support portion, and a sleeve disposed over the strap, the sleeve having a length greater than a length of the strap;
pulling the sleeve and strap at least partially through a pelvic tissue such that a first portion of the sleeve is disposed within the pelvic tissue and a second portion of the sleeve extends through the vaginal incision and the strap is disposed at least partially within the pelvic tissue but does not extend through the vaginal incision;
cutting a first portion of a suture that couples the strap to the sleeve; and
removing the sleeve from the strap leaving the strap at least partially disposed within the pelvic tissue.

19. The method of claim 18, wherein the pelvic tissue is an arcus tendineus.

20. The method of claim 18, wherein the pelvic tissue is a sacrospinous ligament.

* * * * *